United States Patent
Rahme et al.

(10) Patent No.: US 10,550,431 B2
(45) Date of Patent: Feb. 4, 2020

(54) METHODS AND ASSAYS RELATING TO THE TREATMENT OF INFECTION

(71) Applicant: THE GENERAL HOSPITAL CORPORATION, Boston, MA (US)

(72) Inventors: Laurence Rahme, Brookline, MA (US); Shuangchun Yan, Cambridge, MA (US); Yok-Ai Que, Pully (CH); Amy Tsurumi, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 113 days.

(21) Appl. No.: 15/027,067

(22) PCT Filed: Nov. 13, 2014

(86) PCT No.: PCT/US2014/065444
§ 371 (c)(1),
(2) Date: Apr. 4, 2016

(87) PCT Pub. No.: WO2015/073665
PCT Pub. Date: May 21, 2015

(65) Prior Publication Data
US 2016/0237497 A1    Aug. 18, 2016

Related U.S. Application Data

(60) Provisional application No. 61/903,548, filed on Nov. 13, 2013.

(51) Int. Cl.
*G01N 33/68* (2006.01)
*C12Q 1/6883* (2018.01)

(52) U.S. Cl.
CPC ....... *C12Q 1/6883* (2013.01); *G01N 33/6893* (2013.01); *C12Q 2600/106* (2013.01); *C12Q 2600/156* (2013.01); *C12Q 2600/158* (2013.01); *G01N 2800/26* (2013.01); *G01N 2800/52* (2013.01)

(58) Field of Classification Search
None
See application file for complete search history.

(56) References Cited

U.S. PATENT DOCUMENTS

2011/0190143 A1* 8/2011 Payen de la Garanderie ............. C12Q 1/6883
506/7

OTHER PUBLICATIONS

Conceicao. Thrombospondin: a new biomarker for the progressive and non-progressive HIV disease. Abstract #MOLBP09. Presented at: 7th IAS Conference on HIV Pathogenesis, Treatment and Prevention; Jun. 30-Jul. 3, 2013; Kuala Lumpur, Malaysia.*
Iglesias-Ussel et al. High leveldo CD2 expression identify HIV-1 latently infected resting memory CD4+ T cells in virally suppressed subejcts. Journal of Virology, Jun. 12, 2013; 87(16):9148-9158.*
Huang et al. Use of thrombospondin level to predict the clinical course of atopic dermatitis associated with food hypersensitivity or skin infection. Journal of Dermatological Science, 1996; 11:59-63 (Year: 1996).*
Songok et al. Microarray Analysis of HIV Resistant Female Sex Workers Reveal a Gene Expression Signature Pattern Reminiscent of a Lowered Immune Activation State. PLOS One, 2012; 7(1):e30048 (Year: 2012).*
Simmons et al. Stable RNA interference of host thrombospondin-1 blocks Trypanosoma cruzi infection. FEBS Letters, 2006; 580: 2365-2370 (Year: 2006).*
Wong et al. Genome-level expression profiles in pediatric septic shock indicate a role for altered zinc homeostasis in poor outcome. Physiological Genomics, 2007; 30:146-155 (Year: 2007).*
Goldmann et al. Transcriptome Analysis of Murine Macrophages in Response to Infection with *Streptococcus pyogenes* Reveals an Unusual Activation Program. Infection and Immunity, 2007; 75(8):4148-4157 (Year: 2007).*
Hyrcza (Gene Expression Changes in Immune Cells during Human Immunodeficiency Virus 1 (HIV-1) Infection, University of Toronto (Canada), Ann Arbor, 2009. ProQuest, https://search.proquest.com/docview/1353201984?accountid=14753 (Year: 2009).*
Paul et al. 2010. Systemic Review and Meta-Analysis of the Efficacy of Appropriate Empiric Antibiotic Therapy for Sepsis; Antimicrobial Agents and Chemotherapy 54(11):4851-4863 (Year: 2010).*
Genbank: DR005238.1 "TC120970 Human prostate, large insert, pCMV expression library *Homo sapiens* cDNA clone TC120970 5-similar to *Homo sapiens* MyoD family inhibitor domain containing (MDFIC), mRNA sequence", Jan. 3, 2011. https://www.ncbi.nlm.nih.gov/nucest/66265111?report=genbank.
Gu et al., "Expression profile and differential regulation of the Human I-mfa domain-Containing protein (HIC) gene in Immune cells", Immunology Letters 123(2):179-184 (2009).
Salgado et al., "Characterization of host genetic expression patterns in HIV-infected individuals with divergent disease progression", Virology 411:103-112 (2011).
Yan et al., "Prediction of Multiple Infections After Severe Burn Trauma: A Prospective Cohort Study", Annals of Surgery 1-12 (2014).

* cited by examiner

*Primary Examiner* — Vanessa L. Ford
*Assistant Examiner* — Sandra E Dillahunt
(74) *Attorney, Agent, or Firm* — Nixon Peabody LLP; David S. Resnick; Nicole D. Kling

(57) ABSTRACT

The technology described herein is directed to the diagnosis, prognosis, and treatment of infection, e.g. after burn injury.

2 Claims, 11 Drawing Sheets

| SITE OF INFECTION | ORGANISM | GAP >= 2 DAY | GAP >= 7 DAY | COUNT AS AN EPISODE? |
|---|---|---|---|---|
| same | same | no | no | No |
| same | same | no | yes | Yes |
| same | same | yes | no | No |
| same | same | yes | yes | Yes |
| same | different | no | no | No |
| same | different | no | yes | Yes |
| same | different | yes | no | Yes |
| same | different | yes | yes | Yes |
| different | same | no | no | No |
| different | same | no | yes | Yes |
| different | same | yes | no | Yes |
| different | same | yes | yes | Yes |
| different | different | no | no | Yes |
| different | different | no | yes | Yes |
| different | different | yes | no | Yes |
| different | different | yes | yes | Yes |

RULES:
SAME SITE SAME ORG => 7 DAY RULE
SAME SITE DIFFERENT ORG => 2 DAY RULE
DIFFERENT SITE SAME ORG => 2 DAY RULE
DIFFERENT SITE DIFFERENT ORG => ALWAYS DIFFERENT

Multiple records of the same day and the same site belong to a record cluster, and they are evaluated simultaneously. Members of a cluster have equal status. Members of a cluster are considered maximum one independent episode. A waiting list is used to prevent re-occurring or persistent infection from being counted as independent episode. Once an independent episode is identified, the organism and site combination is put on a waiting list that prevents the records of the next 6 days with same combination from being considered as another episode.

*FIG. 11*

METHODS AND ASSAYS RELATING TO THE TREATMENT OF INFECTION

CROSS-REFERENCE TO RELATED APPLICATIONS

This application is a 35 U.S.C. § 371 National Phase Entry Application of International Application No. PCT/US2014/065444 filed Nov. 13, 2014, which designates the U.S. and claims benefit under 35 U.S.C. § 119(e) of U.S. Provisional Application No. 61/903,548 filed Nov. 13, 2013, the contents of which are incorporated herein by reference in their entirety.

GOVERNMENT SUPPORT

This invention was made with Government support under grant number W81XWH-12-2-0007 awarded by the Department of Defense. The Government has certain rights in the invention.

TECHNICAL FIELD

The technology described herein relates to the diagnosis, prognosis, and treatment of infection, e.g. following burn injury or inhalation injury.

BACKGROUND

Severe trauma, e.g., burn injury, can cause immunosuppression, predisposing patients to infections. Despite all medical improvements, infections remain a major cause of critical injury-related morbidity and mortality, and recurrent sepsis predisposes patients to multiple organ failure, lengthens hospital stays, and increases costs. Moreover, the rapid emergence of multi-(MDR) or pan-drug resistant (PDR) pathogens that cause highly problematic acute, persistent or relapsing infections pose a dire threat to healthcare, especially among trauma and surgical patients. Due to the paucity of novel anti-infectives in development, further improvement in patient care and treatment efficacy may rely heavily on optimizing existing strategies and promoting patients-tailored therapies. Presently available tests are directed to diagnosing existing cases of sepsis, rather than identifying patients who will develop such conditions.

SUMMARY

A successful personalized approach requires rigorous triaging: early and accurate identification of patients more susceptible to infections can help tailor the anti-infective treatments and especially to elaborate long-term treatment plan. As described herein, the inventors have identified a gene expression signature that accurate identifies the patients who will succumb to infection. The methods and assays described herein are demonstrated to be significantly more accurate than traditional clinical characteristic triaging.

In one aspect, described herein is an assay comprising: measuring the level of a gene expression product of at least one gene of Tables 4 and 5 a test sample obtained from a subject; wherein a decrease in the level of a gene expression product of Table 4 relative to a reference level indicates the subject has a higher risk of having or developing an infection and an increase in the level of a gene expression product of a gene of Table 5 relative to a reference level indicates the subject has a higher risk of having or developing an infection.

In one aspect, described herein is an assay comprising: contacting a sample obtained from a subject at risk of developing an infection with a probe to detect the level of a gene expression product of at least one gene of Tables 4 and 5; measuring the presence or intensity of a signal which indicates the presence or level of the gene expression product in the sample; wherein a decrease in the level of a gene expression product of a gene of Table 4 relative to a reference level indicates the subject has a higher risk of having or developing an infection and an increase in the level of a gene expression product of a gene of Table 5 relative to a reference level indicates the subject has a higher risk of having or developing an infection.

In one aspect, described herein is a method of identifying a subject in need of treatment for infection, the method comprising: measuring the level of a gene expression product of at least one gene of Tables 4 and 5 in a test sample obtained from a subject; and identifying the subject as being in need of treatment for infection when the level of a gene expression product of a gene of Table 4 is decreased relative to a reference level and the level of a gene expression product of a gene of Table 5 is increased relative to a reference level.

In one aspect, described herein is a method of determining if a subject is at risk for infection, the method comprising providing a sample obtained from the subject; measuring the level of a gene expression product of at least one gene of Tables 4 and 5 in the sample; comparing the level of the gene expression product in the sample to a reference level of the gene expression product; determining that the subject is at risk for infection when the level of a gene expression product of a gene of Table 4 is decreased relative to a reference level and the level of a gene expression product of a gene of Table 5 is increased relative to a reference level; and determining that the subject is not at risk for infection when the level of a gene expression product of a gene of Table 4 is not decreased relative to a reference level and the level of a gene expression product of a gene of Table 5 is not increased relative to a reference level.

In one aspect, described herein is a method of determining the efficacy of a treatment for infection, the method comprising: (a) measuring the level of a gene expression product of at least one gene of Tables 4 and 5 in a test sample obtained from a subject before administration of the treatment; (b) measuring the level of the gene expression product in a test sample obtained from a subject after administration of the treatment; and wherein the treatment is determined to be efficacious when the level of a gene expression product of a gene of Table 4 measured in step (b) is not decreased relative to the level measured in step (a) and the level of a gene expression product of a gene of Table 5 measured in step (b) is not increased relative to the level measured in step (a). In some embodiments, the treatment for infection is an anti-sepsis treatment.

In one aspect, described herein is a method of treatment for infection comprising; measuring the level of a gene expression product of at least one gene of Tables 4 and 5 in a test sample obtained from a subject; treating the subject with a treatment selected from the group consisting of: antibiotics; extended courses of antibiotics; immunotherapy; and LPS removal; when the level of a gene expression product of a gene of Table 4 is decreased relative to a reference level and the level of a gene expression product of a gene of Table 5 is increased relative to a reference level.

In one aspect, described herein is a method of treatment for infection comprising; administering a treatment selected from the group consisting of: antibiotics; extended courses of antibiotics; immunotherapy; and LPS removal; to a subject determined to have a level of a gene expression product of a gene of Table 4 that is decreased relative to a reference level or a level of a gene expression product of a gene of Table 5 that is increased relative to a reference level.

In some embodiments, the level of a gene expression product is determined by measuring the level of a nucleic acid. In some embodiments, the level of a gene expression product is determined by determined the level of a RNA transcript. In some embodiments, the level of the nucleic acid is determined using a method selected from the group consisting of: RT-PCR; quantitative RT-PCR; Northern blot; microarray based expression analysis; next-generation sequencing; and RNA in situ hybridization. In some embodiments, the level of a gene expression product is determined by measuring the level of a polypeptide. In some embodiments, the level of the polypeptide is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the polypeptide level is measured using immunochemistry. In some embodiments, the antibody reagent is detectably labeled or generates a detectable signal.

In some embodiments, the expression level is normalized relative to the expression level of one or more reference genes or reference proteins. In some embodiments, the expression level of a gene expression product of at least two genes of Tables 4 and 5 are measured. In some embodiments, the expression level of a gene expression product of at least three genes of Tables 4 and 5 are measured. In some embodiments, the expression level of a gene expression product of at least four genes of Tables 4 and 5 are measured. In some embodiments, the expression level of a gene expression product of at least five genes of Tables 4 and 5 are measured. In some embodiments, the expression level of a gene expression product of at least six genes of Tables 4 and 5 are measured.

In some embodiments, the genes are selected from the group consisting of: THBS1; ARHGEF7; MDFIC; CCND2; OSBPL8; DCAF7; TMEM50B; GOLGA8A and/or GOLGA8B; SMARCA4; WHSC1L1; LOC101928343; and L1NC00869. In some embodiments, the expression level of a gene expression product of THBS1; ARHGEF7; MDFIC; CCND2; OSBPL8; DCAF7; TMEM50B; GOLGA8A and/or GOLGA8B; SMARCA4; WHSC1L1; LOC101928343; and LINC00869 is measured.

In some embodiments, the expression level of a gene expression product of CCND2; THBS1; MDFIC; SMARCA4; WHSC1L1; TMEM50B; DCAF7; and OSBPL8 is measured. In some embodiments, the subject is at least 16 years of age or older.

In some embodiments, the expression level of a gene expression product of NFKB2; MAX; PDLIM5; GATAD2B; and ZSCAN30 is measured. In some embodiments, the subject is 15 years of age or younger.

In some embodiments, the sample comprises blood or plasma. In some embodiments, the sample comprises muscle tissue and the one or more genes are selected from the group consisting of: ALDH1A1; ALDHIA2; ALDH3B1; ALDH5A1; ALDH6A1; and ALDH7A1.

In some embodiments, the method or assay further comprises determining the values of total body surface area (TBSA) burns, age, and/or inhalation status; wherein an increase in any of the preceding values indicates an increased risk of the subject having or developing infection. In some embodiments, the method or assay further comprises multiplying each gene expression value measured, and optionally, the total body surface area (TBSA) burns, age, and/or inhalation status values, by a coefficient and adding the resulting products to yield a risk value. In some embodiments, a risk value of greater than the computed reference baseline coefficient value indicates the subject is at risk of having or developing infection and/or is in need of treatment for infection. In some embodiments, the coefficient is about the coefficient provided in Table 7. In some embodiments, a risk value of greater than about $-1.1912$ indicates the subject is at risk of having or developing infection and/or is in need of treatment for infection.

In some embodiments, the infection comprises a microbe selected from the group consisting of: Gram-negative bacteria; *Staphylococcus* spp.; *Staphylococcus aureus*; coagulase-negative Staphylococci; *Enterococcus* spp.; *Candida* spp. *Escherichia coli*; *Enterobacter* spp.; *Klebsiella pneumonia*; *Acinetobacter* spp.; *Pseudomonas aeruginosa*; *Streptococcus pneumonia*; *Streptococcus viridans*; Gram-positive bacteria; *Serratia marcescens*; *Hemophilus influenza*; *Stenotrophomonas* spp.; *Proteus*; *Aspergillus*; *Neisseria*; *Clostridium* sp.; *Bacteroides* sp; fungi; cytomegalovirus; and herpes virii. In some embodiments, the subject at risk of infection is a subject at risk of a condition selected from the group consisting of: multiple infection episodes; sepsis; pneumonia; urinary tract infection; blood stream infection; catheter-related infection; and wound infection. In some embodiments, the subject at risk of infection is a subject having or diagnosed as having a condition selected from the group consisting of a burn injury; inhalation injury; immunosuppression; major surgical procedures; intubation or catheters; blunt trauma; penetrating trauma; burn trauma; diabetes; diabetic infection complications; HIV; or is a subject in the intensive care unit and with central lines. In some embodiments, the method or assay further comprises the step of detecting the presence of susceptibility-associated SNPs or pathogen markers in the sample obtained from the subject.

In one aspect, described herein is a kit for performing the methods and/or assays described herein.

In one aspect, described herein is a computer system for determining the risk of a subject having or developing an infection, the system comprising: a measuring module configured to measure the level of a gene expression product of at least one gene of Tables 4 and 5 in a test sample obtained from a subject; a storage module configured to store output data from the determination module; a comparison module adapted to compare the data stored on the storage module with a reference level, and to provide a retrieved content, and a display module for displaying whether the sample comprises a level of the gene expression product which is significantly different relative to the reference expression level and/or displaying the relative level of the gene expression product. In some embodiments, the system further comprises an output module for reporting/displaying the probability of a subject developing infections. In some embodiments, the probablility is calculated from the input from the measuring module and clinical parameters. In some embodiments, the probability is calculated with at least a 95% confidence interval. In some embodiments, the measuring module measures the intensity of a detectable signal from an assay indicating the level of a polypeptide in the test sample. In some embodiments, the assay is an immunoassay. In some embodiments, the measuring module measures the intensity of a detectable signal from a RT-PCR assay indicating the level of a RNA transcript in the test sample. In some embodiments, if the computing module determines that the level of the gene expression product in the test sample obtained from a subject differs by a statistically significant amount from the reference level, the display module displays a signal indicating that the levels in the sample obtained from a subject are different than those of the reference level. In some embodiments, the signal indicates that the subject has an increased likelihood of having or developing an infection. In some embodiments, the signal indicates the subject is in need of treatment for an infection. In some embodiments, the signal indicates the degree to which the level of the gene expression product in the sample obtained from a subject varies from the reference level.

BRIEF DESCRIPTION OF THE DRAWINGS

FIG. 2A depicts the types of infection. One case of pseudomembranous colitis represents 0.2%. FIG. 2B depicts the percentage of isolated pathogens among all infection records.

FIG. 3A depicts a representative repetition of 10-fold CV LASSO that chose 14 probe sets at $\lambda_{lse}$. The first vertical dotted line corresponds to the $\lambda_{min}$ that minimized binomial deviance during CV. The second dotted line corresponds to $\lambda_{lse}$, used for the selection of 14 probe sets as shown in FIG. 3B. FIG. 3B depicts LASSO coefficient profile plot of the coefficient paths. At $\lambda_{lse}$, as shown with the dotted line, 14 probe sets have their coefficients significantly different from zero and thus were chosen as part of the biomarker panel.

FIG. 11 depicts an infection episode decision table. Alternative presentation of the decision tree, complementary to FIG. 9B.

DETAILED DESCRIPTION

Figure 1:
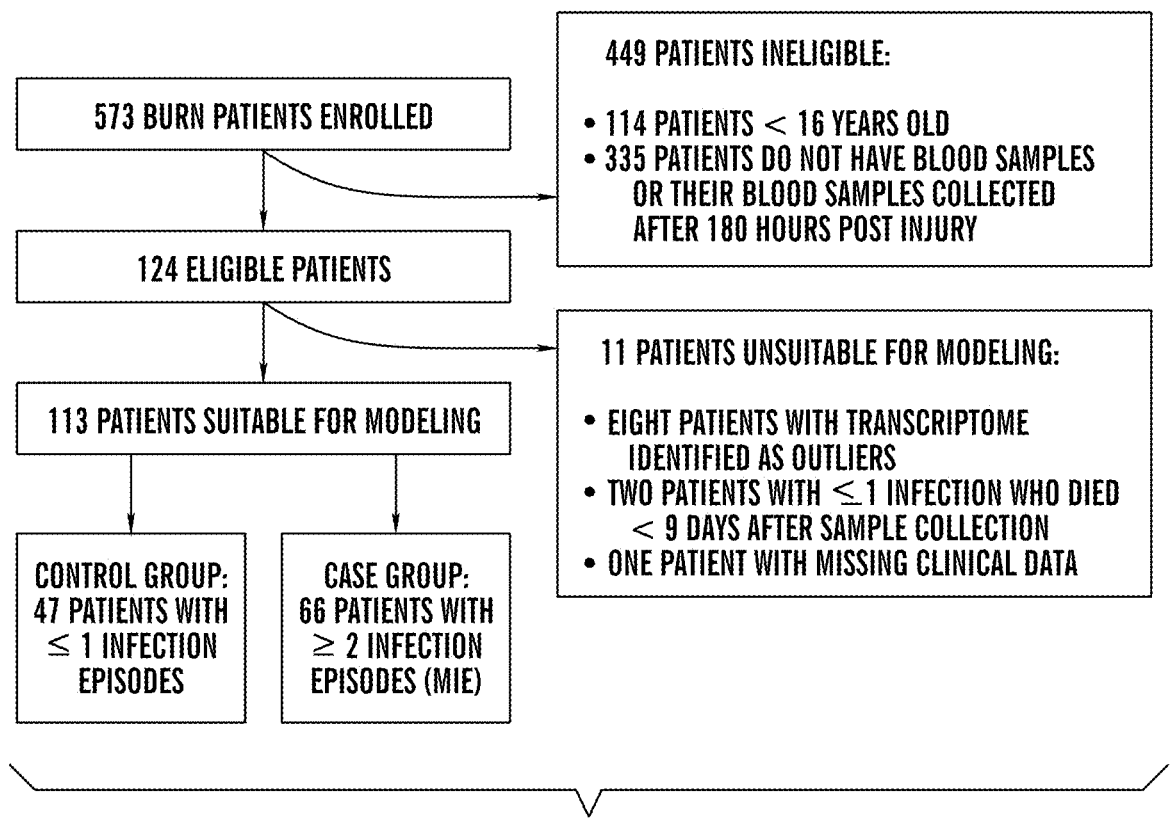
FIG. 1 depicts a diagram of the sample selection process, demonstrating the development of predictive models and discovery of biomarkers.

As described herein, the inventors have identified a gene expression signature that is indicative of hypersusceptibility to infection, e.g. in burn victims. Detection of abnormal levels of expression of one or more of the marker genes described herein permits the identification of patients, with high accuracy, who will succumb to infection, particularly multiple infections. The methods described herein are demonstrated to have significantly greater predictive power than ethods utilizing traditional clinical parameters. Accordingly, provided herein are methods and assay relating to the prognosis and treatment of subjects at risk of infection.

As described herein, the inventors have identified certain genes which are upregulated or downregulated to a statistically significant degree in subjects which are at increased risk of, e.g., likely to, experience infection, including multiple infection events. Herein, these genes are referred to as marker genes to indicate their relation to being a marker for this hypersusceptibility. Accordingly, some embodiments of the invention are generally related to assays, methods and systems for assessing the risk of a subject having and/or developing infection(s).

In one aspect, described herein is an assay comprising: measuring the level of a gene expression product of at least one gene of Tables 4 and 5 a test sample obtained from a subject; wherein a decrease in the level of a gene expression product of a gene of Table 4 relative to a reference level indicates the subject has a higher risk of having or developing an infection and an increase in the level of a gene expression product of a gene of Table 5 relative to a reference level indicates the subject has a higher risk of having or developing an infection. In one aspect, described herein is an assay comprising: contacting a sample obtained from a subject at risk of developing an infection with a probe to detect the level of a gene expression product of at least one gene of Tables 4 and 5; measuring the presence or intensity of a signal which indicates the presence or level of the gene expression product in the sample; wherein a decrease in the level of a gene expression product of a gene of Table 4 relative to a reference level indicates the subject has a higher risk of having or developing an infection and an increase in the level of a gene expression product of a gene of Table 5 relative to a reference level indicates the subject has a higher risk of having or developing an infection. In one aspect, described herein is a method of identifying a subject in need of treatment for infection, the method comprising: measuring the level of a gene expression product of at least one gene of Tables 4 and 5 in a test sample obtained from a subject; and identifying the subject as being in need of treatment for infection when the level of a gene expression product of a gene of Table 4 is decreased relative to a reference level and the level of a gene expression product of a gene of Table 5 is increased relative to a reference level. In one aspect, described herein is a method of determining if a subject is at risk for infection, the method comprising: providing a sample obtained from the subject; measuring the level of a gene expression product of at least one gene of Tables 4 and 5 in the sample; comparing the level of the gene expression product in the sample to a reference level of the gene expression product; determining that the subject is at risk for infection when the level of a gene expression product of a gene of Table 4 is decreased relative to a reference level and the level of a gene expression product of a gene of Table 5 is increased relative to a reference level; and determining that the subject is not at risk for infection when the level of a gene expression product of a gene of Table 4 is not decreased relative to a reference level and the level of a gene expression product of a gene of Table 5 is not increased relative to a reference level.

In one aspect, described herein is a method of determining the efficacy of a treatment for infection, the method comprising: (a) measuring the level of a gene expression product of at least one gene of Tables 4 and 5 in a test sample obtained from a subject before administration of the treatment; (b) measuring the level of the gene expression product in a test sample obtained from a subject after administration of the treatment; and (c) determining that the treatment is effective when the level of a gene expression product of a gene of Table 4 measured in step (b) is not decreased relative to the level measured in step (a) and the level of a gene expression product of a gene of Table 5 measured in step (b) is not increased relative to the level measured in step (a). In some embodiments, the treatment for infection is an antisepsis treatment.

In one aspect, described herein is a method of treatment for infection comprising; measuring the level of a gene expression product of at least one gene of Tables 4 and 5 in a test sample obtained from a subject; treating the subject with a treatment selected from the group consisting of: antibiotics; extended courses of antibiotics; immunotherapy; and LPS removal; when the level of a gene expression product of a gene of Table 4 is decreased relative to a reference level and the level of a gene expression product of a gene of Table 5 is increased relative to a reference level. In one aspect, described herein is a method of treatment for infection comprising; administering a treatment selected from the group consisting of: antibiotics; extended courses of antibiotics; immunotherapy; and LPS removal; to a subject determined to have a level of a gene expression product of a gene of Table 4 that is decreased relative to a reference level or a level of a gene expression product of a gene of Table 5 that is increased relative to a reference level.

In some embodiments of any aspect described herein, the subject in need of treatment for infection and/or identified as being at risk of having or developing infection, is a subject in need of treatment for multiple infections and/or identified as being at risk of having or developing multiple infections. As used herein, "multiple infections" can refer to either infection with multiple organisms or multiple episodes of infection (e.g. with the same or different microbes). In some embodiments of any aspect described herein, the subject in need of treatment for infection and/or identified as being at risk of having or developing infection, is a subject in need of treatment for multiple infection episodes and/or identified as being at risk of having or developing multiple infection episodes. Non-limiting examples of microbes that can cause and/or contribute to an infection as described herein can include Gram-negative bacteria; *Staphylococcus* spp.; *Staphylococcus aureus*; coagulase-negative *Staphylococci*; *Enterococcus* spp.; *Candida* spp. *Escherichia coli*; *Enterobacter* spp.; *Klebsiella pneumonia*; *Acinetobacter* spp.; *Pseudomonas aeruginosa*; *Streptococcus pneumonia*; *Streptococcus viridans*; Gram-positive bacteria; *Serratia marcescens*; *Hemophilus influenza*; *Stenotrophomonas* spp.; *Proteus*; *Aspergillus*; *Neisseria*; *Clostridium* sp.; *Bacteroides* sp; fungi; cytomegalovirus; and herpes virii.

In certain embodiments the assays, methods, and systems are directed to determination and/or measurement of the expression level of a gene product of at least two genes in a biological sample of a subject, i.e. at least two genes, at least three genes, at least four genes, at least five genes, at least six genes, at least seven genes, at least eight genes, or more genes, or any number of genes selected from any in a combination of Table 4 and Table 5 as described herein. In some embodiments, one looks at a group of genes where some increase in expression and others decrease in expression. In some embodiments, the expression level of a gene product of the same number of genes from each of Tables 4 and 5 is determined, e.g. two genes from each table. In some embodiments, the expression level of a gene product of different numbers of genes from each of Tables 1 and 2 is determined, e.g. two genes from Table 4 and two genes from Table 5 or 1 gene from Table 4 and 2 genes from Table 5. In some embodiments, the expression level overall for the group shows a pattern change, i.e. some genes overexpress, some underexpress. In some embodiments, the overall change is statistically significant.

TABLE 4

Infection Susceptibility Marker Genes which are Downregulated in Subjects with increased susceptibility to infection

| Gene | NCBI Reference No: |
|---|---|
| MDFIC | 29969 |
| CCND2 | 894 |
| OSBPL8 | 114882 |
| DCAF7 | 10238 |
| TMEM50B | 757 |
| GOLGA8A | 23015 |
| GOLGA8B | 440270 |
| SMARCA4 | 6597 |
| WHSC1L1 | 54904 |
| LOC101928343 | 101928343 |
| LINC00869 | 57234 |
| PDLIM5 | 10611 |
| GATAD2B | 57459 |
| ZSCAN30 | 100101467 |
| ALDH1A1 | 216 |
| ALDH1A2 | 8854 |
| ALDH5A1 | 7915 |
| ALDH6A1 | 4329 |
| ALDH7A1 | 501 |

TABLE 5

Infection Susceptibility Marker Genes which are Upregulated in Subjects with increased susceptibility to infection

| Gene | NCBI Reference No: |
|---|---|
| THBS1 | 7057 |
| ARHGEF7 | 8874 |
| NFKB2 | 4791 |
| MAX | 4149 |
| ALDH3B1 | 221 |

The gene names listed in Tables 4 and 5 are common names. NCBI Gene ID numbers for each of the genes listed in Tables 4 and 5 can be obtained for a number of species by searching the "Gene" Database of the NCBI (available on the World Wide Web at ncbi.nlm.nih.gov/) using the common name as the query and selecting the first returned gene for the desired species. The NCBI Reference numbers provided in Tables 4 and 5 are those for the *Homo sapiens* genes.

In subjects at risk of having or developing infection and/or in need of treatment for infection, the marker genes listed in Table 4 can be downregulated and those in Table 5 can be upregulated, e.g. for marker genes listed in Table 4, if the measured marker gene expression in a subject is lower as compared to a reference level of that marker gene's expression, then the subject is identified as having an increased risk of having and/or developing infection and/or being in need of treatment for infection. Likewise, for marker genes listed in Table 5, if the measured marker gene expression in a subject is higher by as compared to a reference level of that marker gene's expression, then the subject is identified as having an increased risk of having and/or developing infection and/or being in need of treatment for infection. In some embodiments, one looks at a statistically significant change. However, even if a few genes in a group do not differ from normal, a subject can be identified as having an increased risk of having and/or developing infection and/or being in need of treatment for infection if the overall change of the group shows a significant change, preferably a statistically significant change.

In certain embodiments marker genes in Table 5 are upregulated in subjects having an increased risk of having and/or developing infection and/or being in need of treatment for infection. If the level of a gene expression product of a marker gene in Table 5 is higher than a reference level of that marker gene, the subject is more likely to have an increased risk of having and/or developing infection and/or be in need of treatment for infection. The level of a gene expression product of a marker gene in Table 5 which is higher than a reference level of that marker gene by at least about 10% than the reference amount, at least about 20%, at least about 30%, at least about 40%, at least about 50%, at least about 80%, at least about 100%, at least about 200%, at least about 300%, at least about 500% or at least about 1000% or more, is indicative that the subject has an increased risk of having and/or developing infection and/or is in need of treatment for infection.

In certain embodiments marker genes in Table 4 are downregulated in subjects having an increased risk of having and/or developing infection and/or being in need of treatment for infection. If the level of a gene expression product of a marker gene in Table 4 is less than a reference level of that marker gene, the subject is more likely to have an increased risk of having and/or developing infection and/or be in need of treatment for infection. The level of a gene expression product of a marker gene in Table 4 which is lower than a reference level of that marker gene by at least about 10% than the reference amount, at least about 20%, at least about 30%, at least about 40%, at least about 50%, at least about 60%, at least about 70%, at least about 80%, at least about 90%, or at least about 95%, about 98%, about 99% or 100%, including all the percentages between 10-100% is indicative that the subject has an increased risk of having and/or developing infection and/or is in need of treatment for infection.

In certain embodiments a subject is indicated to have an increased risk of having and/or developing infection and/or be in need of treatment for infection. if the expression level of one or more marker genes in a sample obtained from a subject differs from the expression level in a reference sample by a statistically significant amount.

In some embodiments, the expression level of a gene expression product of at least two genes of Tables 4 and 5 are measured. In some embodiments, the expression level of a gene expression product of at least three genes of Tables 4 and 5 are measured. In some embodiments, the expression level of a gene expression product of at least four genes of Tables 4 and 5 are measured. In some embodiments, the expression level of a gene expression product of at least five genes of Tables 4 and 5 are measured. In some embodiments, the expression level of a gene expression product of at least six genes of Tables 4 and 5 are measured. In some embodiments, the expression level of a gene expression product of at least seven genes of Tables 4 and 5 are measured. In some embodiments, the expression level of a gene expression product of at least eight genes of Tables 4 and 5 are measured. In some embodiments, the expression level of a gene expression product of at least nine genes of Tables 4 and 5 are measured. In some embodiments, the expression level of a gene expression product of at least ten genes of Tables 4 and 5 are measured.

In some embodiments, the level of a gene expression product of at least one gene selected from the group consisting of: THBS1; ARHGEF7; MDFIC; CCND2; OSBPL8; DCAF7; TMEM50B; GOLGA8A and/or GOLGA8B; SMARCA4; WHSC1L1; LOC101928343; and L1NC00869. In some embodiments, the level of a gene expression product of each of THBS1; ARHGEF7; MDFIC; CCND2; OSBPL8; DCAF7; TMEM50B; GOLGA8A and/or GOLGA8B; SMARCA4; WHSC1L1; LOC101928343; and LINC00869 is measured. In some embodiments, the sample is a blood or plasma sample.

In some embodiments, the level of a gene expression product of at least one gene selected from the group consisting of: CCND2; THBS1; MDFIC; SMARCA4; WHSC1L1; TMEM50B; DCAF7; and OSBPL8 is measured. In some embodiments, the level of a gene expression product of each of CCND2; THBS1; MDFIC; SMARCA4; WHSC1L1; TMEM50B; DCAF7; and OSBPL8 is measured. In some embodiments, the sample is a blood or plasma sample. In some embodiments, the subject is at least 16 years of age or older.

In some embodiments, the level of a gene expression product of at least one gene selected from the group consisting of: NFKB2; MAX; PDLIM5; GATAD2B; and ZSCAN30 is measured. In some embodiments, the level of a gene expression product of each of NFKB2; MAX; PDLIM5; GATAD2B; and ZSCAN30 is measured. In some embodiments, the sample is a blood or plasma sample. In some embodiments, the subject is 15 years of age or younger.

In some embodiments, the level of a gene expression product of at least one gene selected from the group consisting of: ALDH1A1; ALDH1A2; ALDH3B1; ALDH5A1; ALDH6A1; and ALDH7A1 is measured. In some embodiments, the level of a gene expression product of each of ALDH1A1; ALDH1A2; ALDH3B1; ALDH5A1; ALDH6A1; and ALDH7A1 is measured. In some embodiments, the sample is a muscle sample.

In some embodiments of any of the aspects described herein, information on the Total Body Surface Area (TBSA) burns, age and inhalation status (yes or no) can also be used in conjunction with the gene panel(s) described herein to improve prognosis and/or treatment. In one aspect, the assay or method can further comprise determining the values of total body surface area (TBSA) burns, age, and/or inhalation status; wherein an increase in any of the preceding values indicates an increased risk of the subject having or developing infection. One of skill in the art can readily determine such values, e.g., as part of a physical examination and/or triage process.

In some embodiments of the various aspects described herein, the assay or method can further comprise multiplying each gene expression value measured, and optionally, the total body surface area (TBSA) burns, age, and/or inhalation status values, by a coefficient and adding the resulting products to yield a risk value. Such coefficients adjust the various values to reflect their relative predictive weight and/or provide a risk value that falls upon a desired scale (e.g. 1 to 10). As used herein "risk value" refers to a value calculated by adding two or more gene expression values, and optionally, the total body surface area (TBSA) burns, age, and/or inhalation status values. In some embodiments, the values can first be multiplied by coefficients before the addition step.

In some embodiments, the coefficient can be about the coefficient value given for a particular value in Table 7. In some embodiments, a risk value of greater than about −1.1912 indicates the subject is at risk of having or developing infection and/or is in need of treatment for infection. This baseline coefficient is equal to zero for all the values, e.g., meaning that the population of the baseline was someone age 0, TBSA 0, no inhal, and 0 expression value for all the genes.

In some embodiments, the methods and assays described herein include (a) transforming the gene expression product into a detectable gene target; (b) measuring the amount of the detectable gene target; and (c) comparing the amount of the detectable gene target to an amount of a reference, wherein if the amount of the detectable gene target is statistically different from that of the amount of the reference level, the subject is identified as having an increased risk of having and/or developing infection and/or being in need of treatment for infection. As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Transformation, measurement, and/or detection of a target molecule, e.g. a mRNA or polypeptide of a gene of Tables 4 or 5 can comprise contacting a sample obtained from a subject with a reagent (e.g. a detection reagent) which is specific for the target, e.g., a TMEM50B-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure gene expression products are well known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for TMEM50B are commercially available and can be used for the purposes of the invention to measure protein expression levels, e.g. anti-TMEM50B (Cat. No. ab107741; Abcam, Cambridge Mass.). Alternatively, since the amino acid sequences for the marker genes are known and publically available at NCBI website, one of skill in the art can raise their own antibodies against these polypeptides of interest for the purpose of the invention. The amino acid sequences of the polypeptides described herein, have been assigned NCBI accession numbers for different species such as human, mouse and rat.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5% tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments, the level of, e.g., TMEM50B, can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In certain embodiments, the gene expression products as described herein can be instead determined by determining the level of messenger RNA (mRNA) expression of the genes described herein, e.g. a marker gene of Table 4 or 5. Such molecules can be isolated, derived, or amplified from a biological sample, such as a blood sample. Techniques for the detection of mRNA expression are known by persons skilled in the art, and can include but not limited to, PCR procedures, RT-PCR, quantitative RT-PCR Northern blot analysis, differential gene expression, RNA protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., the marker genes of Tables 4 or 5, have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfluorescein (commonly known by the abbreviations FAM and F), 6-carboxy-2',4', 7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

A level which is greater than a reference level can be a level which is greater by at least about 10%, at least about 20%, at least about 50%, at least about 100%, at least about 200%, at least about 300%, at least about 500%, at least about 1000%, or greater than the reference level. In some embodiments, a level which is greater than a reference level can be a level which is statistically significantly greater than the reference level. A level which is less than a reference level can be a level which is lower by at least about 10%, at least about 20%, at least about 50%, at least about 60%, at least about 70%, at least about 80%, at least about 90%, or less of the reference level. In some embodiments, a level which is less than a reference level can be a level which is statistically significantly less than the reference level.

In some embodiments, the reference can be a level of expression of the marker gene product in a normal healthy subject with no symptoms or signs of infection. For example, a normal healthy subject has no burn injury, no signs and/or symptoms of immunosuppression, no inhalation injury, and no detectable presence of a pathogen in the bloodstream. In some embodiments, the reference can also be a level of expression of the marker gene product in a control sample, a pooled sample of control individuals or a numeric value or range of values based on the same.

In some embodiments, the reference can be a level of a marker gene in a population of subjects who do not have or are not diagnosed as having, and/or do not exhibit signs or symptoms of infection and/or are not at risk of infection (e.g., they do not have a burn injury, immunosuppression, and/or inhalation injury). In some embodiments, the reference can also be a level of expression of a marker gene in a control sample, a pooled sample of control individuals or a numeric value or range of values based on the same. In some embodiments, the reference can be the level of a marker gene in a sample obtained from the same subject at an earlier point in time, e.g., the methods described herein can be used to determine if a subject's risk or likelihood of developing infection is increasing.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) infection, burn injury, immunosuppression, and/or inhalation injury. In some embodiments, the subject at risk of infection can be a subject at risk of multiple infection episodes, sepsis, and/or pneumonia. Additional non-limiting examples of subjects at risk of infection can include, patients who need major surgical procedures, patients with intubation or catheters, patients in the intensive care unit and with central lines, patients with blunt and penetrating trauma, patients with burn trauma, patients with diabetes and having diabetes foot and other infection complications, HIV patients and other conditions resulting in immunosuppression ie. cancer patients undergoing treatments, bone marrow transplants, transfusions, organ grafts.

The term "sample" or "test sample" as used herein denotes a sample taken or isolated from a biological organism, e.g., a blood or plasma sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, the test sample can be a blood sample. In some embodiments, the test sample can be a plasma sample.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In certain embodiments, the subject may be exhibiting a sign or symptom of, e.g. burn injury, immunosuppression, and/or inhalation injury.

In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments of the various aspects, the expression level of a given gene, e.g., a marker gene of Table 4 or 5, can be normalized relative to the expression level of one or more reference genes or reference proteins, e.g. the expression level of a housekeeping gene.

In some embodiments of any of the various aspects, the method can further comprise a step of generating a report based on the detection of the one or more marker gene expression levels.

In some embodiments of any of the various aspects, the assay or method can further comprise the step of detecting the presence of susceptibility-associated SNPs or pathogen markers in the sample obtained from the subject. Susceptibility-associated SNPs and pathogen markers are well known in the art. See, e.g., for further discussion Netea M G, et al. *Nature Immunology*. 2012; 13:535-542; Bronkhorst MWGA, et al. *British Journal of Surgery*. 2013; 100:1818-1826; Jannes G, and De Vos D. *Methods Mol Biol*. 2006; 345:1-21; Pirnay J-P, et al. *Crit Care*. 2000; 4:255; Chang S-S, et al. *PLoS One*. 2013; 8:e62323; and Skvarc M, et al. *Eur J Microbiol Immunol (Bp)*. 2013; 3:97-104; each of which is incorporated by reference herein in its entirety.

In some embodiments, the methods described herein relate to treating a subject having or diagnosed as having, e.g. burn injury, inhalation injury, or immunosuppression with a treatment for infection.

Subjects having burn injury can be identified by a physician using current methods of diagnosing burn injury. Symptoms and/or complications of burn injury which characterize these conditions and aid in diagnosis are well known in the art and include but are not limited to, pain, redness, blisters, and discoloration. A burn can be caused by, e.g., heat, friction, radiation, chemical exposure, or electrical exposure.

Subjects having inhalation injury can be identified by a physician using current methods of diagnosing inhalation injury. As used herein, "inhalation injury" refers to damage to the airways and/lungs by irritants and/or toxins in the air. Symptoms and/or complications of inhalation injury which characterize these conditions and aid in diagnosis are well known in the art and include but are not limited to, inflammation, hypoxia, and edema. Inhalation injury can be caused by, e.g., smoke, thermal injury, chlorine, phosgene, ammonia, sulfur mustard, chloramine, mustard gas, methyl isocyanate, and the like.

Subjects having immunosuppression can be identified by a physician using current methods of diagnosing immunosuppression. As used herein, "immunosuppression" refers to impairment of any component of cellular and/or humoral immunity. Symptoms and/or complications of immunosuppression which characterize these conditions and aid in diagnosis are well known in the art and include but are not limited to, fever, swelling, reduce urine output, infection, and the like. Tests that may aid in a diagnosis of, e.g. immunosuppression include, but are not limited to, assays of lymphocyte function, lymphocyte proliferation and expression of T cell surface antigens. Immunosuppression can be caused by, e.g., burn injury, inhalation injury, tumors, transplantation, HIV/AIDS, chemotherapy, or administration of immunosuppressants.

The compositions and methods described herein can be administered to a subject at increased risk of having or developing an infection. In some embodiments, the methods described herein comprise administering an effective amount of compositions described herein, to a subject in order to alleviate a symptom of infection. As used herein, "alleviating a symptom of an infection" is ameliorating any condition or symptom associated with the infection. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection, or administration. Administration can be local or systemic.

The term "effective amount" as used herein refers to the amount of a treatment needed to alleviate at least one or more symptom of the disease or disorder, and relates to a sufficient amount of pharmacological composition to provide the desired effect. The term "therapeutically effective amount" therefore refers to an amount of a treatment that is sufficient to provide a particular anti-infective effect when administered to a typical subject. An effective amount as used herein, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bacterial titers, or the levels of marker genes as described herein, among others. The dosage can be determined by a physician and adjusted, as necessary, to suit observed effects of the treatment.

A number of treatments are know in the art for infection, e.g. for those at risk of infection or at risk of multiple infections. Non-limiting examples of such treatments can include anti-infectives; antibiotics; extended courses of antibiotics; immunotherapy; and LPS removal.

Anti-infective agents can include, for example, anti-viral and anti-fungal agents as well as agents for the treatment of parasitical infections. Exemplary anti-fungal agents can include, but are not limited to polyenes (e.g. amphotericin B; candicidin; fillipin, hamycin; natamycin; nystatin; and rimocidin), imidazoles (e.g., bifonazole; fentifconzaole; ketoconazole; etc), triazoles (e.g. albaconazole; fluconazole; ravuconazole; voriconazole, etc.), thiazoles (e.g. abafungin), allylamines (e.g. amorolfin; butenafine; naftifine; terbinafine), and echinocandins (e.g. anidulafungin; caspofungin; and micfungin). Exemplary anti-viral agents can include, but are not limited to: anti-VAP antibodies; amantadine; rimantadine; pleconaril; acyclovir; zidovudine; lamivudine; and fomivirsen. Additional non-limiting examples of anti-infect agent can include antioxidant therapies, e.g, Vitamin C, vitamin E, zinc, selenium, co-enzyme Q or other antioxidants supplements.

The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like.

In some embodiments, a subject determined to be at risk of having or developing an infection (e.g. multiple infections) can be administered an extended course of antibiotics. An extended course of antibiotics can comprise administering the antibiotics before symptoms of infection are detected, administering multiple antibiotics, and/or administering antibiotics for a longer period of time than is standard for the particular formulation(s) being used.

As used herein, the term "immunotherapy" refers to the treatment of a subject with an agent that modulates the immune system, e.g. an antigen, adjuvant, immune system regulatory molecule, and/or antibody or antibody-based therapeutic. Exemplary immunotherapy agents include cytokines, IL-7, IL-2, IFN-gamma, and vaccines.

A further example of treatment for infection can comprise LPS removal, e.g., treating a subject's blood and/or plasma to reduce the level of active endotoxins (e.g. LPS) present in the blood and/or plasma. The endotoxins can be physically removed from the blood or neutralized without physically removing them.

In one aspect, described herein is a kit for performing any of the assays and/or methods described herein. In some embodiments, the kit can comprise a reagent specific for a gene expression product of one of the marker genes of Tables 4 or 5.

A kit is any manufacture (e.g., a package or container) comprising at least one reagent, e.g., an antibody reagent(s) or nucleic acid probe, for specifically detecting, e.g., a marker gene expression product or fragment thereof, the manufacture being promoted, distributed, or sold as a unit for performing the methods or assays described herein. When the kits, and methods described herein are used for diagnosis and/or treatment of infection, the reagents (e.g., detection probes) or systems can be selected such that a positive result is obtained in at least about 20%, at least about 40%, at least about 60%, at least about 80%, at least about 90%, at least about 95%, at least about 99% or in 100% of subjects who have or will develop infection.

In some embodiments, described herein is a kit for the detection of a marker gene expression product (e.g., a gene expression product of a gene of Table 4 or 5) in a sample, the kit comprising at least a first specific reagent as described herein which specifically binds the expression product, on a solid support and comprising a detectable label. The kits described herein include reagents and/or components that permit assaying the level of an expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g., a polypeptide) in a sample, e.g. a plasma sample. Thus, ultrafiltration devices permitting, e.g., protein concentration from plasma can also be included as a kit component.

Preferably, a diagnostic or prognostic kit for use with the methods and assays disclosed herein contains detection reagents for marker expression products. Such detection reagents comprise in addition to marker gene-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of an expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

In some aspects, the invention described herein is directed to systems (and computer readable media for causing computer systems) for obtaining data from at least one sample obtained from at least one subject, the system comprising 1) a measuring module configured to receive the at least one sample and perform at least one analysis on the at least one sample to determine the level of a gene expression product of at least one marker gene of Table 4 or 5 in the sample; 2) a storage device configured to store data output from the determination module; and 3) a display module for displaying a content based in part on the data output from the determination module, wherein the content comprises a signal indicative of the level of the gene expression product.

Figure 6:
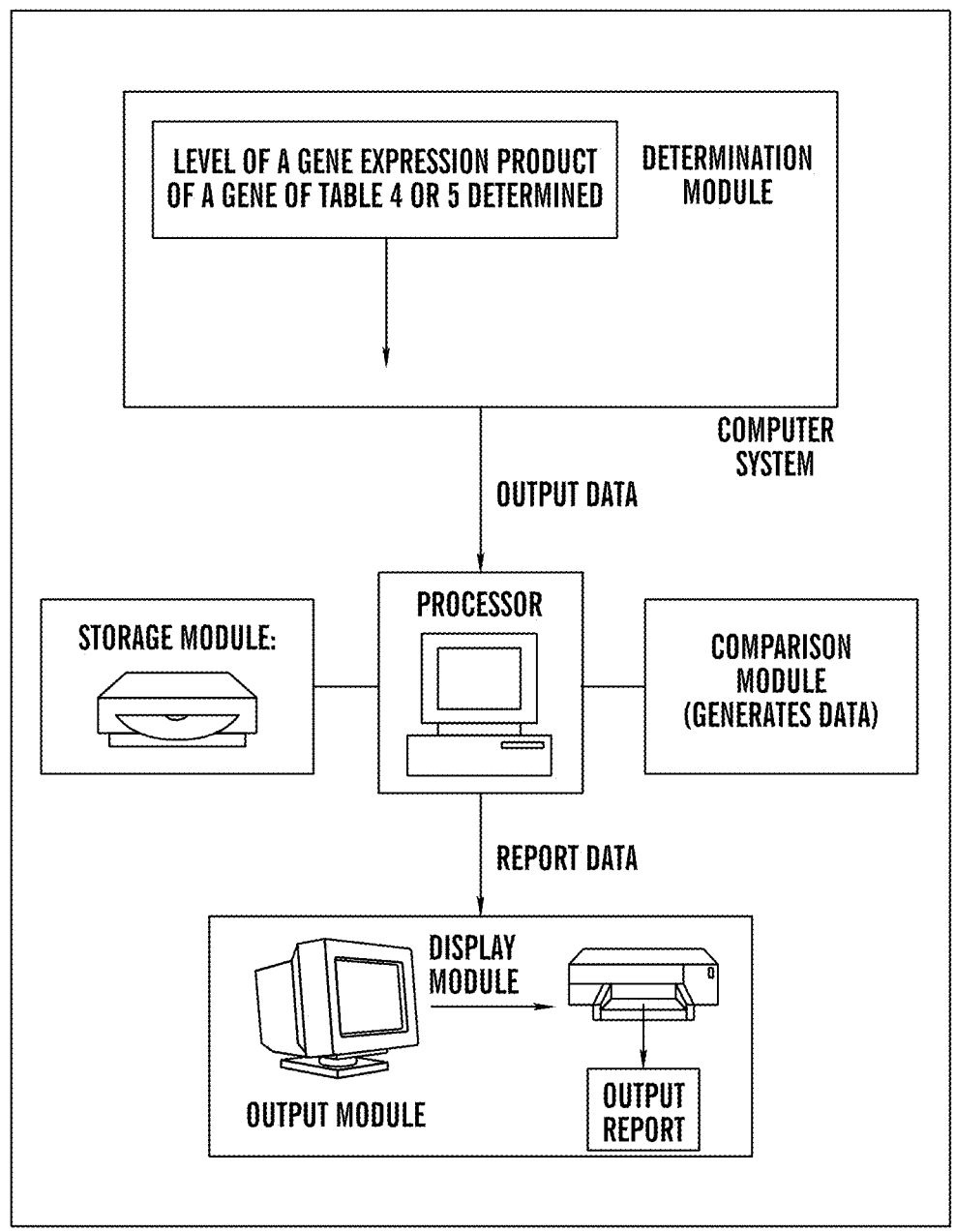
FIG. 6 is a diagram of an exemplary embodiment of a system for performing an assay for determining the level of a gene expression product in a sample obtained from a subject.

In one embodiment, provided herein is a system comprising: (a) at least one memory containing at least one computer program adapted to control the operation of the computer system to implement a method that includes a measuring module configured to measure the level of a gene expression product of at least one marker gene of Table 4 or 5 in a test sample obtained from a subject; a storage module configured to store output data from the determination module; a comparison module adapted to compare the data stored on the storage module with a reference level, and to provide a retrieved content, and a display module for displaying whether the sample comprises a level of gene expression product which is significantly increased different (e.g. greater or less) than the reference expression level and/or displaying the relative level of the gene expression product and (b) at least one processor for executing the computer program (see FIG. 6).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; a tablet; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, R, SAS, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of expression products etc in computer readable form.

The measuring module can comprise any system for detecting a signal elicited from an assay to determine the level of a gene expression product as described above herein. In some embodiments, such systems can include an instrument, e.g., AU2700 (Beckman Coulter Brea, Calif.) as described herein for quantitative measurement of polypeptides or e.g., a real time PCR machine, e.g. a LIGHTCYCLER™ (Roche). In some embodiments, the measuring module can measure the intensity of a detectable signal from an assay indicating the level of a marker gene polypeptide in the test sample. In some embodiments, the assay can be an immunoassay. In some embodiments, the measuring module can measure the intensity of a detectable signal from a RT-PCR assay indicating the level of a marker gene RNA transcript in the test sample.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of marker gene expression products in healthy subjects and/or a population of healthy subjects.

Figure 7:
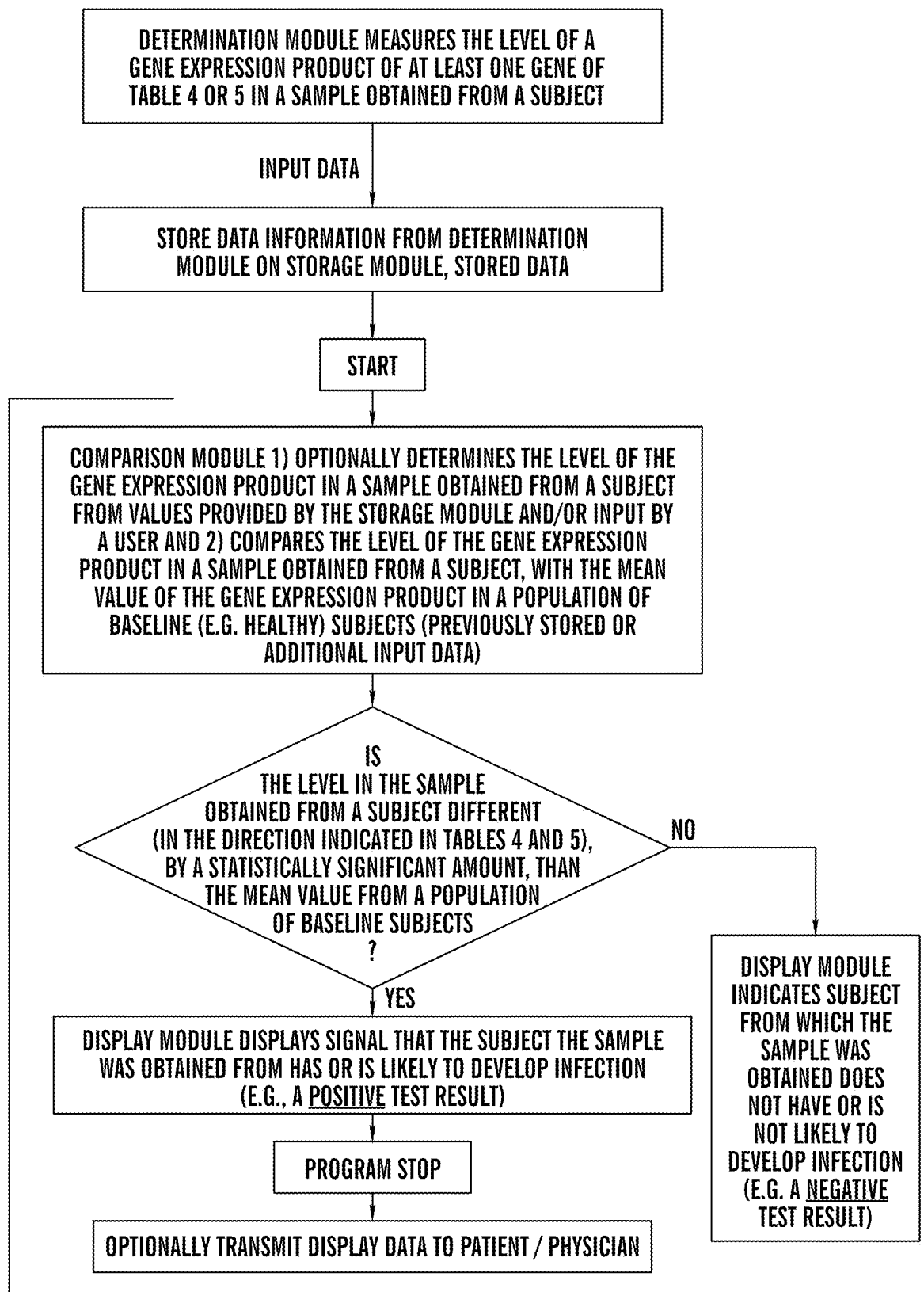
FIG. 7 is a diagram of an exemplary embodiment of an embodiment of a comparison module as described herein. The comparison module depicted in FIG. 7 provides a binary (negative or positive) result. In certain embodiments of the various aspects described herein, the comparison module can provide a probability, e.g. a continuous variable between 0 and 1, rather than merely a binary outcome.

The "computing module" can use a variety of available software programs and formats for computing the level of a gene expression product. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of a gene expression product in a sample obtained from a subject as described herein with the mean value of the gene expression product in a population of healthy subjects and/or a population of patients unlikely to develop infection (FIG. 7). By way of an example, when the value of the gene expression product in a sample obtained from a subject is measured, a comparison module can compare or match the output data with the mean value of the expression product in a population of healthy subjects. In certain embodiments, the mean value of a gene expression product in a population of healthy subjects can be pre-stored in the storage module. In various embodiments, the comparison module can be configured using existing commercially-available or freely-available software for comparison purpose, and may be optimized for particular data comparisons that are conducted.

Figure 8:
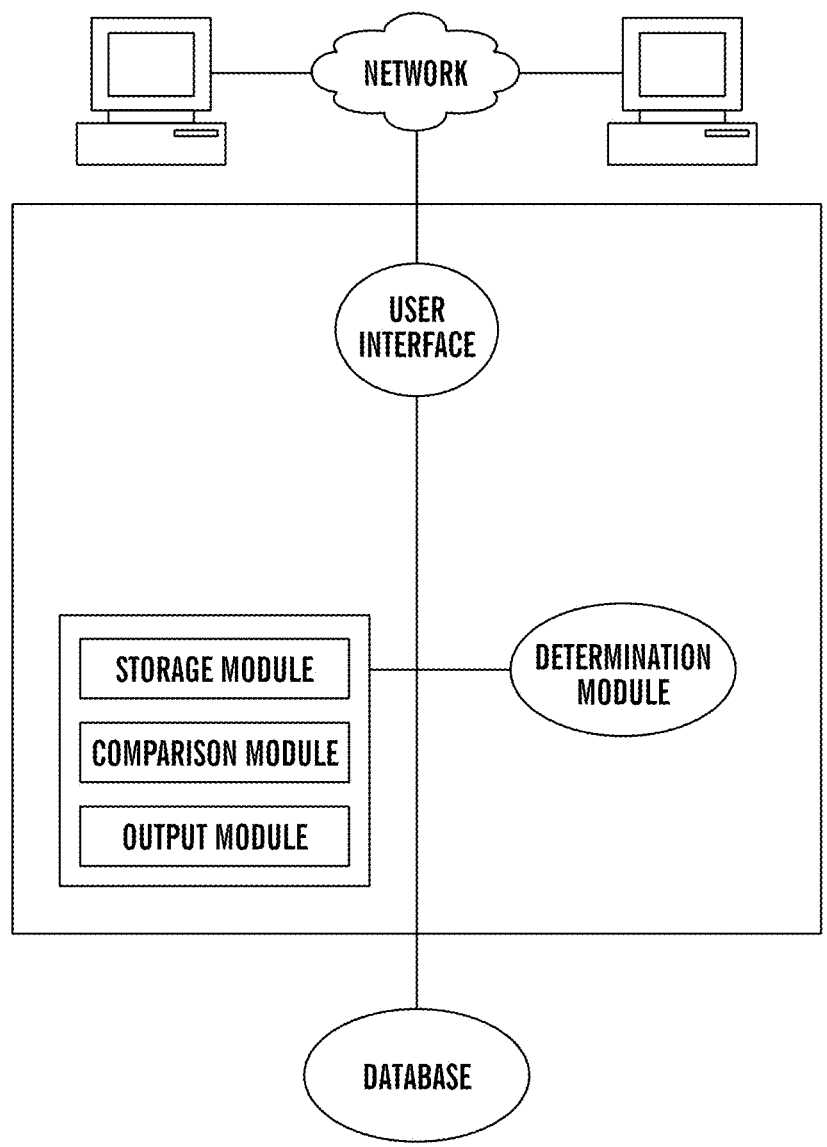
FIG. 8 is a diagram of an exemplary embodiment of an operating system and applications for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 8).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of a gene expression product of at least one gene of Table 4 or 5 in the sample obtained from a subject. In some embodiments, the content displayed on the display module can be the relative level of a gene expression product in the sample obtained from a subject as compared to the mean level of the expression product in a population of healthy subjects. In some embodiments, if the computing module determines that the level of the gene expression product in the test sample obtained from a subject is different (in the direction indicated by Table 4 or 5, e.g., wherein a reduced level of a gene expression product of a gene of Table 4 indicates an increased risk of having or developing an infection and an increased level of a gene expression product of a gene of Table 5 indicates an increased risk of having or developing an infection) by a statistically significant amount than the reference level, the display module displays a signal indicating that the levels in the sample obtained from a subject vary from those of the reference level. In some embodiments, the signal indicates the subject is in need of treatment for infection. In some embodiments, the signal indicates the degree to which the level of the gene expression product in the sample obtained from a subject varies from the reference level. In some embodiments, the content displayed on the display module can indicate whether the subject has an increased likelihood of having or developing infection. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having or developing infection. In some embodiments, the content displayed on the display module can be single word or phrases to qualitatively indicate a risk or probability. For example, a word "unlikely" can be used to indicate a lower risk for having or developing infection, while "likely" can be used to indicate a high risk for having or developing infection.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level a gene expression product of at least one gene selected from Table 4 or 5 in a sample obtained from a subject, and therefore are not intended to limit the scope of the invention. Variations of the systems and computer readable media described herein are possible and are intended to fall within the scope of the invention.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of infection. A subject can be male or female.

A subject can be one who has been previously diagnosed with or identified as suffering from or having a condition in need of treatment (e.g. infection, burn injury, immunosuppression, and/or inhalation injury) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. infection. The term "treating" includes reducing or alleviating at least one adverse effect or symptom of a condition, disease or disorder associated with an infection. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the various embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An assay comprising:
   Measuring the level of a gene expression product of at least one gene of Tables 4 and 5 a test sample obtained from a subject;
   wherein a decrease in the level of a gene expression product of a gene of Table 4 relative to a reference level indicates the subject has a higher risk of having or developing an infection and an increase in the level of a gene expression product of a gene of Table 5 relative to a reference level indicates the subject has a higher risk of having or developing an infection.

2. An assay comprising:
   contacting a sample obtained from a subject at risk of developing an infection with a probe to detect the level of a gene expression product of at least one gene of Tables 4 and 5;
   measuring the presence or intensity of a signal which indicates the presence or level of the gene expression product in the sample;

wherein a decrease in the level of a gene expression product of a gene of Table 4 relative to a reference level indicates the subject has a higher risk of having or developing an infection and an increase in the level of a gene expression product of a gene of Table 5 relative to a reference level indicates the subject has a higher risk of having or developing an infection 3. A method of identifying a subject in need of treatment for infection, the method comprising:
   measuring the level of a gene expression product of at least one gene of Tables 4 and 5 in a test sample obtained from a subject; and
   identifying the subject as being in need of treatment for infection when the level of a gene expression product of a gene of Table 4 is decreased relative to a reference level and the level of a gene expression product of a gene of Table 5 is increased relative to a reference level.

4. A method of determining if a subject is at risk for infection, the method comprising:
   providing a sample obtained from the subject;
   measuring the level of a gene expression product of at least one gene of Tables 4 and 5 in the sample;
   comparing the level of the gene expression product in the sample to a reference level of the gene expression product;
   determining that the subject is at risk for infection when the level of a gene expression product of a gene of Table 4 is decreased relative to a reference level and the level of a gene expression product of a gene of Table 5 is increased relative to a reference level; and
   determining that the subject is not at risk for infection when the level of a gene expression product of a gene of Table 4 is not decreased relative to a reference level and the level of a gene expression product of a gene of Table 5 is not increased relative to a reference level.

5. A method of determining the efficacy of a treatment for infection, the method comprising:
   (a) measuring the level of a gene expression product of at least one gene of Tables 4 and 5 in a test sample obtained from a subject before administration of the treatment;
   (b) measuring the level of the gene expression product in a test sample obtained from a subject after administration of the treatment; and
   wherein the treatment is determined to be efficacious when the level of a gene expression product of a gene of Table 4 measured in step (b) is not decreased relative to the level measured in step (a) and the level of a gene expression product of a gene of Table 5 measured in step (b) is not increased relative to the level measured in step (a).

6. The method of paragraph 5, wherein the treatment for infection is an anti-sepsis treatment.

7. A method of treatment for infection comprising;
   measuring the level of a gene expression product of at least one gene of Tables 4 and 5 in a test sample obtained from a subject;
   treating the subject with a treatment selected from the group consisting of:
     antibiotics; extended courses of antibiotics; immunotherapy; and LPS removal;
   when the level of a gene expression product of a gene of Table 4 is decreased relative to a reference level and the level of a gene expression product of a gene of Table 5 is increased relative to a reference level.

8. A method of treatment for infection comprising;
   administering a treatment selected from the group consisting of:
     antibiotics; extended courses of antibiotics; immunotherapy; and LPS removal;
   to a subject determined to have a level of a gene expression product of a gene of Table 4 that is decreased relative to a reference level or a level of a gene expression product of a gene of Table 5 that is increased relative to a reference level.

9. The assay or method of any of paragraphs 1-8, wherein the level of a gene expression product is determined by measuring the level of a nucleic acid.

10. The assay or method of any of paragraphs 1-9, wherein the level of a gene expression product is determined by determined the level of a RNA transcript.

11. The assay or method of any of paragraphs 1-10, wherein the level of the nucleic acid is determined using a method selected from the group consisting of: RT-PCR; quantitative RT-PCR; Northern blot; microarray based expression analysis; next-generation sequencing; and RNA in situ hybridization.

12. The assay or method of any of paragraphs 1-11, wherein the level of a gene expression product is determined by measuring the level of a polypeptide.

13. The assay or method of paragraph 12, wherein the level of the polypeptide is determined using a method selected from the group consisting of:
    Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

14. The assay or method of any of paragraphs 1-13, wherein the polypeptide level is measured using immunochemistry.

15. The assay or method of paragraph 14, wherein the antibody reagent is detectably labeled or generates a detectable signal.

16. The assay or method of any of paragraphs 1-15, wherein the expression level is normalized relative to the expression level of one or more reference genes or reference proteins.

17. The assay or method of any of paragraphs 1-16, wherein the expression level of a gene expression product of at least two genes of Tables 4 and 5 are measured.

18. The assay or method of any of paragraphs 1-17, wherein the expression level of a gene expression product of at least three genes of Tables 4 and 5 are measured.

19. The assay or method of any of paragraphs 1-18, wherein the expression level of a gene expression product of at least four genes of Tables 4 and 5 are measured.

20. The assay or method of any of paragraphs 1-19, wherein the expression level of a gene expression product of at least five genes of Tables 4 and 5 are measured.

21. The assay or method of any of paragraphs 1-20, wherein the expression level of a gene expression product of at least six genes of Tables 4 and 5 are measured.

22. The assay or method of any of paragraphs 1-21, wherein the genes are selected from the group consisting of:
THBS1; ARHGEF7; MDFIC; CCND2; OSBPL8; DCAF7; TMEM50B; GOLGA8A and/or GOLGA8B; SMARCA4; WHSC1L1; LOC101928343; and LINC00869.

23. The assay or method of any of paragraphs 1-22, wherein the expression level of a gene expression product of THBS1; ARHGEF7; MDFIC; CCND2; OSBPL8; DCAF7; TMEM50B; GOLGA8A and/or GOLGA8B; SMARCA4; WHSC1L1; LOC101928343; and LINC00869 is measured.

24. The assay or method of any of paragraphs 1-23, wherein the expression level of a gene expression product of CCND2; THBS1; MDFIC; SMARCA4; WHSC1L1; TMEM50B; DCAF7; and OSBPL8 is measured.

25. The assay or method of paragraph 24, wherein the subject is at least 16 years of age or older.

26. The assay or method of any of paragraphs 1-25, wherein the expression level of a gene expression product of NFKB2; MAX; PDLIM5; GATAD2B; and ZSCAN30 is measured.

27. The assay or method of paragraph 26, wherein the subject is 15 years of age or younger.

28. The assay or method of any of paragraphs 1-27, wherein the sample comprises blood or plasma.

29. The assay or method of any of paragraphs 1-28, wherein the sample comprises muscle tissue and the one or more genes are selected from the group consisting of:
ALDH1A1; ALDH1A2; ALDH3B1; ALDH5A1; ALDH6A1; and ALDH7A1.

30. The assay or method of any of paragraphs 1-29, wherein the method further comprises
determining the values of total body surface area (TBSA) burns, age, and/or inhalation status;
wherein an increase in any of the preceding values indicates an increased risk of the subject having or developing infection.

31. The assay or method of any of paragraphs 1-30, wherein the method further comprises multiplying each gene expression value measured, and optionally, the total body surface area (TBSA) burns, age, and/or inhalation status values, by a coefficient and adding the resulting products to yield a risk value.

32. The assay or method of paragraph 1-32, wherein a risk value of greater than the computed reference baseline coefficient value indicates the subject is at risk of having or developing infection and/or is in need of treatment for infection.

33. The assay or method of paragraph 1-32, wherein the coefficient is about the coefficient provided in Table 7.

34. The assay or method of paragraph 33, wherein a risk value of greater than about −1.1912 indicates the subject is at risk of having or developing infection and/or is in need of treatment for infection.

35. The assay or method of any of paragraphs 1-34, wherein the infection comprises a microbe selected from the group consisting of:
Gram-negative bacteria; *Staphylococcus* spp.; *Staphylococcus aureus*; coagulase-negative *Staphylococci*; *Enterococcus* spp.; *Candida* spp. *Escherichia coli*; *Enterobacter* spp.; *Klebsiella pneumonia*; *Acinetobacter* spp.; *Pseudomonas aeruginosa*; *Streptococcus pneumonia*; *Streptococcus viridans*; Gram-positive bacteria; *Serratia marcescens*; *Hemophilus influenza*; *Stenotrophomonas* spp.; *Proteus*; *Aspergillus*; *Neisseria*; *Clostridium* sp.; *Bacteroides* sp; fungi; cytomegalovirus; and herpes virii.

36. The assay or method of any of paragraphs 1-35, wherein the subject at risk of infection is a subject at risk of a condition selected from the group consisting of:
multiple infection episodes; sepsis; pneumonia; urinary tract infection; blood stream infection; catheter-related infection; and wound infection.

37. The assay or method of any of paragraphs 1-36, wherein the subject at risk of infection is a subject having or diagnosed as having a condition selected from the group consisting of:
a burn injury; inhalation injury; immunosuppression; major surgical procedures;
intubation or catheters; blunt trauma; penetrating trauma; burn trauma; diabetes;
diabetic infection complications; HIV; or
a subject in the intensive care unit and with central lines.

38. The assay or method of any of paragraphs 1-37, further comprising the step of detecting the presence of susceptibility-associated SNPs or pathogen markers in the sample obtained from the subject.

39. A kit for performing the method/assay of any of paragraphs 1-38.

40. A computer system for determining the risk of a subject having or developing an infection, the system comprising:
a measuring module configured to measure the level of a gene expression product of at least one gene of Tables 4 and 5 in a test sample obtained from a subject;
a storage module configured to store output data from the determination module;
a comparison module adapted to compare the data stored on the storage module with a reference level, and to provide a retrieved content, and a display module for displaying whether the sample comprises a level of the gene expression product which is significantly different relative to the reference expression level and/or displaying the relative level of the gene expression product.

41. The system of paragraph 40, further comprising an output module for reporting/displaying the probability of a subject developing infections.

42. The system of paragraph 41, wherein the probablility is calculated from the input from the measuring module and clinical parameters.

43. The system of any of paragraphs 41-42, wherein the probability is calculated with at least a 95% confidence interval.

44. The system of any of paragraphs 41-43, wherein the measuring module measures the intensity of a detectable signal from an assay indicating the level of a polypeptide in the test sample.

45. The system of paragraph 44, wherein the assay is an immunoassay.

46. The system of any of paragraphs 40-45, wherein the measuring module measures the intensity of a detectable signal from a RT-PCR assay indicating the level of a RNA transcript in the test sample.

47. The system of any of paragraphs 40-46, wherein if the computing module determines that the level of the gene expression product in the test sample obtained from a subject differs by a statistically significant amount from the reference level, the display module displays a signal indicating that the levels in the sample obtained from a subject are different than those of the reference level.

48. The system of any of paragraphs 40-47, wherein the signal indicates that the subject has an increased likelihood of having or developing an infection.
49. The system of any of paragraphs 40-48, wherein the signal indicates the subject is in need of treatment for an infection.
50. The system of any of paragraphs 40-49, wherein the signal indicates the degree to which the level of the gene expression product in the sample obtained from a subject varies from the reference level.

EXAMPLES

Example 1

Described herein are methods and assays relating to the treatment of infection. Described herein are three predictive models using multivariate logistic regression and the following covariates: 1) clinical characteristics of age, TBSA, and the presence of inhalation injury; 2) 14 genomic probe sets from early (<180 h) blood transcriptome; 3) both clinical and genomic covariates. The clinical model (AUROC=0.864 [CI, 0.794-0.933]) and the 14-probe set genomic model (AUROC=0.946 [CI, 0.906-0.986]) were highly predictive of MIE status, with the latter providing a more accurate prognosis. Combining the two increased the AUROC to 0.967 (CI, 0.940-0.993). Described herein are genomic signatures that predict hypersusceptibility to infection.

Example 2: Prediction of Multiple Infections after Severe Burn Trauma: A Prospective Cohort Study To develop predictive models for early triage of burn patients based on hyper-susceptibility to repeated infections. Infection remains a major cause of mortality and morbidity after severe trauma, demanding new strategies to combat infections. Models for infection prediction are lacking. Secondary analysis of 459 burn patients (≥16 years old) with ≥20% total body surface area burns recruited from six US burn centers. Blood transcriptomes with a 180-h cut-off on the injury-to-transcriptome interval of 47 patients (≤1 infection episode) were compared to those of 66 hyper-susceptible patients (multiple [≥2] infection episodes [MIE]). Described herein the use of LASSO regression to select biomarkers and multivariate logistic regression to built models, accuracy of which were assessed by area under receiver operating characteristic curve (AUROC) and cross-validation.

Three predictive models were developed covariates of: (1) clinical characteristics; (2) expression profiles of 14 genomic probes; (3) combining (1) and (2). The genomic and clinical models were highly predictive of MIE status (AUROC$_{Genomic}$=0.946 [95% CI, 0.906-0.986]); AUROC$_{Combined}$=0.864 [CI, 0.794-0.933]; AUROC$_{Genomic}$/AUROC$_{Clinical}$ P=0.044). Combined model has an increased AUROC$_{Combined}$ of 0.967 (CI, 0.940-0.993) compared to the individual models (AUROC$_{Combined}$/AUROC$_{Clinincal}$ P=0.0069). Hyper-susceptible patients show early alterations in immune-related signaling pathways, epigenetic modulation and chromatin remodeling.

Early triage of burn patients more susceptible to infections can be made using clinical characteristics and/or genomic signatures.

Early genomic signature and clinical characteristics of 113 burn patients were used paradigmatically to build three novel predictive models of multiple, repeated infections in burn trauma, which can facilitate early triage of traumatically injured burn patients to prevent or treat sepsis. Genomic signature indicates new mechanistic aspects of hyper-susceptibility to infections.

Introduction

Although several studies have found association between specific risk factors or clinical characteristics with mortality after trauma,[1-4] studies attempting to apply those clinical characteristics or genomic biomarkers to appreciate susceptibility to infection and build predictive models are currently lacking. Improvements in early care and trauma centers have reduced early mortality considerably.[3,5] However, severe trauma, such as burn trauma, cause immunosuppression which predispose patients to infections. Despite all medical improvements, infections remain a major cause of critical injury-related morbidity and mortality, and recurrent sepsis predisposes patients to multiple organ failure, lengthens hospital stays, and increases costs.[6] Therefore, improvements in prevention and treatment of infections are increasingly important.[7,8] Moreover, the rapid emergence of multi- (MDR) or pan-drug resistant (PDR) pathogens that cause highly problematic acute, persistent or relapsing infections pose a dire threat to healthcare, especially among trauma and surgical patients.[9,10] The increased use of antibiotics has further accelerated their emergence,[11-13] and also increased the challenge of treating polymicrobial wound infections.[14,15] Due to the paucity of novel anti-infectives in development, further improvement in patient care and treatment efficacy may rely heavily on optimizing existing strategies and promoting patients-tailored therapies.[16-18]

Successful personalized approach requires rigorous triaging: early and accurate identification of patients more susceptible to infections could help tailor the anti-infective treatments,[19,20] and especially to elaborate long-term treatment plan. Future successful clinical trials aiming to improve sepsis outcome may also rely on biomarkers to identify the right patients for the right treatment.[21,22] Several studies have reported risk factors associated with increased probability of infection and sepsis in trauma patients,[23-26] but no specific predictive model has been developed. Existing plasma biomarkers such as C-reactive protein (CRP) and procalcitonin (PCT) are mainly used to diagnose sepsis[27,28] rather than reflective of susceptibility or health status. The clinical characteristics measurable rapidly upon admission are the current gold standard for prognosis of general patient's outcome.

As trauma promotes susceptibility to infection and genomic signatures appear to play an increasingly promising role in prognosis,[26,29] the blood transcriptome and clinical characteristics data of 113 patients from the 573 thermally injured patients enrolled in the Inflammation and the Host Response to Injury study were analyzed. Using clinical characteristics available upon admission and early genomic signatures, novel predictive models were developed, as described herein, that permit early identification of burn patients at high risk of developing repeated infection indicative of an early hyper-susceptible state. The genomic signature indicates new mechanistic aspects for susceptibility to infection after burn trauma.

Methods

Subject Recruitment and Sample Selection.

This study was conducted via secondary use of the clinical and genomic data of the Inflammation and the Host Response to Injury Study ("Glue Grant"). Briefly, 573 burn patients with minimum 20% total burn surface area (TBSA) were enrolled from six institutions between 2003 and 2009 in a prospective, longitudinal study. RNA of leucocytes isolated from whole blood samples were extracted for transcriptome analysis using Affymetrix GeneChip Human Genome U133 Plus 2.0 microarrays at University of Florida-Gainesville, as described previously.[30] The complete inclusion/exclusion criteria are described elsewhere.[31] Permission for this secondary use of the de-identified data was obtained from the Massachusetts General Hospital Institutional Review Board.

The patient inclusion process is summarized in FIG. 1. From 573 potential patients in the data pool, patients were selected that were at least 16 years old with early transcriptome data. A 180-h cut-off limit was set on the injury-to-transcriptome interval to include only samples that were obtained early relative to the recovery process, while still allowing enough samples to remain eligible for biomarker discovery. If multiple blood samples were collected from a patient, only the earliest eligible sample was included. Patients who died within 9 days of blood collection and had fewer than two infection episodes during this time window were excluded (FIG. 1). The method for collection of data related to clinical characteristics is described elsewhere.[31] To enable direct comparisons, as well as combination of clinical and genomic prediction, the same set of patients was used for both clinical characteristic and genomic signature prediction models.

Definition of Outcomes.

Infections were defined according to the information collected in the Glue Grant database based on previously described standards.[32] Infection episodes were quantified for each patient for up to 60 days after blood sample collection. A decision tree (FIG. 1 and FIG. 11) was developed for evaluating each record based on: (1) time of infection; (2) type of infection; and (3) the pathogen(s) isolated. Since no genotyping data of the isolated pathogen species were available, it was not possible to classify whether a later episode was caused by the same strain isolated earlier. However, once a record was counted, the infection type and isolated pathogen combination (e.g. *Pseudomonas aeruginosa*+lung) was put on a "waiting list" for the next 6 days, which likely reduced the likelihood of an infection episode caused by the same isolate from being counted. Subsequent records that were part of the same infection episode were thereby omitted. The patients were separated into two groups based on susceptibility to infection, measured by the number of independent infection episodes recorded. Patients with ≤1 infection episodes were defined as the less susceptible control group (N=47), and patients with ≥2 (multiple) infection episodes (MIE) as the hyper-susceptible case group (N=66).

Microarray Processing and Filtering

Figure 9A:
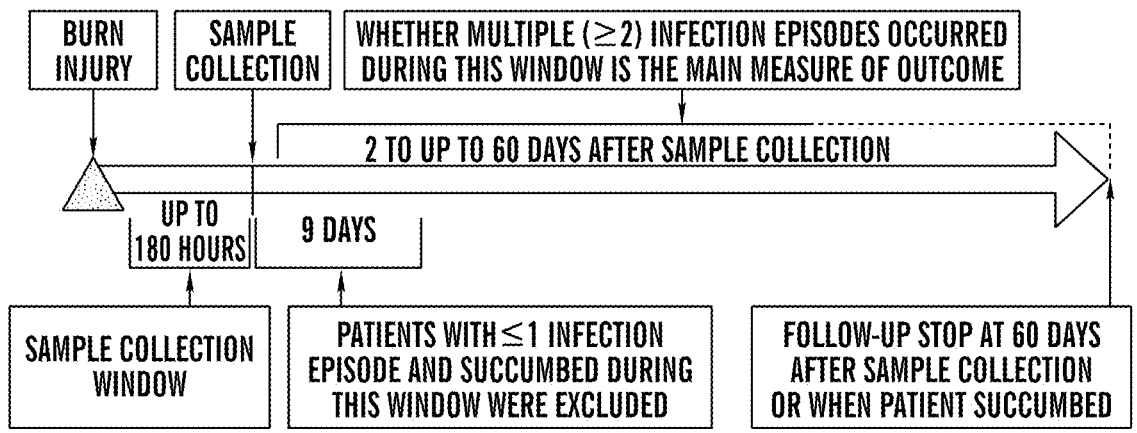
FIG. 9A depicts a timeline of the study.
Figure 9B:
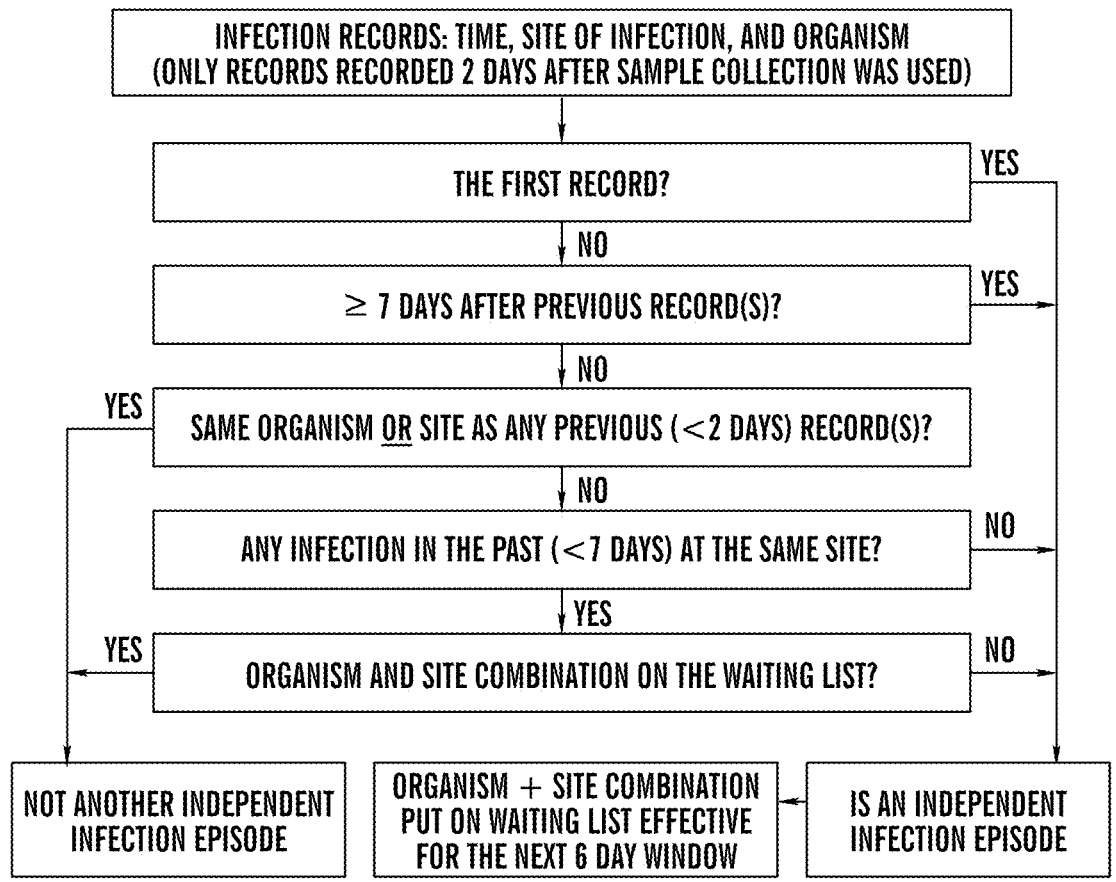
FIG. 9B depicts a decision tree used to define independent infection episodes using available clinical and microbiological records. Overriding rules of the decision tree are as included below the table and also described in the methods section.
Figure 10:
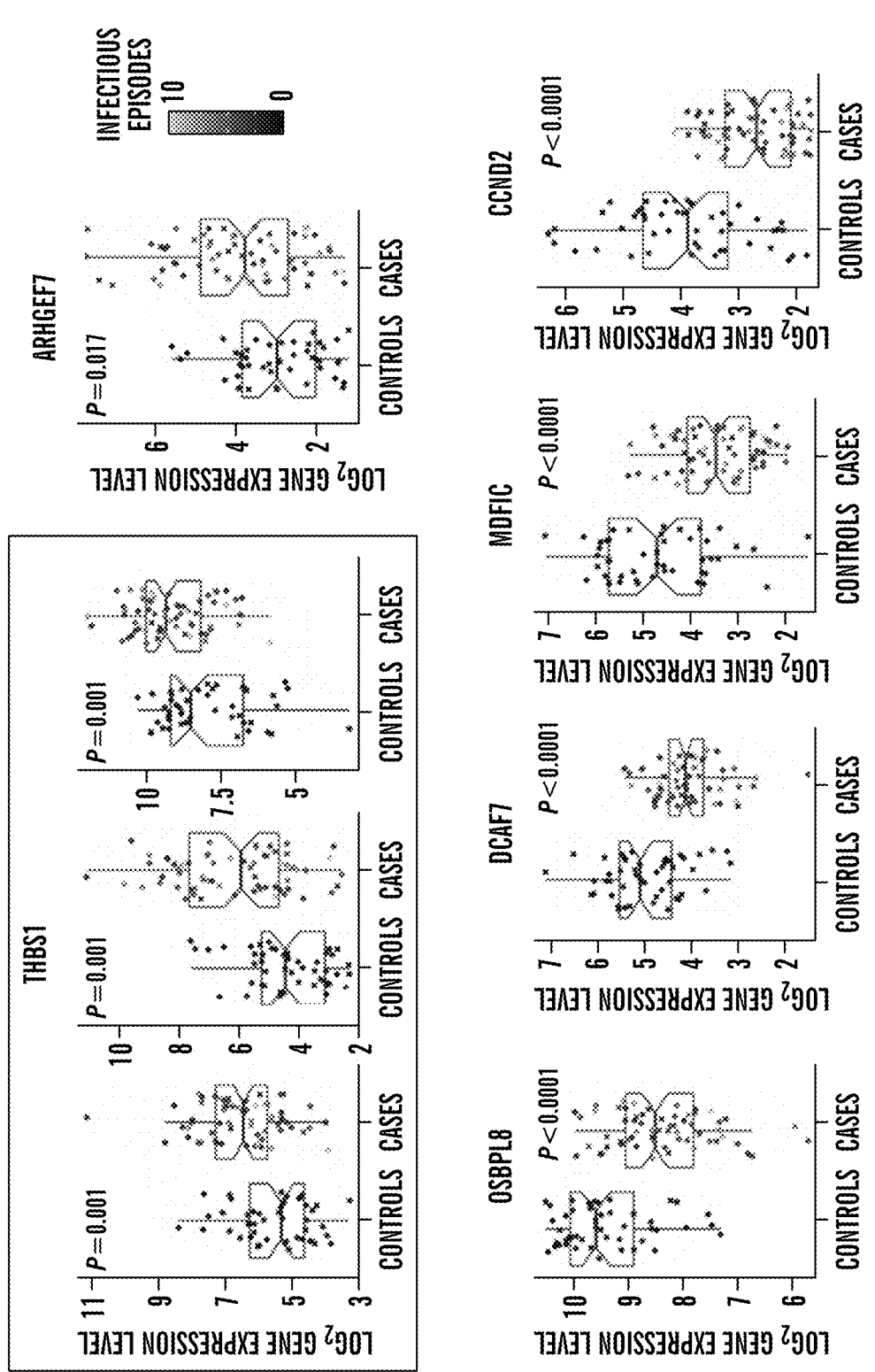
FIG. 10 depicts graphs of the expression profile of 12 genes in the biomarker panel. A total of 14 probe sets mapped to 12 genes are shown as scatter plot overlaid with notched box plots. P values were calculated using limma package in R software using moderated t-statistics and then adjusted for multiple comparisons using B-H method. Each data point in the scatter plot corresponds to a sample from a patient, and color-coded based on the total infection episodes the patient had from 2 days to 60 days after blood collection.
Figure 10:
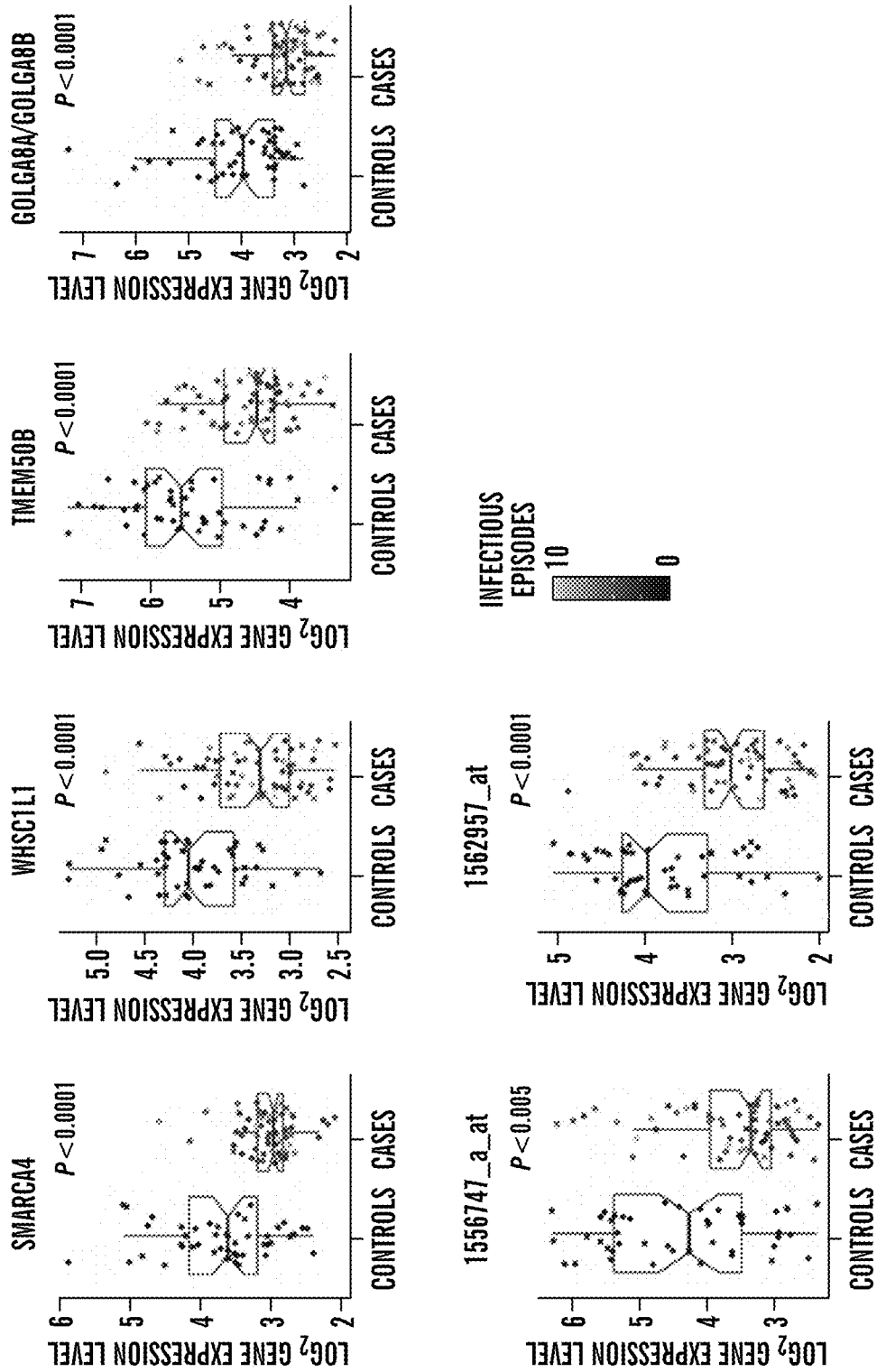

Raw microarray data (.CEL files) were downloaded from the Glue Grant website (available on the world wide web at.gluegrant.org/trdb/) and filtered using the steps outlined in FIG. 1; FIG. 11; FIG. 9B. The gcrma[33] package on the R/Bioconductor platform[34] was used to normalize 124 blood samples from 124 eligible patients collected within 180 h post-injury. Samples identified as outliers by arrayQualityMetrics[35] were excluded from subsequent analysis. One patient was removed due to incompleteness of clinical data. Two patients' datasets were discarded due to mortality within 9 days after sample collection. After these filtration steps, 113 blood samples were deemed suitable high-quality microarray data sets for subsequent functional analyses, biomarker discovery, and modeling.

The EMA package[36] in R software was used to filter outlying or information-poor probe sets. Probe sets with a maximum $\log_2$ expression value below 3.5, were eliminated, reducing the number of probe sets from 54,675 to 26,107. Using limma package,[37] 1142 probe sets with an at least 1.5-fold difference between less susceptible patients and hyper-susceptible patients and with an average expression level of at least 3 were selected for functional analyses and biomarker panel selection process.

Statistical Analysis Clinical Data Set.

Continuous variables are reported as means (standard deviations), or as medians with inter-quartile ranges (IQRs) as indicated. Categorical variables are reported as frequencies and percentages. Demographic variables between less susceptible and hyper-susceptible patients were tested for statistical difference with a Wilcoxon rank sums test, a Chi-square test, or a Fisher's exact test as appropriate. Statistical significance was accepted at P<0.05 (two-tailed when appropriate).

Body mass index (BMI) was calculated as weight/height$^2$ (kg/m$^2$). For patients ≥20 years old, BMI categories of underweight, healthy, overweight and obese were define according to BMI numbers: <18.5, 18.5-24.9, 25-29.9, and ≥30, respectively; whereas for patients <20 years old, the same BMI categories were defined using percentile ranking based on Centers for Disease Control and Prevention BMI-for-age growth charts: <5$^{th}$ percentile, 5$^{th}$ to <85$^{th}$ percentile, 85$^{th}$ to ≤95$^{th}$ percentile, and ≥95$^{th}$ percentile, respectively.

Genomic Data Set.

In the evaluation of significant expression differences between less susceptible and hyper-susceptible patients, Benjamini-Hochberg multiple-comparison adjustments were applied to control for false discovery rate.

Development of the Clinical Predictive Models.

Stepwise logistic regression was implemented with an entry level of 0.3 and a stay level of 0.25 to identify significant predictor variables among clinical covariates relevant to the outcome variable of MIE: TBSA, age, BMI, and the presence of inhalation injury. Predictive power was determined by calculating area under receiver operating characteristic curve (AUROC), reported with 95% confidence intervals (CIs).

Development of the Genomic Predictive Models.

Figure 3A:
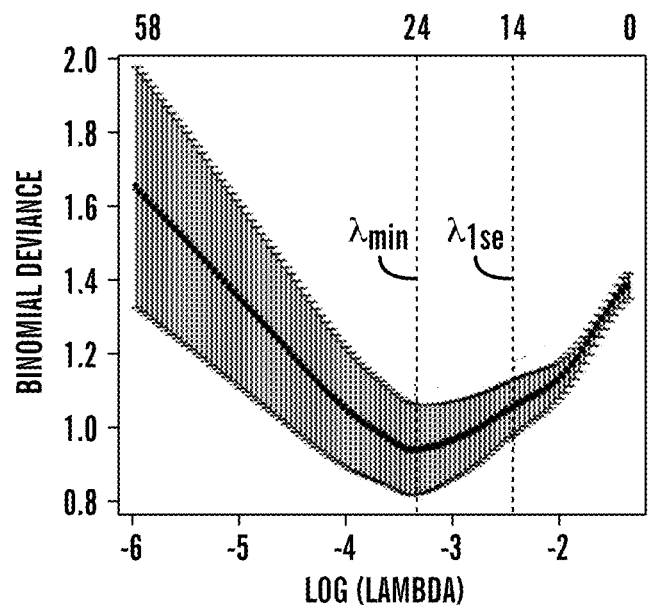
FIGS. 3A-3B demonstrate biomarker selection by LASSO regularized regression.
Figure 3B:
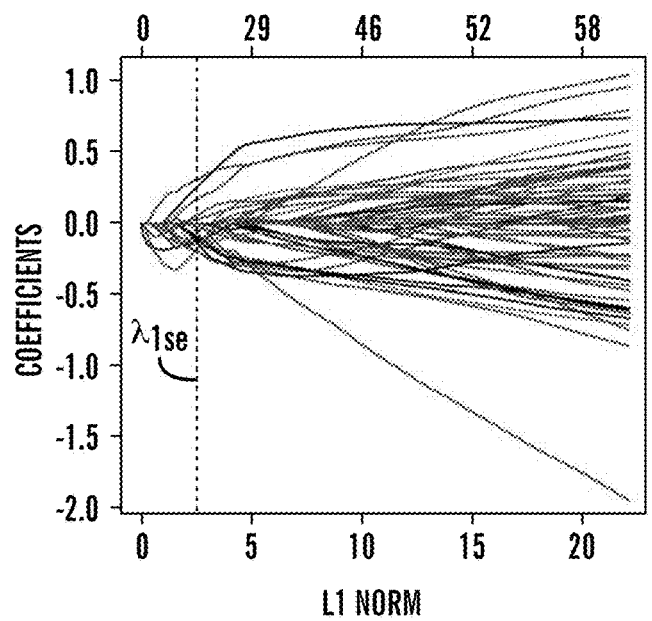

The LASSO regularized regression method[38] implemented in the glmnet package[39] in R software was used to identify probe sets that collectively predicted the likelihood of MIE. 10-fold cross-validation (CV) was used to select the optimal value of LASSO penalty weighting, $\lambda$. The value of $\lambda$ that gave the minimum average binomial deviance plus 1 standard error on the test set, $\lambda_{lse}$, was used to select probe sets (FIG. 3A). $\lambda_{lse}$, is a stronger penalty parameter to guard against over-fitting than $\lambda_{min}$, which minimizes the average binomial deviance of CV (FIG. 3B). This 10-fold CV process was repeated 100 times to generate 100 $\lambda_{lse}$ values. The median $\lambda_{lse}$, 0.0940, yielded selection of a 14-probe-set biomarker panel (Table 2). Logistic regression was performed to model the MIE outcome with the $\log_2$ expression values of the 14 probe sets as explanatory variables. Furthermore, we conducted multivariate logistic regression with the clinical covariates TBSA, age, and inhalation injury together with the 14 probe sets for the outcome variable of MIE. Leave-one-out cross-validation was used to assess the degree of over-fitting and model performance.

Functional Analysis

Functional and pathway analyses were conducted using Ingenuity IPA (Ingenuity® Systems) and DAVID.[40]

Software Platform and Package Versions

R (version 2.15.*); EMA package for R (version 1.3.2); pROC package for R (version 1.5.4); limma package for R (version 3.14.4); glmnet package for R (version 1.9-3); arrayQualityMetrics package for R (version 3.14.0); gcrma package for R (version 2.30.0); JMP Pro 10 and SAS 9.3 (SAS Institute Inc., North Carolina, USA).

Results

Clinical Characteristics.

From a pool of 573 patients, 124 met the inclusion criteria, of which 11 were unsuitable for modeling, leaving a cohort of 113 patients (FIG. 1), including 47 patients less susceptible to infection (control group with ≤1 infection episodes) and 66 hyper-susceptible patients (case group with multiple [≥2] infection episodes [MIE]). The demographics, injury characteristics, and outcomes of these 113 patients are summarized in Table 1.

From 612 microbiological records for the 113 patients in the final cohort, 325 independent infection episodes, 107 (32.9%) of which are polymicrobial at the species level, were identified. Twenty-four patients had no infection episodes, 23 had one episode, and 66 had MIE. The less susceptible and hyper-susceptible patients show significantly different clinical characteristics (Table 1). Relative to the control group, hyper-susceptible patients were slightly older (mean, 38.2, SD 16.4 vs 37.0, SD 14.6), had higher TBSA (46%, IQR 35-71 vs 32%, IQR 23-41, P<0.0001), had more inhalation injuries (41/66 [62.1%] vs 8/47 [17.0%], P<0.0001) and were more severely ill (according to their APACHE II score 24, IQR18-29 vs 13, IQR 9-20, P<0.0001). They also had longer hospital stays (median, 60, IQR 33-71 vs 20, IQR 15-30, P<0.0001), more days on mechanical ventilation (median, 28, IQR13-40 vs 2, IQR 0-5, P<0.0001), and had a higher mortality (18/66 [27.3%] vs 3/47 [6.4%], P=0.0029) (Table 1). The median post-injury interval for the second episode in the case group was 15 days (IQR, 10-20; range, 3-43), a time window that provides opportunity for prophylactic intervention.

Inhalation injury significantly increased the risk of developing MIE and may be related to pneumonia risk in particular: 78.8% of hyper-susceptible patients had pneumonia vs 10.6% of controls; among cases, 84.7% had both MIE and inhalation injuries, 67.4% had both pneumonia and inhalation injuries. Interestingly, 4/5 of underweight patients had MIE (Table 1), supporting the notion that being overweight and mild obesity may be protective against post-injury infection whereas being underweight increases risk.[32,41]

Figure 2A:
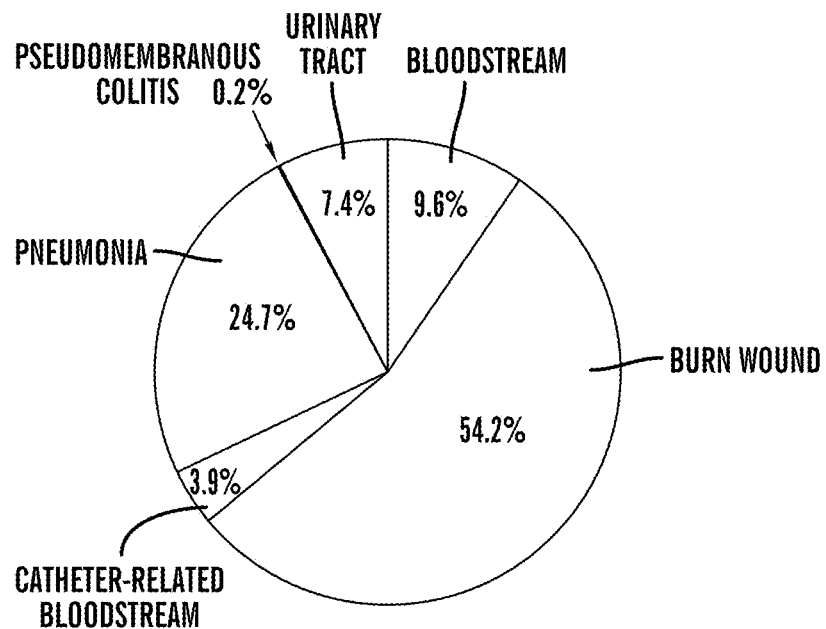
FIGS. 2A-2B depict graphs demonstrating the type of infections and isolated pathogens.
Figure 2B:
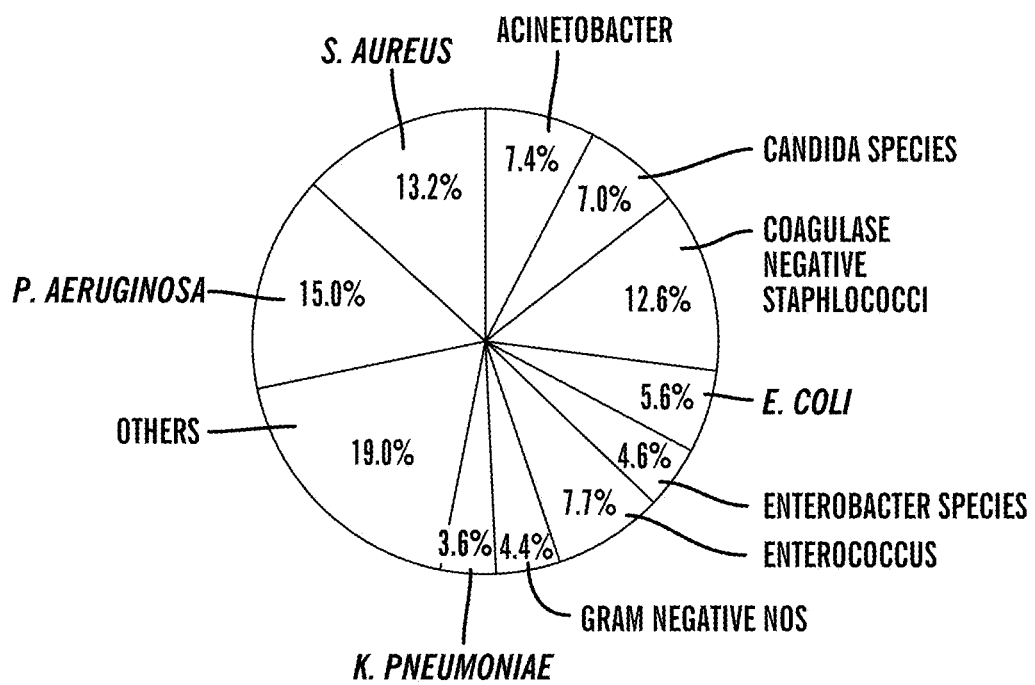

Burn wound infection and nosocomial pneumonia were the most frequent types of infection observed (Table 1; FIG. 2A). *Pseudomonas aeruginosa* and Staphylococci (both *Staphylococcus aureus* and coagulase negative Staphylococci) were the most commonly isolated micro-organisms (Table 1; FIG. 2B). *P. aeruginosa* and *Acinetobacter* infections were more common among patients with MIE than controls, suggesting that hyper-susceptible patients were even more susceptible to nosocomial Gram-negative pathogens.

MIE Prediction from Clinical Characteristics

Figure 4:
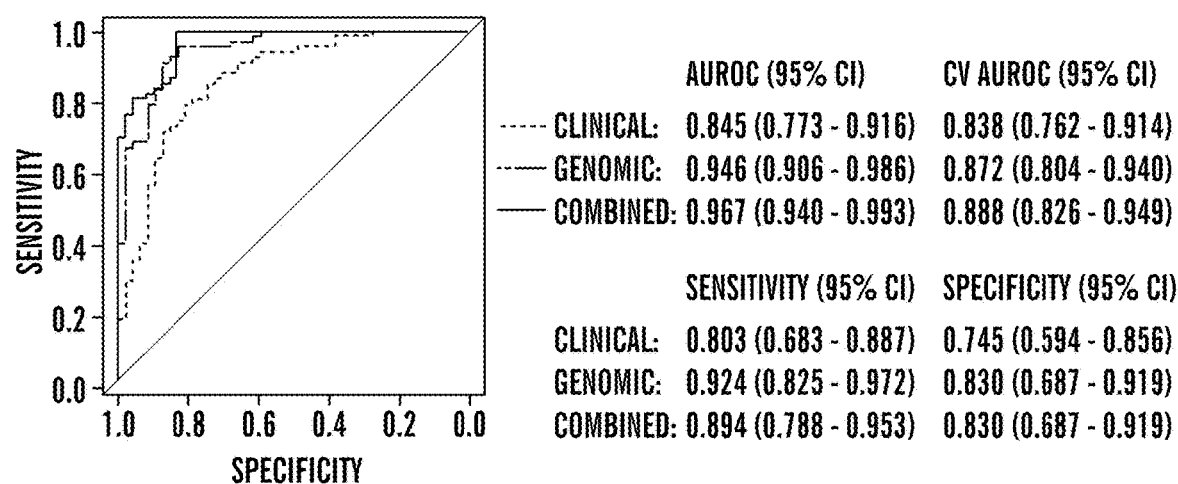
FIG. 4 depicts clinical and genomic prediction models. ROC curves of the clinical model, genomic model, and combined model, and their respective AUROC, cross-validated (CV) AUROC, sensitivities, and specificities; 95% CIs are reported in parentheses.

Stepwise logistic regression to select covariates for modeling from TBSA, age, BMI, and the presence of inhalation injury. The final multivariate logistic regression model included three covariates: TBSA, age, and inhalation injury, which were significant independent predictors of MIE. The AUROC, CV AUROC, sensitivity, and specificity values for the clinical characteristics model are 0.845 (95% CI, 0.773-0.916), 0.838 (95% CI, 0.762-0.914), 0.803 (95% CI, 0.683-0.887), and 0.745 (95% CI, 0.594-0.856), respectively (FIG. 4). The model's positive and negative predictive values were 0.815 (95% CI, 0.696-0.843) and 0.729 (95% CI, 0.579-0.843), respectively. Inhalation injury significantly increased MIE incidence (odds ratio [OR], 6.942; 95% CI, 2.482-19.417). Patients who had inhalation injuries were twice as likely to get pneumonia compared to those without them (risk ratio [RR], 2.05; 95% CI, 1.37-3.07). Among those who had inhalation injuries, 67.4% had pneumonia, and 83.67% had MIE. TBSA (OR, 1.078; 95% CI, 1.040-1.118) and age (OR, 1.040; 95% CI, 1.006-1.075) were also associated with increased infection susceptibility.

MIE Prediction from Genomic Biomarkers in Blood

Ten-fold CV using LASSO regularized regression[38] of the 1142 probe sets that presented a minimum of 1.5-fold change between the two patient groups yielded a minimal set of 14 predictors (probe sets) that together optimized the fit of the model (FIGS. 3A and 3B). Of these 14 probe sets—which mapped to 12 genes—4 were upregulated and 10 were down-regulated (Table 2, all P<0.01; heat map and clustering of patients and biomarkers not shown; see FIG. 2A-2B for expression profiles of each probe set). The biological processes associated with each probe set are presented in Table 3 together with the coefficients of the biomarker panel logistic regression model (model intercept=0.7449; Stable 12).

The AUROC, CV AUROC, sensitivity, and specificity values for the resulting genomic signature model are 0.946 (95% CI, 0.906-0.986), 0.872 (95% CI, 0.804-0.940), 0.924 (95% CI, 0.825-0.972), and 0.830 (95% CI, 0.687-0.919), respectively (FIG. 4), confirming the model to be highly sensitive and specific. The positive and negative predictive values of the model were 0.884 (95% CI, 0.779-0.945) and 0.886 (95% CI, 0.746-0.957), respectively. Each patient's probability of developing MIE estimated from the clinical or genomic biomarker logistic regression models was compared with each of the observed outcomes, using cut-off points of 30% to 70% as being uncertain. It was found that the clinical model correctly predicted outcomes of 73 (65%) patients with certainty. Comparatively, the genomic biomarker model correctly predicted 90 (80%) patients with certainty, showing a 15% improvement over the clinical model. Both models misclassified 9 patients (8%). Collectively, these data indicate that genomic biomarkers may complement triage by clinical characteristics and enhance early prediction of a patient's likelihood to develop MIE.

MIE Prediction from a Combined Model

A multivariate logistic model that included the aforementioned clinical covariates (TBSA, age, presence of inhalation injury) and genomic biomarkers resulted in an AUROC (0.967; 95% CI, 0.940-0.993) that was significantly greater than that for the clinical model (P=0.0069), but not significantly different from that of the genomic biomarker panel model (FIG. 4). The positive and negative predictive values of the combined model were 0.881 (95% CI, 0.773-0.943) and 0.848 (95% CI, 0.705-0.932), respectively. The estimates of the above models are listed in Table 12.

Figure 5:
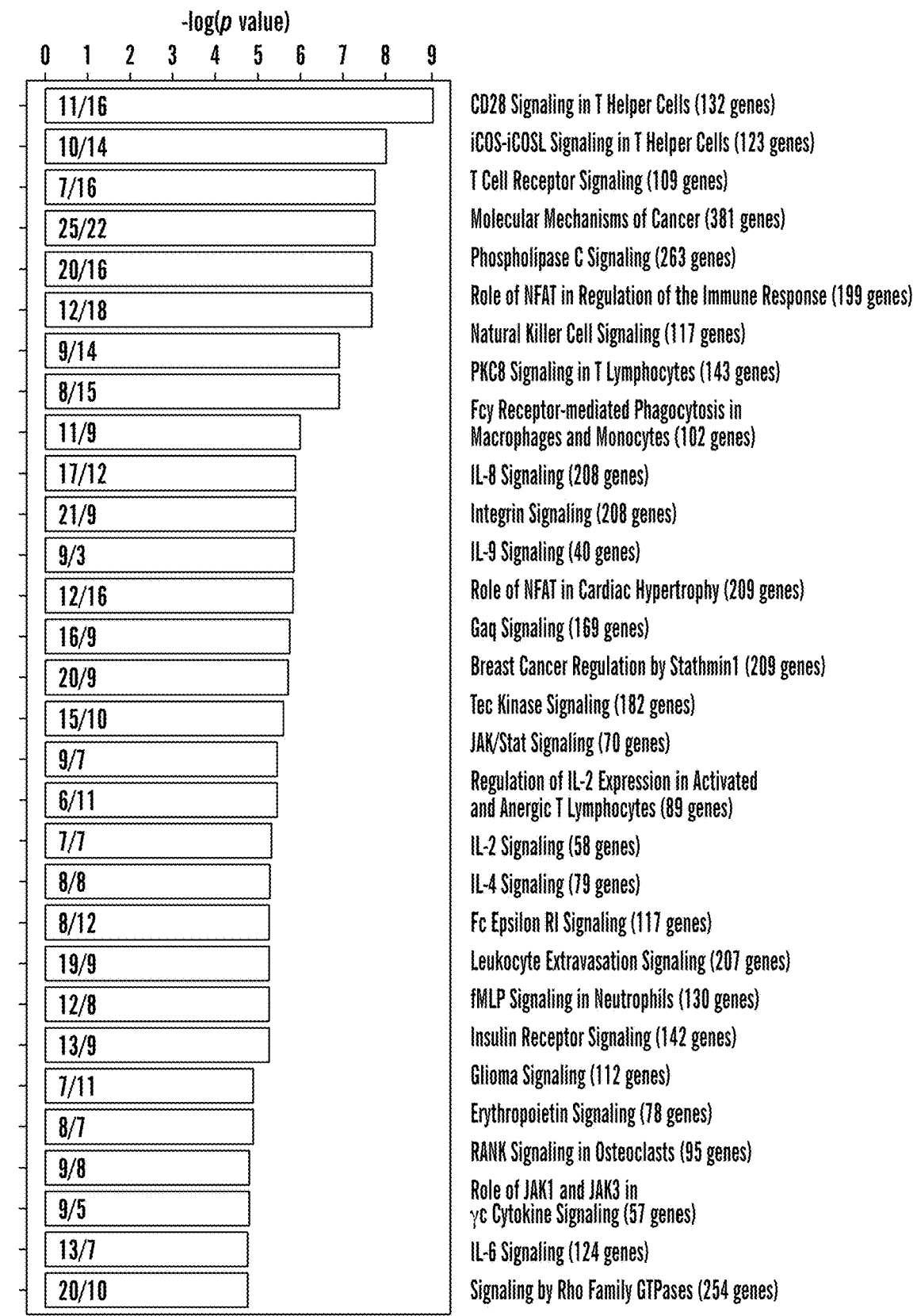
FIG. 5 depicts the alteration of pathways. Top 30 pathways significantly altered in case group with multiple infection episodes (MIE). X-axis is the negative log P value calculated from Fisher's exact test right-tailed. The first number in each grey bar is the number of upregulated genes, the second number in each grey bar is the number of down-regulated genes. The total number of genes in a pathway is indicated in the parenthesis after pathway name. P value is calculated by Fisher's exact test by IPA software.

Functional and Canonical Pathway Changes in Patients with MIE Revealed by Transcriptome Data Analysis The 1142 probe sets showing a minimum of 1.5-fold change in hyper-susceptible patients versus less susceptible patients were mapped to 844 annotated genes. Functionally related genes were identified among these 884 genes using Gene Ontology (GO). Subsequent analysis of the changes in canonical pathways and functions linked to these 844 genes indicated that hyper-susceptible patients' transcriptomes demonstrated the following early functional changes relative to control transcriptomes: (1) early activation of immune cells, increased chemotaxis and trafficking; (2) decreased expansion of leukocytes, thymocytes, and number of phagocytes, and increased cell death and apoptosis; and (3) suppression of immune cell activation and lymphoid organ development (Table 2). The 1142 probe sets showed enrichment in four main gene ontology biological process categories: (1) immune response; (2) epigenetic modulation of gene expression; (3) transcription; and (4) metabolism (Table 13). Functional enrichment clustering is also in agreement with the enrichment of the 4 functional groups (Table 14). The top 30 affected pathways were mainly involved in immune cell signaling and cytokine signaling (FIG. 5). Canonical pathway analysis using IPA software (FIG. 5) largely agrees with KEGG pathway enrichment analysis using DAVID (Table 15), providing additional confidence. Overall, many of the predicted functional changes (Table 2) are downstream of the affected canonical pathways (FIG. 5; Table 15).

Canonical Pathways and T-cell Signaling

Significant changes in IL-8 signaling (17 upregulated and 12 down-regulated genes [17 up/12 down]), Gaq signaling (16 up/9 down), Rho family GTPase signaling (20 up/10 down) and integrin signaling (21 up/9 down) indicates that the adhesion and migration of leukocytes are affected (Table 2; Table 14; and FIG. 5). The changes in chemotaxis may be partially caused by the presence of bacteria at wound site, as fMLP signaling pathway (12 up/8 down) suggests. Genes involved in phospholipase C signaling, a regulator of chemotactic response are differentially expressed (20 up/16 down). The increased cell movement, adhesion, and chemotaxis are related to phagocytosis process (e.g. FcγR-mediated phagocytosis, Table 12), clearance of the pathogen from the site of infection, and induced by host damage associated molecular patterns (DAMP).

Strong evidence was found that T-cells were also differentially regulated in case patients. Several pathways, including T-cell receptors (TCR) (7 up/16 down), JAK-STAT signaling (9 up/7 down), PKCO signaling (8 up/15 down), and IL-6 signaling pathway (13 up/6 down) are known to regulate T-cell differentiation, activation, and cytokine production. Changes in iCOS-iCOSL signaling (10 up/14 down), CD28 signaling (11 up/16 down), and IL-2 signaling (7 up/7 down), indicate that T helper cell maturation and proliferation were likely affected. In summary, patient transcriptome data is consistent with compromised cellular immune responses mediated by impaired T-cells signaling.

Functional Enrichment in Histone Modification and Chromatin Remodeling

Evidence was found for dramatic epigenetic changes in leukocytes that long precede patient outcome of MIE. Functions related to epigenetic modulation were commonly enriched in our functional enrichment analyses (Tables 13, 14, and 11). Notably, 42 probe sets (39 genes) have functional annotation associated with chromatin remodeling and histone modifications (Table 11). Two genes from the biomarker panel involved in epigenetic modulation were found to be down-regulated in the case group with MIE: WHSC1L1, which encodes a histone lysine methyltransferase; and SMARCA4, which encodes an ATP-dependent helicase related to the SWI/SNF chromatin remodeling factor. A multitude of differentially expressed genes encoding histone post-translational modifiers as well as key components of the nucleosome remodeling complex mediating ATP-dependent nucleosome sliding, including SMARCC1, SMARCA4, CHD2 and CHD9, were down-regulated (Table 11). Other notable histone methyltransferases/demethylases differentially expressed include KDM4, KDM5C, KDM6, PRDM5, SETD2, SETDB2, and SUZI2. Genes coding for histone deacetylases/acetyltransferases and associated factors including HDAC9, KAT6A and EP400 were down-regulated and histone acetylation recognizing bromodomain containing protein, BRD2, was upregulated in the case group. Furthermore, critical non-histone heterochromatin proteins HP1-α and -γ were down-regulated, as well as core histone cluster. Taken together, our data may suggest a global loss of heterochromatin and genome instability, as well as probable gene-specific transcriptional deregulation in hyper-susceptible patients compared to controls.

Discussion

The work presented reports novel predictive models for hyper-susceptibility to infection among, e.g., traumatically injured patients, using genomic biomarkers and/or clinical characteristics that have not been used to build statistical prognostic models for the purpose of predicting infection outcomes. Evidence is provided that these models can identify burn patients at high risk of developing repeated infections indicative of their hyper-susceptible state. To our knowledge, this work is the first to describe such models in trauma patients, and the first to describe functional transcriptome data of burn patients in relation to infections. The prediction accuracy of hyper-susceptibility to MIE is significantly increased over clinical markers when the genomic signature is used, providing strong evidence of the promising role of genomic biomarkers in prognosis even when used alone. By combining the biomarker panel with clinical characteristics, even better prediction accuracy is provided, supporting the applicability of using genomic signature to increase confidence in data used for treatment decision-making.

Clinical Implications.

Two distinct patient groups with different genomic signatures and clinical characteristics were identified, essentially allowing the rapid identification of patients with a high risk of developing MIE following burn trauma. Although burn patients generally suffer from immunosuppression, clinical experience and the present data suggest that the severity of immunosuppression and infection outcome vary. These data suggest that patients can receive personalized therapy depending on their susceptibility to infection, e.g., triaged by physical exam and a blood test on admission. This information can facilitate the determination of appropriate treatment courses, particularly in regards to antibiotic use, allowing for selective use of prophylactic antibiotics and more objective justification of length of treatment courses. For the patient, this can limit complications related to unneeded antibiotics, reduce the burden of lines needed to deliver the antibiotics, and streamline hospital care. For the population, this can promote antibiotic stewardship, help stem the emergence of resistant organisms, and reduce the cost of care.

Mechanistic Aspects.

Genomic signatures provide insight into the molecular mechanisms of the more susceptible health status, and may aid in the discovery of novel therapeutic targets. The present findings point to novel potential targets for the prevention and/or early treatment of infections. Functional analyses of the 1142 biomarker candidates suggest new aspects into the pathophysiology of susceptibility to MIE after trauma. Susceptibility to MIE was associated with early alterations in numerous signaling pathways related to innate and adaptive immune responses, and changes in epigenetic modulation and metabolism.

Presented herein is evidence for increased chemotaxis, cell adhesion, and migration of immune cells, and simultaneously, decreased expansion of immune cells and development of lymphatic system components. Without wishing to be bound by theory, this seeming contradiction may well be the consequences of dysfunctional immune system and cytokine signaling, especially in T-cells.

The present data indicate that epigenetic changes occur early on, rather than mainly as a consequence of septic shock. Epigenetic regulation of immune system is a common mechanism for gene expression regulation and it plays a role in long-term immunosuppression after sepsis.[46] Tightly regulated chromatin remodeling is required for transcriptional regulation, which is vital for proper host immune and inflammatory responses.[47] Among the genes associated with epigenetic regulations, several have confirmed roles in immune responses, such as KAT6A and KDM6B (Table 11).[46,48-50] Furthermore, the data further supports the notion that genes related to cell-cycle control and DNA repair have roles in both immune responses and tumorigenesis. Without wishing to be bound by theory, the dramatic epigenetic changes could potentially explain the biomarker panel could predict MIE that occurred weeks later, and the underlying mechanisms that favor infections by Gram-negative opportunistic pathogens.

appropriate biomarkers and additional information regarding patient health status might be essential for successful clinical trials of anti-sepsis drugs.[21,22] Identification of the hyper-susceptible patients could enable more focused study design when expensive/invasive interventions, such as for the testing of cutting-edge technologies or products are involved by directing intervention to those who need it most. Identification of this group early after admission could also allow adjunctive treatments such as immunotherapy, extracorporeal lipopolysaccharide removal, and other novel treatments to be tested prior to the decline of the patient's clinical status due to MIE.

In some embodiments, described herein is a comprehensive diagnostic tool set will depend on the integration of genomic signatures of both host and pathogen. The blood biomarkers reported could be integrated with other diagnostic tools, such as genomic single nucleotide polymorphisms (SNPs) that predispose certain patients to infection,[51,52]. Physician decisions rely heavily on blood tests over the course of recovery, and a positive culture is still the most accepted and reliable method for diagnosing infection. Using biomarkers, these blood samples could also allow monitoring of the changes in susceptibility status and adjustment of treatments accordingly. Modern molecular based microbiological tests,[53] such as detection of P. aeruginosa in wound biopsy using RT-PCR based assays,[54] have been develope. Several molecular early detection kits have become commercially available for diagnosing common bloodstream infections, and have been found to show some promise despite of much room left for improvement.[55,56] The presently described biomarkers on the host response can work synergistically with these tests to support physician decisions.

The definition of hyper-susceptibility is based on natural definition of having repeated infections. Changing this definition, for example, to having at least three infection episodes, did not significantly change the biomarkers identified (data not shown).

Although this work and focused on thermally injured trauma patients, the approach is applicable to other types of trauma and surgical patients.

REFERENCES

1. Morris J A, MacKenzie E J, Damiano A M, et al. Mortality in trauma patients: the interaction between host factors and severity. J Trauma. 1990; 30:1476-1482.
2. Kraft R, Herndon D N, Al-Mousawi A M, et al. Burn size and survival probability in paediatric patients in modern burn care: a prospective observational cohort study. Lancet. 2012; 379:1013-1021.
3. Ryan C M, Schoenfeld D A, Thorpe W P, et al. Objective estimates of the probability of death from burn injuries. The New England journal of medicine. 1998; 338:362-366.
4. Osler T, Glance L, Buzas J S, et al. A trauma mortality prediction model based on the anatomic injury scale. Ann Surg. 2008; 247:1041-8.
5. MacKenzie E J, Rivara F P, Jurkovich G J, et al. A National Evaluation of the Effect of Trauma-Center Care on Mortality. N Engl J Med. 2006; 354:366-378.
6. Church D, Elsayed S, Reid O, et al. Burn wound infections. Clin Microbiol Rev. 2006; 19:403-434.
7. Bloemsma G C, Dokter J, Boxma H, et al. Mortality and causes of death in a burn centre. Burns. 2008; 34:1103-1107.
8. Ingraham A M, Xiong W, Hemmila M R, et al. The attributable mortality and length of stay of trauma-related complications: a matched cohort study. Ann Surg. 2010; 252:358-62.
9. Kesarwani M, Hazan R, He J, et al. A quorum sensing regulated small volatile molecule reduces acute virulence and promotes chronic infection phenotypes. PLoS pathogens. 2011; 7:e1002192.
10. Bandyopadhaya A, Kesarwani M, Que Y-A, et al. The quorum sensing volatile molecule 2-amino acetophenon modulates host immune responses in a manner that promotes life with unwanted guests. PLoS pathogens. 2012; 8:e1003024.
11. Boucher H W, Talbot G H, Bradley J S, et al. Bad bugs, no drugs: no ESKAPE! An update from the Infectious Diseases Society of America. Clin Infect Dis. 2009; 48:1-12.
12. Avni T, Levcovich A, Ad-El D D, et al. Prophylactic antibiotics for burns patients: systematic review and meta-analysis. BMJ (Clinical research ed). 2010; 340:c241.
13. Cohen N R, Lobritz M A, and Collins J J. Microbial Persistence and the Road to Drug Resistance. Cell Host & Microbe. 2013; 13:632-642.
14. Pirnay J-P, De Vos D, Cochez C, et al. Molecular Epidemiology of Pseudomonas aeruginosa Colonization in a Burn Unit: Persistence of a Multidrug-Resistant Clone and a Silver Sulfadiazine-Resistant Clone. Journal of Clinical Microbiology. 2003; 41:1192-1202.
15. De Vos D, Lim A Jr, Pirnay P, et al. Analysis of epidemic Pseudomonas aeruginosa isolates by isoelectric focusing of pyoverdine and RAPD-PCR: modern tools for an integrated anti-nosocomial infection strategy in burn wound centres [Internet]. Burns. 1997; 23:379-386.
16. Brunkhorst F M, Oppert M, Marx G, et al. Effect of empirical treatment with moxifloxacin and meropenem vs meropenem on sepsis-related organ dysfunction in patients with severe sepsis: a randomized trial. *JAMA: the journal of the American Medical Association.* 2012; 307: 2390-2399.
17. Schuetz P, Litke A, Albrich W C, et al. Blood biomarkers for personalized treatment and patient management decisions in community-acquired pneumonia. *Curr Opin Infect Dis.* 2013; 26:159-67.
18. Härtel C, Deuster M, Lehrnbecher T, et al. Current approaches for risk stratification of infectious complications in pediatric oncology. *Pediatr Blood Cancer.* 2007; 49:767-73.
19. Angus D C. The search for effective therapy for sepsis: back to the drawing board? *JAMA: the journal of the American Medical Association.* 2011; 306:2614-2615.
20. Kuehn B M. Guideline Promotes Early, Aggressive Sepsis Treatment to Boost Survival. *JAMA.* 2013; 309: 969-970.
21. Schuetz P, Haubitz S, and Mueller B. Do sepsis biomarkers in the emergency room allow transition from bundled sepsis care to personalized patient care? *Curr Opin Crit Care.* 2012; 18:341-9.
22. Angus D C, and van der Poll T. Severe sepsis and septic shock. *The New England journal of medicine.* 2013; 369:840-851.
23. Nichols R L, Smith J W, Klein D B, et al. Risk of infection after penetrating abdominal trauma. *The New England journal of medicine.* 1984; 311:1065-1070.
24. Kisat M, Villegas C V, Onguti S, et al. Predictors of sepsis in moderately severely injured patients: an analysis of the national trauma data bank. *Surgical infections.* 2013; 14:62-68.
25. Wibbenmeyer L, Danks R, Faucher L, et al. Prospective analysis of nosocomial infection rates, antibiotic use, and patterns of resistance in a burn population. *J Burn Care Res.* 2006; 27:152-160.
26. Boomer J S, To K, Chang K C, et al. Immunosuppression in patients who die of sepsis and multiple organ failure. *JAMA: the journal of the American Medical Association.* 2011; 306:2594-2605.
27. Lavrentieva A, Papadopoulou S, Kioumis J, et al. PCT as a diagnostic and prognostic tool in burn patients. Whether time course has a role in monitoring sepsis treatment. *Burns.* 2012; 38:356-363.
28. Schultz L, Walker S A N, Elligsen M, et al. Identification of predictors of early infection in acute burn patients. *Burns.* 2013; 39:1355-1366.
29. Cuenca A G, Gentile L F, Lopez M C, et al. Development of a Genomic Metric That Can Be Rapidly Used to Predict Clinical Outcome in Severely Injured Trauma Patients. *Crit Care Med.* 2013; 41:1175-85.
30. Laudanski K, Miller-Graziano C, Xiao W, et al. Cell-specific expression and pathway analyses reveal alterations in trauma-related human T cell and monocyte pathways. *Proc Natl Acad Sci USA.* 2006; 103:15564-15569.
31. Xiao W, Mindrinos M N, Seok J, et al. A genomic storm in critically injured humans. *The Journal of experimental medicine.* 2011; 208:2581-2590.
32. Jeschke M G, Finnerty C C, Emdad F, et al. Mild Obesity Is Protective After Severe Burn Injury. *Annals of surgery.* 2013; Publish Ahead of Print: 1.
33. Wu Z, Irizarry R A, Gentleman R, et al. A model based background adjustment for oligonucleotide expression arrays. *Johns Hopkins University, Dept. of Biostatistics Working Papers.* 2004;
34. Gentleman R C, Carey V J, Bates D M, et al. Bioconductor: open software development for computational biology and bioinformatics. *Genome Biology.* 2004; 5:R80.
35. Kauffmann A, Gentleman R, and Huber W. arrayQualityMetrics—a bioconductor package for quality assessment of microarray data. *Bioinformatics.* 2009; 25:415-416.
36. Servant N, Gravier E, Gestraud P, et al. EMA—A R package for Easy Microarray data analysis. *BMC research notes.* 2010; 3:277.
37. Smyth G K. Linear models and empirical bayes methods for assessing differential expression in microarray experiments. *Stat Appl Genet Mol Biol.* 2004; 3:Article3.
38. Tibshirani R. Regression Shrinkage and Selection via the Lasso. *Journal of the Royal Statistical Society. Series B (Methodological).* 1996; 58:267-288.
39. Friedman J, Hastie T, and Tibshirani R. Regularization Paths for Generalized Linear Models via Coordinate Descent. *Journal of statistical software.* 2010; 33:1-22.
40. Huang D W, Sherman B T, Stephens R, et al. DAVID gene ID conversion tool. *Bioinformation.* 2008; 2:428-430.
41. Wacharasint P, Boyd J H, Russell J A, et al. One size does not fit all in severe infection: obesity alters outcome, susceptibility, treatment, and inflammatory response. *Crit Care.* 2013; 17:R122.
42. Johnson C A, Kleshchenko Y Y, Ikejiani A O, et al. Thrombospondin-1 Interacts with *Trypanosoma cruzi* Surface Calreticulin to Enhance Cellular Infection. *PLoS One.* 2012; 7:e40614.
43. McMaken S, Exline M C, Mehta P, et al. Thrombospondin-1 Contributes to Mortality in Murine Sepsis through Effects on Innate Immunity. *PLoS One.* 2011; 6:e19654.
44. Streit M, Velasco P, Riccardi L, et al. Thrombospondin-1 suppresses wound healing and granulation tissue formation in the skin of transgenic mice. *The EMBO journal.* 2000; 19:3272-3282.
45. Shannon O. Platelets interact with bacterial pathogens. *Thrombosis and Haemostasis.* 2009; 102:613-4.
46. Carson W F, Cavassani K A, Dou Y, et al. Epigenetic regulation of immune cell functions during post-septic immunosuppression. *Epigenetics: official journal of the DNA Methylation Society.* 2011; 6:273-283.
47. Smale S T. Selective transcription in response to an inflammatory stimulus. *Cell.* 2010; 140:833-844.
48. Perez-Campo F M, Costa G, Lie-a-Ling M, et al. The MYSTerious MOZ, a histone acetyltransferase with a key role in haematopoiesis. *Immunology.* 2013; 139:161-165.
49. De Santa F, Narang V, Yap Z H, et al. Jmjd3 contributes to the control of gene expression in LPS-activated macrophages. *The EMBO journal.* 2009; 28:3341-3352.
50. Kruidenier L, Chung C-W, Cheng Z, et al. A selective jumonji H3K27 demethylase inhibitor modulates the proinflammatory macrophage response. *Nature.* 2012; 488:404-408.
51. Netea M G, Wijmenga C, and O'Neill L A J. Genetic variation in Toll-like receptors and disease susceptibility. *Nature Immunology.* 2012; 13:535-542.
52. Bronkhorst MWGA, Lomax M A Z, Vossen RHAM, et al. Risk of infection and sepsis in severely injured patients related to single nucleotide polymorphisms in the lectin pathway. *British Journal of Surgery.* 2013; 100:1818-1826.

53. Jannes G, and De Vos D. A review of current and future molecular diagnostic tests for use in the microbiology laboratory. *Methods Mol Biol.* 2006; 345:1-21.
54. Pirnay J-P, De Vos D, Duinslaeger L, et al. Quantitation of *Pseudomonas aeruginosa* in wound biopsy samples: from bacterial culture to rapid 'real-time' polymerase chain reaction. *Crit Care.* 2000; 4:255.
55. Chang S-S, Hsieh W-H, Liu T-S, et al. Multiplex PCR system for rapid detection of pathogens in patients with presumed sepsis—a systemic review and meta-analysis. *PLoS One.* 2013; 8:e62323.
56. Skvarc M, Stubljar D, Rogina P, et al. Non-culture-based methods to diagnose bloodstream infection: Does it work? *Eur J Microbiol Immunol* (Bp). 2013; 3:97-104.
57. Apidianakis Y, Que Y A, Xu W, et al. Down-regulation of glutatione S-transferase 4 (hGSTA4) in the muscle of thermally injured patients is indicative of susceptibility to bacterial infection. *The FASEB Journal.* 2012; 26:730-737.

TABLE 1

Demographics and characteristics of participants

| | All (n = 113) | Controls (≤1 Infections Episodes) (n = 47) | Cases (≥2 Infections Episodes [MIE]) (n = 66) | P value |
|---|---|---|---|---|
| Age when injured, mean (SD), y | 37.7 (15.6) | 37.0 (14.6) | 38.2 (16.4) | 0.681 |
| Sex, n (%) males | 90 (79.6%) | 40 (85.1%) | 50 (75.8%) | 0.218 |
| BMI Category, n (%) | | | | 0.888 |
| Underweight | 5 (4.4%) | 1 (2.1%) | 4 (6.1%) | |
| Healthy | 44 (38.9%) | 19 (40.4%) | 25 (37.9%) | |
| Overweight | 35 (31.0%) | 15 (31.9%) | 20 (30.3%) | |
| Obese | 29 (25.7%) | 12 (25.6%) | 17 (25.8%) | |
| Severity of Injury | | | | |
| APACHE II Score, median (IQR) | 20 (12-26) | 13 (8-20) | 24 (18-28) | <0.001* |
| Burns size of TBSA, % (IQR) | 40 (28-56) | 32 (23-40) | 46 (35-70) | <0.001* |
| Presence of Inhalation Injury, n (%) | 49 (43.4%) | 8 (17.0%) | 41 (62.1%) | <0.001* |
| Outcome | | | | |
| Hospital Stay, d (IQR) | 35 (19-62) | 20 (15-27) | 60 (33-71) | <0.001* |
| Hospital Stay of Survived, d (IQR) | 36 (19-62) | 20.5 (15-27) | 61 (44-72) | <0.001* |
| Days on Ventilation, d (IQR) | 13 (2-33) | 2 (0-5) | 28 (13-40) | <0.001* |
| Day of Death Since Injury, d (IQR) | 34 (18-63) | 21 (18-21) | 35.5 (18-65) | 0.3753 |
| Mortality, no. (%) | 21 (18.6%) | 3 (6.38%) | 18 (27.3%) | 0.0029* |
| Number of Records by Type of Infection, n (%) | | | | |
| Burn wound | 332 (54.2%) | 24 (60%) | 308 (53.8%) | |
| Pneumonia | 151 (24.7%) | 8 (20%) | 143 (25.0%) | |
| Bloodstream | 59 (9.6%) | 1 (2.5%) | 58 (10.1%) | |
| Urinary tract | 45 (7.4%) | 7 (17.5%) | 38 (6.6%) | |
| Catheter-related bloodstream | 24 (3.9%) | 0 (0%) | 24 (4.2%) | |
| *Pseudomembranous colitis* | 1 (0.2%) | 0 (0%) | 1 (0.2%) | |
| Number of Records by Isolated Pathogens, n (%) | | | | |
| *P. aeruginosa* | 92 (15.0%) | 4 (10%) | 88 (15.4%) | |
| *S. aureus* | 81 (13.2%) | 7 (17.5%) | 74 (13.0%) | |
| Coagulase negative Staphylococci | 77 (12.6%) | 6 (15.0%) | 71 (12.4%) | |
| *Enterococcus* | 47 (7.7%) | 4 (10.0%) | 43 (7.5%) | |
| *Acinetobacter* | 45 (7.4%) | 1 (2.5%) | 44 (7.7%) | |
| *Candida* species | 43 (7.0%) | 0 (0%) | 43 (7.5%) | |
| *E. coli* | 34 (5.6%) | 1 (2.5%) | 33 (5.8%) | |
| *Enterobacter* species | 28 (4.6%) | 1 (2.5%) | 27 (4.7%) | |
| Gram negative NOS | 27 (4.4%) | 0 (0%) | 27 (4.7%) | |
| *K. pneumoniae* | 22 (3.6%) | 0 (0%) | 22 (3.8%) | |
| Others | 116 (18.9%) | 16 (40%) | 100 (17.5%) | |

*P < 0.05.
Abbreviations:
BMI, body mass index;
IQR, inter-quartile range;
TBSA, total body surface area.

TABLE 2

14 probe sets in the biomarker panel

| Probe set | Gene Symbol | Gene Name | Gene Ontology Biological Process Annotation | Fold Change | Coefficients | P value |
|---|---|---|---|---|---|---|
| *Upregulated* | | | | | | |
| 201109_s_at | THBS1 | thrombospondin 1 | Angiogenesis, regulation of cytokine production, regulation of endothelial cell proliferation, regulation of antigen processing and presentation, regulation of immune system process | 3.37 | 0.560 | <0.001 |
| 201110_s_at | THBS1 | thrombospondin 1 | Same as above | 2.31 | 0.100 | 0.001 |
| 201108_s_at | THBS1 | thrombospondin 1 | Same as above | 2.02 | 0.824 | 0.001 |
| 235412_at | ARHGEF7 | Rho guanine nucleotide exchange factor (GEF) 7 | Apoptotic process, signal transduction, epidermal growth factor receptor signaling pathway, small GTPase mediated signal transduction, apoptotic signaling pathway, lamellipodium assembly | 1.86 | 0.747 | 0.017 |
| *Down-regulated* | | | | | | |
| 217599_s_at | MDFIC | MyoD family inhibitor domain containing | Transcription, activation of JUN kinase activity, virus-host interaction, regulation of Wnt receptor signaling pathway, negative regulation of protein import into nucleus, positive regulation of viral transcription | −2.34 | −0.289 | <0.001 |
| 200951_s_at | CCND2 | cyclin D2 | Positive regulation of cyclin-dependent protein kinase activity, cell cycle, cell division | −2.21 | 0.292 | <0.001 |
| 228986_at | OSBPL8 | oxysterol binding protein-like 8 | Lipid transport, negative regulation of sequestering of triglyceride, fat cell differentiation | −1.98 | 0.111 | <0.001 |
| 224730_at | DCAF7 | DDB1 and CUL4 associated factor 7 | Multicellular organismal development, protein ubiquitination | −1.87 | −0.908 | <0.001 |
| 222907_x_at | TMEM50B | transmembrane protein 50B | NA | −1.80 | −0.335 | <0.001 |
| 208797_s_at | GOLGA8A/GOLGA8B | golgin A8 family, member B | NA | −1.78 | −1.068 | <0.001 |
| 217656_at | SMARCA4 | SWI/SNF related, matrix associated, actin dependent regulator of chromatin, subfamily a, member 4 | Negative regulation of transcription from RNA polymerase II promoter, chromatin remodeling, negative regulation of cell growth, negative regulation of androgen receptor signaling pathway, etc. | −1.59 | 0.252 | <0.001 |
| 221248_s_at | WHSC1L1 | Wolf-Hirschhorn syndrome candidate 1-like 1 | Transcription, regulation of transcription, cell growth, histone methylation, cell differentiation, histone lysine methylation | −1.51 | −0.676 | <0.001 |
| 1556747_a_at | NA | NA | NA | −1.66 | −0.786 | 0.005 |
| 1562957_at | NA | NA | NA | −1.64 | −0.409 | <0.001 |

P values were adjusted for multiple comparisons based on Benjamini-Hechberg method during the fold-change calculation of 26,107 probes after initial filtering (see Methods).

TABLE 3

Predicted early functional changes in case group that had MIE

| Functions annotation | P value | Activation z-score | # of genes |
|---|---|---|---|
| *Increased* | | | |
| Chemotaxis | <0.001 | 3.924 | 55 |
| Chemotaxis of cells | <0.001 | 3.924 | 54 |
| Homing of cells | <0.001 | 3.815 | 59 |
| Chemotaxis of leukocytes | <0.001 | 3.795 | 37 |
| Chemotaxis of phagocytes | <0.001 | 3.546 | 30 |
| Chemotaxis of myeloid cells | <0.001 | 3.501 | 29 |
| Homing of leukocytes | <0.001 | 3.484 | 41 |
| Replication of Influenza A virus | <0.001 | 3.413 | 38 |
| Replication of virus | <0.001 | 3.314 | 64 |
| Leukocyte migration | <0.001 | 3.088 | 100 |
| Inflammatory response | <0.001 | 3.085 | 72 |
| Viral infection | <0.001 | 3.046 | 166 |
| Cytostasis | <0.001 | 2.913 | 30 |
| Replication of RNA virus | <0.001 | 2.782 | 56 |
| Cell movement | <0.001 | 2.766 | 173 |
| Migration of cells | <0.001 | 2.619 | 161 |
| Tyrosine phosphorylation of protein | <0.001 | 2.456 | 29 |
| Recruitment of cells | <0.001 | 2.451 | 34 |
| Recruitment of granulocytes | <0.001 | 2.405 | 26 |
| Polarization of leukocytes | <0.001 | 2.337 | 13 |

TABLE 3-continued

Predicted early functional changes in case group that had MIE

| Functions annotation | P value | Activation z-score | # of genes |
|---|---|---|---|
| Recruitment of leukocytes | <0.001 | 2.333 | 33 |
| Adhesion of immune cells | <0.001 | 2.271 | 40 |
| Recruitment of myeloid cells | <0.001 | 2.263 | 27 |
| Adhesion of blood cells | <0.001 | 2.250 | 41 |
| Cell viability | <0.001 | 2.240 | 112 |
| Orientation of macrophages | <0.001 | 2.200 | 6 |
| Attachment of cells | <0.001 | 2.166 | 18 |
| Disassembly of focal adhesions | <0.001 | 2.164 | 7 |
| Formation of membrane ruffles | <0.001 | 2.137 | 12 |
| Cell survival | <0.001 | 2.101 | 121 |
| Cell movement of neutrophils | <0.001 | 2.067 | 37 |
| Invasion of breast cancer cell lines | <0.001 | 2.064 | 25 |
| Orientation of cells | <0.001 | 2.028 | 19 |
| Decreased | <0.001 | | |
| Development of lymphoid organ | <0.001 | −3.241 | 30 |
| Development of lymphatic system component | <0.001 | −2.970 | 41 |
| Bacterial infection | <0.001 | −2.890 | 47 |
| Expansion of leukocytes | <0.001 | −2.753 | 25 |
| Expansion of lymphocytes | <0.001 | −2.635 | 21 |
| Development of lymph node | <0.001 | −2.608 | 14 |
| Morphology of germinal center | <0.001 | −2.415 | 11 |
| Morphology of lymph follicle | <0.001 | −2.415 | 15 |
| Expansion of blood cells | <0.001 | −2.384 | 26 |
| Encephalitis | <0.001 | −2.374 | 27 |
| Inflammation of organ | <0.001 | −2.362 | 97 |
| Quantity of neutrophils | 0.0011 | −2.208 | 23 |
| Development of thymocytes | <0.001 | −2.189 | 13 |
| Quantity of granulocytes | <0.001 | −2.133 | 36 |
| Organismal death | <0.001 | −2.074 | 196 |

An absolute z-score of ≥2 was designated as significant by the IPA software. The numbers of genes used to predict functional changes are indicated in the column with the heading "# of genes".

TABLE 11

Genes involved in epigenetic modulation and chromatin remodeling from the 1142 probe sets. Adjusted P value is based on B-H method. Gene symbols in bold are the genes that are part of the biomarker panel.

| ID | Symbol | Gene Name | Fold Change | Adjusted P value |
|---|---|---|---|---|
| 201715_s_at | ACIN1 | apoptotic chromatin condensation inducer 1 | 1.833 | 0.029 |
| 1553685_s_at | SP1 | Sp1 transcription factor | 1.832 | 0.030 |
| 41386_i_at | KDM6B | lysine (K)-specific demethylase 6B | 1.767 | 0.019 |
| 208686_s_at | BRD2 | bromodomain containing 2 | 1.614 | 0.086 |
| 213146_at | KDM6B | lysine (K)-specific demethylase 6B | 1.607 | 0.094 |
| 202383_at | KDM5C | lysine (K)-specific demethylase 5C | 1.548 | 0.010 |
| 215616_s_at | KDM4B | lysine (K)-specific demethylase 4B | 1.545 | 0.072 |
| 201353_s_at | BAZ2A | bromodomain adjacent to zinc finger domain, 2A | 1.503 | 0.022 |
| 210387_at | HIST2H2BE (includes others) | histone cluster 2, H2be | −1.506 | 0.075 |
| 228287_at | ING5 | inhibitor of growth family, member 5 | −1.507 | 0.011 |
| 225253_s_at | METTL2A | methyltransferase like 2A | −1.514 | 0.008 |
| 221248_s_at | WHSC1L1 | Wolf-Hirschhorn syndrome candidate 1-like 1 | −1.515 | 9.28E−05 |
| 218166_s_at | RSF1 | remodeling and spacing factor 1 | −1.516 | 0.002 |
| 231913_s_at | BRCC3 | BRCA1/BRCA2-containing complex, subunit 3 | −1.523 | 0.002 |
| 239784_at | NA | NA | −1.526 | 0.000 |
| 209715_at | CBX5 (HP1alpha) | chromobox homolog 5 | −1.532 | 0.003 |
| 213971_s_at | SUZ12 | suppressor of zeste 12 homolog (*Drosophila*) | −1.534 | 0.001 |
| 203204_s_at | KDM4A | lysine (K)-specific demethylase 4A | −1.565 | 4.86E−04 |
| 205659_at | HDAC9 | histone deacetylase 9 | −1.573 | 0.004 |
| 217656_at | SMARCA4 | SWI/SNF related, matrix associated, actin dependent regulator of chromatin, subfamily a, member 4 | −1.590 | 5.77E−05 |
| 243552_at | MBTD1 | mbt domain containing 1 | −1.591 | 0.002 |
| 244443_at | CHD2 | chromodomain helicase DNA binding protein 2 | −1.610 | 0.013 |
| 1554667_s_at | METTL8 | methyltransferase like 8 | −1.610 | 0.003 |
| 216521_s_at | BRCC3 | BRCA1/BRCA2-containing complex, subunit 3 | −1.613 | 0.002 |
| 235338_s_at | SETDB2 | SET domain, bifurcated 2 | −1.617 | 3.46E−04 |
| 1569385_s_at | TET2 | tet methylcytosine dioxygenase 2 | −1.630 | 0.012 |
| 229586_at | CHD9 | chromodomain helicase DNA binding protein 9 | −1.632 | 0.001 |
| 225455_at | TADA1 | transcriptional adaptor 1 | −1.654 | 0.001 |
| 201072_s_at | SMARCC1 | SWI/SNF related, matrix associated, actin dependent regulator of chromatin, subfamily c, member 1 | −1.657 | 1.44E−04 |
| 220792_at | PRDM5 | PR domain containing 5 | −1.738 | 0.005 |
| 207156_at | HIST1H2AG (includes others) | histone cluster 1, H2ag | −1.742 | 0.009 |
| 227075_at | ELP3 | elongator acetyltransferase complex subunit 3 | −1.756 | 0.003 |
| 238220_at | KDM6A | lysine (K)-specific demethylase 6A | −1.761 | 0.004 |
| 1555920_at | CBX3 (HP1gamma) | chromobox homolog 3 | −1.838 | 0.001 |
| 222873_s_at | EHMT1 | euchromatic histone-lysine N-methyltransferase 1 | −1.868 | 6.92E−05 |
| 230629_s_at | EP400 | E1A binding protein p400 | −1.987 | 2.38E−04 |
| 216361_s_at | KAT6A | K(lysine) acetyltransferase 6A | −2.018 | 0.010 |
| 220946_s_at | SETD2 | SET domain containing 2 | −2.048 | 7.65E−05 |
| 216069_at | PRMT2 | protein arginine methyltransferase 2 | −2.085 | 0.006 |
| 242918_at | NASP | nuclear autoantigenic sperm protein (histone-binding) | −2.098 | 2.62E−04 |

TABLE 11-continued

Genes involved in epigenetic modulation and chromatin remodeling from the 1142 probe sets. Adjusted P value is based on B-H method. Gene symbols in bold are the genes that are part of the biomarker panel.

| ID | Symbol | Gene Name | Fold Change | Adjusted P value |
|---|---|---|---|---|
| 203056_s_at | PRDM2 | PR domain containing 2, with ZNF domain | −2.164 | 1.44E−04 |
| 235461_at | TET2 | tet methylcytosine dioxygenase 2 | −2.912 | 0.001 |

Adjusted P value is based on B-H method. Gene symbols in bold are the genes that are part of the biomarker panel.

TABLE 12

Estimates of multivariate logistic regression models.

| Covariates | Estimates | Standard Error | P value |
|---|---|---|---|
| Clinical Model | | | |
| Intercept | −1.9885 | 0.4735 | <.001 |
| TBSA | 0.0753 | 0.0186 | <.001 |
| Age | 0.0392 | 0.0169 | 0.0203 |
| Inhalation Injury (Yes) | 1.9376 | 0.5248 | <.001 |
| Genomic Model | | | |
| Intercept | 0.7449 | 0.3556 | 0.0362 |
| 1556747_a_at | −0.7855 | 0.383 | 0.0403 |
| 1562957_at | −0.4094 | 0.7305 | 0.5752 |
| 200951_s_at | 0.2915 | 0.6202 | 0.6383 |
| 201108_s_at | 0.8238 | 0.4333 | 0.0573 |
| 201109_s_at | 0.5597 | 0.4199 | 0.1826 |
| 201110_s_at | 0.0998 | 0.5276 | 0.85 |
| 208797_s_at | −1.0683 | 0.6742 | 0.113 |
| 217599_s_at | −0.2885 | 0.4856 | 0.5524 |
| 217656_at | 0.2524 | 0.8757 | 0.7732 |
| 221248_s_at | −0.6759 | 0.7991 | 0.3976 |
| 222907_x_at | −0.3347 | 0.7969 | 0.6745 |
| 224730_at | −0.9083 | 0.6465 | 0.1601 |
| 228986_at | 0.1106 | 0.5772 | 0.848 |
| 235412_at | 0.7468 | 0.2806 | 0.0078 |
| Combined Model | | | |
| Intercept | −1.1912 | 0.8375 | 0.1549 |
| TBSA | 0.0423 | 0.0254 | 0.0959 |
| Age | 0.0652 | 0.0412 | 0.1138 |
| Inhalation Injury (Yes) | 3.5132 | 1.3252 | 0.008 |
| 1556747_a_at | −0.6652 | 0.4794 | 0.1653 |
| 1562957_at | 0.803 | 1.139 | 0.4808 |
| 200951_s_at | 0.033 | 0.7811 | 0.9663 |
| 201108_s_at | 0.8321 | 0.5618 | 0.1385 |
| 201109_s_at | 0.8448 | 0.5465 | 0.1221 |
| 201110_s_at | 0.0714 | 0.6752 | 0.9158 |
| 208797_s_at | −0.731 | 0.785 | 0.3518 |
| 217599_s_at | −0.146 | 0.5532 | 0.7918 |
| 217656_at | −1.0108 | 1.2418 | 0.4157 |
| 221248_s_at | −1.2438 | 1.3393 | 0.353 |
| 222907_x_at | −0.167 | 0.9343 | 0.8582 |
| 224730_at | −1.4905 | 0.8 | 0.0625 |
| 228986_at | 0.1821 | 0.7275 | 0.8023 |
| 235412_at | 0.8709 | 0.3909 | 0.0259 |

TABLE 13

Term centric singular enrichment in gene ontology biological process and molecular function of the 1142 probe sets.

| GO Term | Count | % | Fold Enrichment | Adjusted P value | Immune | Epi | Transcription | Metabolism |
|---|---|---|---|---|---|---|---|---|
| BP GO:0001775~cell activation | 42 | 4.5 | 2.76 | 9.30E−06 | * | | | |
| BP GO:0007242~intracellular signaling cascade | 114 | 12.2 | 1.71 | 9.52E−06 | * | | | |
| BP GO:0045321~leukocyte activation | 38 | 4.1 | 2.96 | 1.63E−05 | ** | | | |
| BP GO:0016192~vesicle mediated transport | 64 | 6.9 | 2.09 | 2.33E−05 | * | | | |
| BP GO:0016568~chromatin modification | 37 | 4.0 | 2.54 | 2.66E−04 | | ** | | |
| BP GO:0046649~lymphocyte activation | 30 | 3.2 | 2.84 | 2.99E−04 | ** | | | |
| BP GO:0006897~endocytosis | 32 | 3.4 | 2.74 | 3.07E−04 | ** | | | |
| BP GO:0010324~membrane invagination | 32 | 3.4 | 2.74 | 3.07E−04 | * | | | |
| BP GO:0016044~membrane organization | 45 | 4.8 | 2.23 | 3.53E−04 | * | | | |
| BP GO:0010557~positive regulation of macromolecule biosynthetic process | 64 | 6.9 | 1.84 | 7.69E−04 | | | | ** |
| BP GO:0031328~positive regulation of cellular biosynthetic process | 66 | 7.1 | 1.82 | 8.02E−04 | | | | ** |
| BP GO:0042110~T cell activation | 22 | 2.4 | 3.29 | 8.36E−04 | ** | | | |
| BP GO:0007243~protein kinase cascade | 43 | 4.6 | 2.19 | 8.68E−04 | * | | | |
| BP GO:0006955~immune response | 66 | 7.1 | 1.80 | 9.34E−04 | ** | | | |
| BP GO:0009891~positive regulation of biosynthetic process | 66 | 7.1 | 1.79 | 0.001 | | | | ** |
| BP GO:0010604~positive regulation of macromolecule metabolic process | 77 | 8.3 | 1.69 | 0.001 | | | | ** |
| BP GO:0042981~regulation of apoptosis | 73 | 7.8 | 1.71 | 0.001 | * | | | |
| BP GO:0030036~actin cytoskeleton organization | 30 | 3.2 | 2.50 | 0.002 | | | | |
| BP GO:0018105~peptidyl-serine phosphorylation | 10 | 1.1 | 6.50 | 0.002 | | | * | |
| BP GO:0030029~actin filament-based process | 31 | 3.3 | 2.42 | 0.002 | | | | |

TABLE 13-continued

Term centric singular enrichment in gene ontology biological process and molecular function of the 1142 probe sets.

| GO Term | Count | % | Fold Enrichment | Adjusted P value | Immune | Epi | Transcription | Metabolism |
|---|---|---|---|---|---|---|---|---|
| BP GO:0006325~chromatin organization | 42 | 4.5 | 2.09 | 0.002 | | ** | | |
| BP GO:0010941~regulation of cell death | 73 | 7.8 | 1.69 | 0.002 | * | | | |
| BP GO:0043067~regulation of programmed cell death | 73 | 7.8 | 1.69 | 0.002 | * | | | |
| BP GO:0006793~phosphorus metabolic process | 84 | 9.0 | 1.63 | 0.002 | | | | ** |
| BP GO:0006796~phosphate metabolic process | 84 | 9.0 | 1.63 | 0.002 | | | | ** |
| BP GO:0016310~phosphorylation | 72 | 7.7 | 1.70 | 0.002 | | | | |
| MF GO:0019899~enzyme binding | 55 | 5.9 | 1.96 | 0.002 | | | | |
| BP GO:0046907~intracellular transport | 61 | 6.5 | 1.75 | 0.003 | | | | |
| BP GO:0018209~peptidyl-serine modification | 11 | 1.2 | 5.31 | 0.003 | | * | | |
| BP GO:0002684~positive regulation of immune system process | 30 | 3.2 | 2.37 | 0.003 | ** | | | |
| BP GO:0008219~cell death | 65 | 7.0 | 1.70 | 0.003 | | | | |
| BP GO:0016265~death | 65 | 7.0 | 1.69 | 0.004 | | | | |
| BP GO:0006468~protein amino acid phosphorylation | 61 | 6.5 | 1.72 | 0.004 | * | * | | |
| BP GO:0007265~Ras protein signal transduction | 18 | 1.9 | 3.23 | 0.004 | | | | |
| BP GO:0048534~hemopoietic or lymphoid organ development | 31 | 3.3 | 2.25 | 0.005 | ** | | | |
| BP GO:0051173~positive regulation of nitrogencompound metabolic process | 59 | 6.3 | 1.73 | 0.005 | | | | ** |
| BP GO:0045893~positive regulation of transcription, DNA-dependent | 47 | 5.0 | 1.86 | 0.005 | | | ** | |
| BP GO:0002694~regulation of leukocyte activation | 23 | 2.5 | 2.61 | 0.006 | ** | | | |
| BP GO:0051254~positive regulation of RNA metabolic process | 47 | 5.0 | 1.84 | 0.006 | | | ** | |
| BP GO:0012501~programmed cell death | 56 | 6.0 | 1.73 | 0.006 | * | | | |
| BP GO:0042325~regulation of phosphorylation | 46 | 4.9 | 1.86 | 0.006 | * | * | | |
| BP GO:0045935~positive regulation of nucleobase, nucleoside, nucleotide and nucleic acid metabolic process | 57 | 6.1 | 1.72 | 0.006 | | | ** | |
| BP GO:0018210~peptidyl-threonine modification | 8 | 0.9 | 7.18 | 0.006 | | * | | |
| BP GO:0007264~small GTPase mediated signal transduction | 34 | 3.6 | 2.10 | 0.006 | | | | |
| BP GO:0002263~cell activation during immune response | 10 | 1.1 | 5.23 | 0.006 | ** | | | |
| BP GO:00023664~leukocyte activation during immune response | 10 | 1.1 | 5.23 | 0.006 | ** | | | |
| BP GO:0051276~chromosome organization | 47 | 5.0 | 1.83 | 0.006 | | ** | | |
| BP GO:0051174~-regulation of phosphorus metabolic process | 47 | 5.0 | 1.83 | 0.006 | | | ** | |
| BP GO:0019220~regulation of phosphate metabolic process | 47 | 5.0 | 1.83 | 0.006 | | | ** | |
| BP GO:0045941~positive regulation of transcription | 52 | 5.6 | 1.74 | 0.009 | | | ** | |
| BP GO:0030097~hemopoiesis | 28 | 3.0 | 2.24 | 0.009 | ** | | | |
| BP GO:0060627~regulation of vesicle-mediated transport | 16 | 1.7 | 3.14 | 0.010 | * | | | |
| BP GO:0050865~regulation of cell activation | 23 | 2.5 | 2.48 | 0.010 | ** | | | |
| BP GO:0002520~immune system development | 31 | 3.3 | 2.12 | 0.010 | ** | | | |
| BP GO:0007568~aging | 17 | 1.8 | 2.91 | 0.014 | | | | |
| BP GO:0006357~regulation of transcription fromRNA polymerase II promoter | 62 | 6.6 | 1.61 | 0.014 | | | ** | |
| BP GO:0033674~positive regulation of kinase activity | 27 | 2.9 | 2.20 | 0.014 | * | | | |
| BP GO:0002252~immune effector process | 19 | 2.0 | 2.67 | 0.014 | ** | | | |
| BP GO:0008380~RNA splicing | 31 | 3.3 | 2.06 | 0.014 | | | ** | |
| BP GO:0018107-peptidyl-threonine phosphorylation | 7 | 0.8 | 7.33 | 0.014 | | * | | |
| BP GO:0009991~response to extracellular stimulus | 26 | 2.8 | 2.23 | 0.015 | * | | | * |
| BP GO:0010628~positive regulation of gene expression | 52 | 5.6 | 1.69 | 0.015 | | | | ** |

TABLE 13-continued

Term centric singular enrichment in gene ontology biological process and molecular function of the 1142 probe sets.

| GO Term | Count | % | Fold Enrichment | Adjusted P value | Immune | Epi | Transcription | Metabolism |
|---|---|---|---|---|---|---|---|---|
| MF GO:0003723~RNA binding | 65 | 7.0 | 1.69 | 0.015 | | * | * | |
| BP GO:0030098~lymphocyte differentiation | 16 | 1.7 | 2.93 | 0.017 | ** | | | |
| BP GO:0043549~regulation of kinase activity | 36 | 3.9 | 1.90 | 0.017 | * | | | |
| BP GO:0045860~positive regulation of protein kinase activity | 26 | 2.8 | 2.20 | 0.017 | * | | | |
| BP GO:0031667~response to nutrient levels | 24 | 2.6 | 2.30 | 0.017 | | | | ** |
| BP GO:0010033~response to organic substance | 61 | 6.5 | 1.59 | 0.017 | | | | ** |
| MF GO:0030695~GTPase regulator activity | 42 | 4.5 | 1.94 | 0.017 | | | | |
| BP GO:0044093~positive regulation of molecular function | 52 | 5.6 | 1.67 | 0.017 | | | | |
| BP GO:0007015~actin filament organization | 13 | 1.4 | 3.40 | 0.018 | * | | | |
| BP GO:0032268~regulation of cellular protein metabolic process | 44 | 4.7 | 1.75 | 0.019 | | | | ** |
| BP GO:0007584~response to nutrient | 19 | 2.0 | 2.56 | 0.020 | | | | ** |
| BP GO:0051347~positive regulation of transferase activity | 27 | 2.9 | 2.12 | 0.020 | | | | |
| MF GO:0060589~nucleoside-triphosphatase regulator activity | 42 | 4.5 | 1.90 | 0.021 | | | | |
| BP GO:0002696~positive regulation of leukocyte activation | 16 | 1.7 | 2.84 | 0.021 | ** | | | |
| MF GO:0032553~ribonucleotide binding | 133 | 14.3 | 1.35 | 0.021 | | | | * |
| MF GO:0032555~purine ribonucleotide binding | 133 | 14.3 | 1.35 | 0.021 | | | | |
| BP GO:0045597~positive regulation of cell differentiation | 26 | 2.8 | 2.14 | 0.022 | ** | | | |
| MF GO:0016278~lysine N-methyltransferase activity | 9 | 1.0 | 5.25 | 0.023 | | * | | |
| MF GO:0016279~protein-lysine Nmethyltransferase activity | 9 | 1.0 | 5.25 | 0.023 | | * | | |
| MF GO:0018024~histone-lysine Nmethyltransferase activity | 9 | 1.0 | 5.25 | 0.023 | | ** | | |
| BP GO:0051129~negative regulation of cellular component organization | 19 | 2.0 | 2.52 | 0.023 | | | | |
| MF GO:0042054~histone methyltransferase activity | 10 | 1.1 | 4.78 | 0.024 | | ** | | |
| MF GO:0000166~nucleotide binding | 158 | 16.9 | 1.31 | 0.024 | | | * | |
| BP GO:0002521~leukocyte differentiation | 18 | 1.9 | 2.59 | 0.024 | ** | | | |
| BP GO:0030217~T cell differentiation | 12 | 1.3 | 3.48 | 0.024 | ** | | | |
| BP GO:0001817~regulation of cytokine production | 22 | 2.4 | 2.29 | 0.026 | ** | | | |
| BP GO:0006915~apoptosis | 52 | 5.6 | 1.63 | 0.026 | * | | | |
| BP GO:0033273~response to vitamin | 12 | 1.3 | 3.43 | 0.026 | | | | ** |
| BP GO:0002819~regulation of adaptive immune response | 11 | 1.2 | 3.70 | 0.027 | ** | | | |
| BP GO:0007266~Rho protein signal transduction | 9 | 1.0 | 4.46 | 0.028 | | | | |
| BP GO:0051338~regulation of transferase activity | 36 | 3.9 | 1.82 | 0.028 | | | | |
| BP GO:0050867~positive regulation of cell activation | 16 | 1.7 | 2.72 | 0.029 | ** | | | |
| BP GO:0016197~endosome transport | 11 | 1.2 | 3.57 | 0.031 | * | | | |
| BP GO:0001932~regulation of protein amino acid phosphorylation | 21 | 2.3 | 2.29 | 0.032 | | | | |
| BP GO:0010608~posttranscriptional regulation of gene expression | 24 | 2.6 | 2.14 | 0.032 | | ** | ** | |
| BP GO:0051094~positive regulation of developmental process | 29 | 3.1 | 1.97 | 0.032 | ** | | | |
| BP GO:0010605~negative regulation of macromolecule metabolic process | 60 | 6.4 | 1.54 | 0.032 | ** | | | |
| MF GO:0005083~small GTPase regulator activity | 30 | 3.2 | 2.04 | 0.033 | | | ** | |
| BP GO:0045449~regulation of transcription | 172 | 18.4 | 1.25 | 0.035 | | | ** | |
| BP GO:0007010~cytoskeleton organization | 40 | 4.3 | 1.73 | 0.035 | * | | | |
| MF GO:0004674~protein serine/threonine kinase activity | 41 | 4.4 | 1.78 | 0.035 | | | | |
| MF GO:0051015~actin filament binding | 11 | 1.2 | 3.87 | 0.036 | * | | | |
| MF GO:0005524~ATP binding | 108 | 11.6 | 1.36 | 0.038 | | | | |
| MF GO:0016563~transcription activator activity | 39 | 4.2 | 1.77 | 0.040 | | | | ** |
| MF GO:0042802~identical protein binding | 55 | 5.9 | 1.60 | 0.041 | | | | |
| BP GO:0016071~mRNA metabolic process | 35 | 3.8 | 1.78 | 0.044 | | | | ** |

TABLE 13-continued

Term centric singular enrichment in gene ontology biological process and molecular function of the 1142 probe sets.

| GO Term | Count | % | Fold Enrichment | Adjusted P value | Immune | Epi | Transcription | Metabolism |
|---|---|---|---|---|---|---|---|---|
| BP GO:0043405~regulation of MAP kinase activity | 18 | 1.9 | 2.41 | 0.045 | ** | | | |
| BP GO:0050863~regulation of T cell activation | 16 | 1.7 | 2.58 | 0.045 | ** | | | |
| MF GO:0005070~SH3/SH2 adaptor activity | 10 | 1.1 | 3.81 | 0.047 | | | | |
| BP GO:0043065~positive regulation of apoptosis | 39 | 4.2 | 1.71 | 0.047 | * | | | |
| MF GO:0032559~adenyl ribonucleotide binding | 108 | 11.6 | 1.35 | 0.049 | | | | |
| MF GO:0017076~purine nucleotide binding | 133 | 14.3 | 1.29 | 0.049 | | | | |
| BP GO:0045859~regulation of protein kinase activity | 33 | 3.5 | 1.80 | 0.050 | | | | |

Abbreviations: BP, biological process; MF, molecular function. Adjusted P value is based on Benjamini method.
Asterisks indicate whether this term is associated with one of the four functional categories: immune responses, epigenetic modulation, transcription and metabolism.
* denotes associated; ** denotes highly associated; based on manual curation.

TABLE 14

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| Annotation Cluster 1 | | Enrichment Score: 6.51 | | | | | |
| BP | GO: 0016192~vesicle-mediated transport | 64 | 6.86 | 2.98E-08 | 2.33E-05 | 2.09 | 5.39E-05 |
| BP | GO: 0010324~membrane invagination | 32 | 3.43 | 5.90E-07 | 3.07E-04 | 2.74 | 1.07E-03 |
| BP | GO: 0006897~endocytosis | 32 | 3.43 | 5.90E-07 | 3.07E-04 | 2.74 | 1.07E-03 |
| BP | GO: 0016044~membrane organization | 45 | 4.82 | 9.05E-07 | 3.53E-04 | 2.23 | 1.64E-03 |
| Annotation Cluster 2 | | Enrichment Score: 4.53 | | | | | |
| BP | GO: 0045321~leukocyte activation | 38 | 4.07 | 5.21E-09 | 1.63E-05 | 2.96 | 9.42E-06 |
| BP | GO: 0001775~cell activation | 42 | 4.50 | 5.95E-09 | 9.30E-06 | 2.76 | 1.08E-05 |
| BP | GO: 0046649~lymphocyte activation | 30 | 3.22 | 6.71E-07 | 2.99E-04 | 2.84 | 1.21E-03 |
| BP | GO: 0042110~T cell activation | 22 | 2.36 | 2.68E-06 | 8.36E-04 | 3.29 | 4.85E-03 |
| BP | GO: 0048534~hemopoietic or lymphoid organ development | 31 | 3.32 | 4.96E-05 | 4.68E-03 | 2.25 | 0.09 |
| BP | GO: 0030097~hemopoiesis | 28 | 3.00 | 1.36E-04 | 9.38E-03 | 2.24 | 0.25 |
| BP | GO: 0002520~immune system development | 31 | 3.32 | 1.49E-04 | 9.82E-03 | 2.12 | 0.27 |
| BP | GO: 0030098~lymphocyte differentiation | 16 | 1.71 | 3.32E-04 | 1.66E-02 | 2.93 | 0.60 |
| BP | GO: 0002521~leukocyte differentiation | 18 | 1.93 | 5.50E-04 | 2.42E-02 | 2.59 | 0.99 |
| BP | GO: 0030217~T cell differentiation | 12 | 1.29 | 5.58E-04 | 2.43E-02 | 3.48 | 1.01 |
| BP | GO: 0042113~B cell activation | 11 | 1.18 | 6.61E-03 | 0.14 | 2.73 | 11.30 |
| BP | GO: 0030183~B cell differentiation | 8 | 0.86 | 0.01 | 0.21 | 3.14 | 20.52 |
| Annotation Cluster 3 | | Enrichment Score: 4.33 | | | | | |
| BP | GO: 0018105~peptidyl-serine phosphorylation | 10 | 1.07 | 1.21E-05 | 1.57E-03 | 6.50 | 0.02 |
| BP | GO: 0018209~peptidyl-serine modification | 11 | 1.18 | 2.57E-05 | 2.97E-03 | 5.31 | 0.05 |
| BP | GO: 0018210~peptidyl-threonine modification | 8 | 0.86 | 6.90E-05 | 5.97E-03 | 7.18 | 0.12 |
| BP | GO: 0018107~peptidyl-threonine phosphorylation | 7 | 0.75 | 2.33E-04 | 0.01 | 7.33 | 0.42 |
| Annotation Cluster 4 | | Enrichment Score: 4.11 | | | | | |
| BP | GO: 0030036~actin cytoskeleton organization | 30 | 3.22 | 9.00E-06 | 1.56E-03 | 2.50 | 0.02 |
| BP | GO: 0030029~actin filament-based process | 31 | 3.32 | 1.16E-05 | 1.57E-03 | 2.42 | 0.02 |
| BP | GO: 0007015~actin filament organization | 13 | 1.39 | 3.67E-04 | 0.02 | 3.40 | 0.66 |
| BP | GO: 0007010~cytoskeleton organization | 40 | 4.29 | 9.47E-04 | 0.03 | 1.73 | 1.70 |
| Annotation Cluster 5 | | Enrichment Score: 4.08 | | | | | |
| BP | GO: 0008219~cell death | 65 | 6.97 | 2.83E-05 | 3.16E-03 | 1.70 | 0.05 |
| BP | GO: 0016265~death | 65 | 6.97 | 3.50E-05 | 3.63E-03 | 1.69 | 0.06 |
| BP | GO: 0012501~programmed cell death | 56 | 6.00 | 7.74E-05 | 5.88E-03 | 1.73 | 0.14 |
| BP | GO: 0006915~apoptosis | 52 | 5.57 | 5.99E-04 | 0.03 | 1.63 | 1.08 |
| Annotation Cluster 6 | | Enrichment Score: 3.74 | | | | | |
| BP | GO: 0016568~chromatin modification | 37 | 3.97 | 4.25E-07 | 2.66E-04 | 2.54 | 7.69E-04 |
| BP | GO: 0006325~chromatin organization | 42 | 4.50 | 1.01E-05 | 1.58E-03 | 2.09 | 0.02 |
| BP | GO: 0051276~chromosome organization | 47 | 5.04 | 8.94E-05 | 6.47E-03 | 1.83 | 0.16 |
| BP | GO: 0016569~covalent chromatin modification | 16 | 1.71 | 2.72E-03 | 0.08 | 2.39 | 4.80 |
| BP | GO: 0016570~histone modification | 15 | 1.61 | 5.16E-03 | 0.12 | 2.32 | 8.94 |
| BP | GO: 0006730~one-carbon metabolic process | 14 | 1.50 | 6.27E-03 | 0.14 | 2.36 | 10.76 |
| Annotation Cluster 7 | | Enrichment Score: 3.54 | | | | | |
| BP | GO: 0006796~phosphate metabolic process | 84 | 9.00 | 8.98E-06 | 1.65E-03 | 1.63 | 0.02 |
| BP | GO: 0006793~phosphorus metabolic process | 84 | 9.00 | 8.98E-06 | 1.65E-03 | 1.63 | 0.02 |
| BP | GO: 0016310~phosphorylation | 72 | 7.72 | 1.12E-05 | 1.66E-03 | 1.70 | 0.02 |
| BP | GO: 0006468~protein amino acid phosphorylation | 61 | 6.54 | 3.71E-05 | 3.73E-03 | 1.72 | 0.07 |
| MF | GO: 0000166~nucleotide binding | 158 | 16.93 | 1.43E-04 | 0.02 | 1.31 | 0.22 |
| MF | GO: 0032553~ribonucleotide binding | 133 | 14.26 | 1.76E-04 | 0.02 | 1.35 | 0.27 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| MF | GO: 0032555~purine ribonucleotide binding | 133 | 14.26 | 1.76E-04 | 0.02 | 1.35 | 0.27 |
| MF | GO: 0004674~protein serine/threonine kinase activity | 41 | 4.39 | 4.62E-04 | 0.03 | 1.78 | 0.71 |
| MF | GO: 0005524~ATP binding | 108 | 11.58 | 6.02E-04 | 0.04 | 1.36 | 0.93 |
| MF | GO: 0032559~adenyl ribonucleotide binding | 108 | 11.58 | 9.54E-04 | 0.05 | 1.35 | 1.46 |
| MF | GO: 0017076~purine nucleotide binding | 133 | 14.26 | 1.02E-03 | 0.05 | 1.29 | 1.56 |
| MF | GO: 0004672~protein kinase activity | 50 | 5.36 | 2.57E-03 | 0.09 | 1.54 | 3.90 |
| MF | GO: 0001882~nucleoside binding | 111 | 11.90 | 3.86E-03 | 0.12 | 1.28 | 5.80 |
| MF | GO: 0001883~purine nucleoside binding | 110 | 11.79 | 4.30E-03 | 0.12 | 1.28 | 6.45 |
| MF | GO: 0030554~adenyl nucleotide binding | 108 | 11.58 | 5.30E-03 | 0.13 | 1.28 | 7.88 |
| Annotation Cluster 8 | Enrichment Score: 3.42 | | | | | | |
| BP | GO: 0010557~positive regulation of macromolecule biosynthetic process | 64 | 6.86 | 2.71E-06 | 7.69E-04 | 1.84 | 0.00 |
| BP | GO: 0031328~positive regulation of cellular biosynthetic process | 66 | 7.07 | 3.08E-06 | 8.02E-04 | 1.82 | 0.01 |
| BP | GO: 0009891~positive regulation of biosynthetic process | 66 | 7.07 | 5.00E-06 | 1.12E-03 | 1.79 | 0.01 |
| BP | GO: 0010604~positive regulation of macromolecule metabolic process | 77 | 8.25 | 5.58E-06 | 1.16E-03 | 1.69 | 0.01 |
| BP | GO: 0051173~positive regulation of nitrogen compound metabolic process | 59 | 6.32 | 4.88E-05 | 4.75E-03 | 1.73 | 0.09 |
| BP | GO: 0045893~positive regulation of transcription, DNA-dependent | 47 | 5.04 | 6.00E-05 | 5.50E-03 | 1.86 | 0.11 |
| BP | GO: 0045935~positive regulation of nucleobase, nucleoside, nucleotide and nucleic acid metabolic process | 57 | 6.11 | 7.28E-05 | 5.96E-03 | 1.72 | 0.13 |
| BP | GO: 0051254~positive regulation of RNA metabolic process | 47 | 5.04 | 7.35E-05 | 5.87E-03 | 1.84 | 0.13 |
| BP | GO: 0045941~positive regulation of transcription | 52 | 5.57 | 1.26E-04 | 8.93E-03 | 1.74 | 0.23 |
| BP | GO: 0006357~regulation of transcription from RNA polymerase II promoter | 62 | 6.65 | 2.35E-04 | 0.01 | 1.61 | 0.42 |
| BP | GO: 0010628~positive regulation of gene expression | 52 | 5.57 | 2.61E-04 | 0.01 | 1.69 | 0.47 |
| BP | GO: 0045449~regulation of transcription | 172 | 18.44 | 9.56E-04 | 0.03 | 1.25 | 1.72 |
| BP | GO: 0051252~regulation of RNA metabolic process | 124 | 13.29 | 1.93E-03 | 0.06 | 1.29 | 3.44 |
| BP | GO: 0045944~positive regulation of transcription from RNA polymerase II promoter | 33 | 3.54 | 4.56E-03 | 0.11 | 1.68 | 7.94 |
| BP | GO: 0006355~regulation of transcription, DNA-dependent | 118 | 12.65 | 6.39E-03 | 0.14 | 1.25 | 10.95 |
| BP | GO: 0006350~transcription | 136 | 14.58 | 8.00E-03 | 0.16 | 1.22 | 13.52 |
| MF | GO: 0030528~transcription regulator activity | 102 | 10.93 | 1.03E-02 | 0.20 | 1.26 | 14.84 |
| MF | GO: 0003677~DNA binding | 132 | 14.15 | 2.81E-01 | 0.88 | 1.06 | 99.40 |
| MF | GO: 0003700~transcription factor activity | 56 | 6.00 | 3.59E-01 | 0.92 | 1.07 | 99.90 |
| Annotation Cluster 9 | Enrichment Score: 3.31 | | | | | | |
| MF | GO: 0042054~histone methyltransferase activity | 10 | 1.07 | 1.70E-04 | 0.02 | 4.78 | 0.26 |
| MF | GO: 0016278~lysine N-methyltransferase activity | 9 | 0.96 | 2.16E-04 | 0.02 | 5.25 | 0.33 |
| MF | GO: 0016279~protein-lysine N-methyltransferase activity | 9 | 0.96 | 2.16E-04 | 0.02 | 5.25 | 0.33 |
| MF | GO: 0018024~histone-lysine N-methyltransferase activity | 9 | 0.96 | 2.16E-04 | 0.02 | 5.25 | 0.33 |
| MF | GO: 0008276~protein methyltransferase activity | 10 | 1.07 | 1.19E-03 | 0.05 | 3.73 | 1.82 |
| MF | GO: 0008170~N-methyltransferase activity | 9 | 0.96 | 6.78E-03 | 0.16 | 3.17 | 9.98 |
| Annotation Cluster 10 | Enrichment Score: 2.96 | | | | | | |
| BP | GO: 0042981~regulation of apoptosis | 73 | 7.82 | 7.19E-06 | 1.40E-03 | 1.71 | 0.01 |
| BP | GO: 0043067~regulation of programmed cell death | 73 | 7.82 | 9.92E-06 | 1.63E-03 | 1.69 | 0.02 |
| BP | GO: 0010941~regulation of cell death | 73 | 7.82 | 1.13E-05 | 1.60E-03 | 1.69 | 0.02 |
| BP | GO: 0043065~positive regulation of apoptosis | 39 | 4.18 | 1.37E-03 | 0.05 | 1.71 | 2.45 |
| BP | GO: 0043068~positive regulation of programmed cell death | 39 | 4.18 | 1.55E-03 | 0.05 | 1.70 | 2.76 |
| BP | GO: 0010942~positive regulation of cell death | 39 | 4.18 | 1.67E-03 | 0.05 | 1.69 | 2.98 |
| BP | GO: 0043066~negative regulation of apoptosis | 33 | 3.54 | 2.23E-03 | 0.07 | 1.76 | 3.96 |
| BP | GO: 0043069~negative regulation of programmed cell death | 33 | 3.54 | 2.77E-03 | 0.08 | 1.73 | 4.89 |
| BP | GO: 0060548~negative regulation of cell death | 33 | 3.54 | 2.89E-03 | 0.08 | 1.73 | 5.10 |
| BP | GO: 0006916~anti-apoptosis | 22 | 2.36 | 3.09E-03 | 0.08 | 2.01 | 5.44 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0006917~induction of apoptosis | 28 | 3.00 | 1.15E-02 | 0.20 | 1.65 | 18.82 |
| BP | GO: 0012502~induction of programmed cell death | 28 | 3.00 | 1.19E-02 | 0.20 | 1.64 | 19.49 |
| BP | GO: 0008624~induction of apoptosis by extracellular signals | 10 | 1.07 | 1.40E-01 | 0.73 | 1.68 | 93.41 |
| Annotation Cluster 11 | | Enrichment Score: 2.90 | | | | | |
| BP | GO: 0042325~regulation of phosphorylation | 46 | 4.93 | 6.99E-05 | 5.88E-03 | 1.86 | 0.13 |
| BP | GO: 0019220~regulation of phosphate metabolic process | 47 | 5.04 | 8.94E-05 | 6.47E-03 | 1.83 | 0.16 |
| BP | GO: 0051174~regulation of phosphorus metabolic process | 47 | 5.04 | 8.94E-05 | 6.47E-03 | 1.83 | 0.16 |
| BP | GO: 0033674~positive regulation of kinase activity | 27 | 2.89 | 2.33E-04 | 0.01 | 2.20 | 0.42 |
| BP | GO: 0044093~positive regulation of molecular function | 52 | 5.57 | 3.19E-04 | 0.02 | 1.67 | 0.58 |
| BP | GO: 0045860~positive regulation of protein kinase activity | 26 | 2.79 | 3.25E-04 | 0.02 | 2.20 | 0.59 |
| BP | GO: 0043549~regulation of kinase activity | 36 | 3.86 | 3.29E-04 | 0.02 | 1.90 | 0.59 |
| BP | GO: 0032268~regulation of cellular protein metabolic process | 44 | 4.72 | 3.96E-04 | 0.02 | 1.75 | 0.71 |
| BP | GO: 0051347~positive regulation of transferase activity | 27 | 2.89 | 4.23E-04 | 0.02 | 2.12 | 0.76 |
| BP | GO: 0051338~regulation of transferase activity | 36 | 3.86 | 7.03E-04 | 0.03 | 1.82 | 1.26 |
| BP | GO: 0001932~regulation of protein amino acid phosphorylation | 21 | 2.25 | 8.46E-04 | 0.03 | 2.29 | 1.52 |
| BP | GO: 0043405~regulation of MAP kinase activity | 18 | 1.93 | 1.27E-03 | 0.04 | 2.41 | 2.27 |
| BP | GO: 0045859~regulation of protein kinase activity | 33 | 3.54 | 1.47E-03 | 0.05 | 1.80 | 2.63 |
| BP | GO: 0000165~MAPKKK cascade | 21 | 2.25 | 1.81E-03 | 0.06 | 2.15 | 3.22 |
| BP | GO: 0043406~positive regulation of MAP kinase activity | 14 | 1.50 | 2.80E-03 | 0.08 | 2.59 | 4.94 |
| BP | GO: 0031399~regulation of protein modification process | 28 | 3.00 | 4.01E-03 | 0.10 | 1.79 | 7.02 |
| BP | GO: 0043085~positive regulation of catalytic activity | 42 | 4.50 | 7.01E-03 | 0.14 | 1.52 | 11.94 |
| BP | GO: 0043507~positive regulation of JUN kinase activity | 6 | 0.64 | 2.53E-02 | 0.33 | 3.53 | 37.09 |
| BP | GO: 0000187~activation of MAPK activity | 10 | 1.07 | 2.91E-02 | 0.36 | 2.30 | 41.43 |
| BP | GO: 0043408~regulation of MAPKKK cascade | 12 | 1.29 | 2.96E-02 | 0.36 | 2.07 | 41.87 |
| BP | GO: 0032147~activation of protein kinase activity | 12 | 1.29 | 3.92E-02 | 0.42 | 1.98 | 51.49 |
| Annotation Cluster 12 | | Enrichment Score: 2.78 | | | | | |
| MF | GO: 0042802~identical protein binding | 55 | 5.89 | 5.91E-04 | 0.04 | 1.60 | 0.91 |
| MF | GO: 0042803~protein homodimerization activity | 32 | 3.43 | 2.01E-03 | 0.08 | 1.79 | 3.07 |
| MF | GO: 0046983~protein dimerization activity | 45 | 4.82 | 3.81E-03 | 0.12 | 1.55 | 5.73 |
| Annotation Cluster 13 | | Enrichment Score: 2.76 | | | | | |
| BP | GO: 0009991~response to extracellular stimulus | 26 | 2.79 | 2.64E-04 | 0.01 | 2.23 | 0.48 |
| BP | GO: 0031667~response to nutrient levels | 24 | 2.57 | 3.10E-04 | 0.02 | 2.30 | 0.56 |
| BP | GO: 0007584~response to nutrient | 19 | 2.04 | 4.28E-04 | 0.02 | 2.56 | 0.77 |
| BP | GO: 0033273~response to vitamin | 12 | 1.29 | 6.39E-04 | 0.03 | 3.43 | 1.15 |
| BP | GO: 0033189~response to vitamin A | 8 | 0.86 | 6.08E-03 | 0.13 | 3.59 | 10.44 |
| BP | GO: 0032526~response to retinoic acid | 7 | 0.75 | 7.04E-03 | 0.14 | 4.00 | 12.00 |
| BP | GO: 0033280~response to vitamin D | 4 | 0.43 | 4.96E-02 | 0.47 | 4.71 | 60.12 |
| Annotation Cluster 14 | | Enrichment Score: 2.70 | | | | | |
| BP | GO: 0002263~cell activation during immune response | 10 | 1.07 | 8.11E-05 | 6.01E-03 | 5.23 | 0.15 |
| BP | GO: 0002366~leukocyte activation during immune response | 10 | 1.07 | 8.11E-05 | 6.01E-03 | 5.23 | 0.15 |
| BP | GO: 0002285~lymphocyte activation during immune response | 6 | 0.64 | 1.98E-03 | 0.06 | 6.28 | 3.53 |
| BP | GO: 0002274~myeloid leukocyte activation | 9 | 0.96 | 2.61E-03 | 0.07 | 3.69 | 4.61 |
| BP | GO: 0002286~T cell activation during immune response | 4 | 0.43 | 2.85E-02 | 0.35 | 5.80 | 40.68 |
| BP | GO: 0002275~myeloid cell activation during immune response | 4 | 0.43 | 6.68E-02 | 0.54 | 4.19 | 71.37 |
| Annotation Cluster 15 | | Enrichment Score: 2.54 | | | | | |
| BP | GO: 0008380~RNA splicing | 31 | 3.32 | 2.46E-04 | 0.01 | 2.06 | 0.44 |
| BP | GO: 0016071~mRNA metabolic process | 35 | 3.75 | 1.25E-03 | 0.04 | 1.78 | 2.24 |
| BP | GO: 0000377~RNA splicing, via transesterification reactions with bulged adenosine as nucleophile | 18 | 1.93 | 3.07E-03 | 0.08 | 2.22 | 5.41 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0000375~RNA splicing, via transesterification reactions | 18 | 1.93 | 3.07E-03 | 0.08 | 2.22 | 5.41 |
| BP | GO: 0000398~nuclear mRNA splicing, via spliceosome | 18 | 1.93 | 3.07E-03 | 0.08 | 2.22 | 5.41 |
| BP | GO: 0006397~mRNA processing | 30 | 3.22 | 3.53E-03 | 0.09 | 1.76 | 6.20 |
| BP | GO: 0006396~RNA processing | 39 | 4.18 | 5.25E-02 | 0.48 | 1.34 | 62.31 |
| Annotation Cluster 16 | | Enrichment Score: 2.47 | | | | | |
| MF | GO: 0005070~SH3/SH2 adaptor activity | 10 | 1.07 | 1.02E-03 | 0.05 | 3.81 | 1.57 |
| MF | GO: 0030674~protein binding, bridging | 13 | 1.39 | 4.27E-03 | 0.12 | 2.58 | 6.40 |
| MF | GO: 0060090~molecular adaptor activity | 10 | 1.07 | 9.07E-03 | 0.19 | 2.78 | 13.14 |
| Annotation Cluster 17 | | Enrichment Score: 2.45 | | | | | |
| BP | GO: 0002684~positive regulation of immune system process | 30 | 3.22 | 2.42E-05 | 0.00 | 2.37 | 0.04 |
| BP | GO: 0001817~regulation of cytokine production | 22 | 2.36 | 6.05E-04 | 0.03 | 2.29 | 1.09 |
| BP | GO: 0001819~positive regulation of cytokine production | 13 | 1.39 | 2.74E-03 | 0.08 | 2.72 | 4.85 |
| BP | GO: 0050778~positive regulation of immune response | 17 | 1.82 | 4.29E-03 | 0.11 | 2.21 | 7.48 |
| BP | GO: 0048584~positive regulation of response to stimulus | 22 | 2.36 | 1.40E-02 | 0.22 | 1.76 | 22.56 |
| BP | GO: 0032649~regulation of interferon-gamma production | 6 | 0.64 | 1.95E-02 | 0.28 | 3.77 | 29.99 |
| BP | GO: 0051240~positive regulation of multicellular organismal process | 18 | 1.93 | 1.51E-01 | 0.75 | 1.39 | 94.78 |
| Annotation Cluster 18 | | Enrichment Score: 2.19 | | | | | |
| BP | GO: 0043488~regulation of mRNA stability | 6 | 0.64 | 5.11E-03 | 0.12 | 5.14 | 8.85 |
| BP | GO: 0048255~mRNA stabilization | 5 | 0.54 | 6.68E-03 | 0.14 | 6.28 | 11.42 |
| BP | GO: 0043489~RNA stabilization | 5 | 0.54 | 6.68E-03 | 0.14 | 6.28 | 11.42 |
| BP | GO: 0043487~regulation of RNA stability | 6 | 0.64 | 7.56E-03 | 0.15 | 4.71 | 12.82 |
| Annotation Cluster 19 | | Enrichment Score: 2.11 | | | | | |
| MF | GO: 0030695~GTPase regulator activity | 42 | 4.50 | 6.06E-05 | 0.02 | 1.94 | 0.09 |
| MF | GO: 0060589~nucleoside-triphosphatase regulator activity | 42 | 4.50 | 9.85E-05 | 0.02 | 1.90 | 0.15 |
| MF | GO: 0005083~small GTPase regulator activity | 30 | 3.22 | 3.54E-04 | 0.03 | 2.04 | 0.55 |
| MF | GO: 0005096~GTPase activator activity | 23 | 2.47 | 3.55E-03 | 0.12 | 1.95 | 5.34 |
| MF | GO: 0008047~enzyme activator activity | 29 | 3.11 | 1.30E-02 | 0.22 | 1.61 | 18.37 |
| BP | GO: 0051056~regulation of small GTPase mediated signal transduction | 23 | 2.47 | 1.46E-02 | 0.23 | 1.72 | 23.32 |
| MF | GO: 0005085~guanyl-nucleotide exchange factor activity | 16 | 1.71 | 1.62E-02 | 0.25 | 1.96 | 22.33 |
| MF | GO: 0005099~Ras GTPase activator activity | 11 | 1.18 | 2.34E-02 | 0.30 | 2.25 | 30.61 |
| BP | GO: 0046578~regulation of Ras protein signal transduction | 19 | 2.04 | 3.03E-02 | 0.36 | 1.70 | 42.72 |
| BP | GO: 0035023~regulation of Rho protein signal transduction | 10 | 1.07 | 7.90E-02 | 0.58 | 1.90 | 77.45 |
| MF | GO: 0005088~Ras guanyl-nucleotide exchange factor activity | 8 | 0.86 | 1.91E-01 | 0.79 | 1.70 | 96.25 |
| MF | GO: 0005089~Rho guanyl-nucleotide exchange factor activity | 7 | 0.75 | 2.04E-01 | 0.80 | 1.76 | 97.05 |
| Annotation Cluster 20 | | Enrichment Score: 2.09 | | | | | |
| MF | GO: 0016563~transcription activator activity | 39 | 4.18 | 6.77E-04 | 0.04 | 1.77 | 1.04 |
| MF | GO: 0003713~transcription coactivator activity | 21 | 2.25 | 1.09E-02 | 0.20 | 1.83 | 15.59 |
| MF | GO: 0008134~transcription factor binding | 40 | 4.29 | 1.71E-02 | 0.26 | 1.45 | 23.40 |
| MF | GO: 0003712~transcription cofactor activity | 29 | 3.11 | 3.34E-02 | 0.38 | 1.49 | 40.88 |
| Annotation Cluster 21 | | Enrichment Score: 2.01 | | | | | |
| MF | GO: 0050431~transforming growth factor beta binding | 5 | 0.54 | 1.32E-03 | 0.05 | 9.33 | 2.02 |
| MF | GO: 0019838~growth factor binding | 13 | 1.39 | 1.03E-02 | 0.20 | 2.31 | 14.73 |
| MF | GO: 0019955~cytokine binding | 11 | 1.18 | 6.67E-02 | 0.53 | 1.88 | 65.61 |
| Annotation Cluster 22 | | Enrichment Score: 2.00 | | | | | |
| BP | GO: 0002684~positive regulation of immune system process | 30 | 3.22 | 2.42E-05 | 3.02E-03 | 2.37 | 0.04 |
| BP | GO: 0002694~regulation of leukocyte activation | 23 | 2.47 | 6.53E-05 | 5.81E-03 | 2.61 | 0.12 |
| BP | GO: 0050865~regulation of cell activation | 23 | 2.47 | 1.44E-04 | 9.73E-03 | 2.48 | 0.26 |
| BP | GO: 0002696~positive regulation of leukocyte activation | 16 | 1.71 | 4.55E-04 | 0.02 | 2.84 | 0.82 |
| BP | GO: 0002819~regulation of adaptive immune response | 11 | 1.18 | 6.37E-04 | 0.03 | 3.70 | 1.15 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0050867~positive regulation of cell activation | 16 | 1.71 | 7.46E-04 | 0.03 | 2.72 | 1.34 |
| BP | GO: 0050863~regulation of T cell activation | 16 | 1.71 | 1.29E-03 | 0.04 | 2.58 | 2.31 |
| BP | GO: 0051251~positive regulation of lymphocyte activation | 14 | 1.50 | 1.78E-03 | 0.06 | 2.72 | 3.16 |
| BP | GO: 0046635~positive regulation of alpha-beta T cell activation | 7 | 0.75 | 2.01E-03 | 0.06 | 5.07 | 3.57 |
| BP | GO: 0045621~positive regulation of lymphocyte differentiation | 8 | 0.86 | 2.09E-03 | 0.06 | 4.31 | 3.71 |
| BP | GO: 0050870~positive regulation of T cell activation | 12 | 1.29 | 2.11E-03 | 0.06 | 2.97 | 3.75 |
| BP | GO: 0051249~regulation of lymphocyte activation | 18 | 1.93 | 2.16E-03 | 0.06 | 2.29 | 3.83 |
| BP | GO: 0002822~regulation of adaptive immune response based on somatic recombination of immune receptors built from immunoglobulin superfamily domains | 10 | 1.07 | 2.23E-03 | 0.07 | 3.43 | 3.95 |
| BP | GO: 0046638~positive regulation of alpha-beta T cell differentiation | 6 | 0.64 | 3.29E-03 | 0.09 | 5.65 | 5.78 |
| BP | GO: 0045580~regulation of T cell differentiation | 9 | 0.96 | 5.04E-03 | 0.12 | 3.32 | 8.74 |
| BP | GO: 0045619~regulation of lymphocyte differentiation | 10 | 1.07 | 5.69E-03 | 0.13 | 2.99 | 9.81 |
| BP | GO: 0045582~positive regulation of T cell differentiation | 7 | 0.75 | 6.03E-03 | 0.13 | 4.12 | 10.36 |
| BP | GO: 0046637~regulation of alpha-beta T cell differentiation | 6 | 0.64 | 9.04E-03 | 0.17 | 4.52 | 15.15 |
| BP | GO: 0046634~regulation of alpha-beta T cell activation | 7 | 0.75 | 1.08E-02 | 0.19 | 3.66 | 17.88 |
| BP | GO: 0033081~regulation of T cell differentiation in the thymus | 4 | 0.43 | 1.78E-02 | 0.26 | 6.85 | 27.69 |
| BP | GO: 0043372~positive regulation of CD4-positive, alpha beta T cell differentiation | 4 | 0.43 | 1.78E-02 | 0.26 | 6.85 | 27.69 |
| BP | GO: 0002824~positive regulation of adaptive immune response on somatic recombination of immune receptors built from immunoglobulin superfamily domains | 6 | 0.64 | 1.95E-02 | 0.28 | 3.77 | 29.99 |
| BP | GO: 0002706~regulation of lymphocyte mediated immunity | 8 | 0.86 | 2.31E-02 | 0.31 | 2.79 | 34.52 |
| BP | GO: 0043370~regulation of CD4-positive, alpha beta T cell differentiation | 4 | 0.43 | 4.19E-02 | 0.43 | 5.02 | 53.86 |
| BP | GO: 0002683~negative regulation of immune system process | 9 | 0.96 | 7.24E-02 | 0.56 | 2.04 | 74.31 |
| BP | GO: 0048585~negative regulation of response to stimulus | 10 | 1.07 | 8.30E-02 | 0.59 | 1.88 | 79.14 |
| BP | GO: 0050871~positive regulation of B cell activation | 5 | 0.54 | 9.50E-02 | 0.63 | 2.85 | 83.58 |
| BP | GO: 0002823~negative regulation of adaptive immune response based on somatic recombination of immune receptors built from immunoglobulin superfamily domains | 3 | 0.32 | 1.12E-01 | 0.67 | 5.14 | 88.43 |
| BP | GO: 0002820~negative regulation of adaptive immune response | 3 | 0.32 | 1.12E-01 | 0.67 | 5.14 | 88.43 |
| BP | GO: 0050777~negative regulation of immune response | 4 | 0.43 | 1.44E-01 | 0.74 | 3.01 | 94.01 |
| BP | GO: 0045577~regulation of B cell differentiation | 3 | 0.32 | 2.07E-01 | 0.82 | 3.53 | 98.49 |
| BP | GO: 0050670~regulation of lymphocyte proliferation | 7 | 0.75 | 2.77E-01 | 0.88 | 1.59 | 99.71 |
| BP | GO: 0050864~regulation of B cell activation | 5 | 0.54 | 2.85E-01 | 0.89 | 1.85 | 99.77 |
| BP | GO: 0070663~positive regulation of B cell proliferation | 7 | 0.75 | 2.86E-01 | 0.89 | 1.57 | 99.77 |
| BP | GO: 0032944~regulation of mononuclear cell proliferation | 7 | 0.75 | 2.86E-01 | 0.89 | 1.57 | 99.77 |
| BP | GO: 0030888~regulation of B cell proliferation | 3 | 0.32 | 4.41E-01 | 0.96 | 2.02 | 100.00 |
| Annotation Cluster 23 | | Enrichment Score: 1.96 | | | | | |
| MF | GO: 0051020~GTPase binding | 14 | 1.50 | 5.41E-03 | 0.13 | 2.40 | 8.04 |
| MF | GO: 0017016~Ras GTPase binding | 12 | 1.29 | 9.14E-03 | 0.19 | 2.46 | 13.23 |
| MF | GO: 0017048~Rho GTPase binding | 7 | 0.75 | 1.47E-02 | 0.24 | 3.44 | 20.45 |
| MF | GO: 0031267~small GTPase binding | 12 | 1.29 | 1.90E-02 | 0.27 | 2.22 | 25.71 |
| Annotation Cluster 24 | | Enrichment Score: 1.85 | | | | | |
| BP | GO: 0006730~one-carbon metabolic process | 14 | 1.50 | 6.27E-03 | 0.14 | 2.36 | 10.76 |
| BP | GO: 0043414~biopolymer methylation | 10 | 1.07 | 1.03E-02 | 0.18 | 2.73 | 17.07 |
| BP | GO: 0006479~protein amino acid methylation | 7 | 0.75 | 1.59E-02 | 0.24 | 3.38 | 25.13 |
| BP | GO: 0008213~protein amino acid alkylation | 7 | 0.75 | 1.59E-02 | 0.24 | 3.38 | 25.13 |
| BP | GO: 0032259~methylation | 10 | 1.07 | 1.87E-02 | 0.27 | 2.48 | 28.92 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0016571~histone methylation | 5 | 0.54 | 2.67E-02 | 0.34 | 4.28 | 38.71 |
| Annotation Cluster 25 | | Enrichment Score: 1.84 | | | | | |
| BP | GO: 0010605~negative regulation of macromolecule metabolic process | 60 | 6.43 | 8.43E-04 | 0.03 | 1.54 | 1.51 |
| BP | GO: 0010629~negative regulation of gene expression | 41 | 4.39 | 6.89E-03 | 0.14 | 1.53 | 11.75 |
| BP | GO: 0016481~negative regulation of transcription | 38 | 4.07 | 7.21E-03 | 0.15 | 1.56 | 12.27 |
| BP | GO: 0010558~negative regulation of macromolecule biosynthetic process | 43 | 4.61 | 9.92E-03 | 0.18 | 1.48 | 16.50 |
| BP | GO: 0051253~negative regulation of RNA metabolic process | 31 | 3.32 | 1.03E-02 | 0.18 | 1.61 | 17.15 |
| BP | GO: 0009890~negative regulation of biosynthetic process | 44 | 4.72 | 1.32E-02 | 0.22 | 1.45 | 21.42 |
| BP | GO: 0045892~negative regulation of transcription, DNA-dependent | 30 | 3.22 | 1.41E-02 | 0.22 | 1.59 | 22.68 |
| BP | GO: 0051172~negative regulation of nitrogen compound metabolic process | 40 | 4.29 | 1.77E-02 | 0.26 | 1.45 | 27.59 |
| BP | GO: 0045934~negative regulation of nucleobase, nucleoside, nucleotide and nucleic acid metabolic process | 39 | 4.18 | 2.23E-02 | 0.30 | 1.44 | 33.48 |
| BP | GO: 0031327~negative regulation of cellular biosynthetic process | 42 | 4.50 | 2.26E-02 | 0.30 | 1.41 | 33.87 |
| MF | GO: 0016564~transcription repressor activity | 25 | 2.68 | 5.35E-02 | 0.48 | 1.48 | 57.28 |
| BP | GO: 0000122~negative regulation of transcription from RNA polymerase II promoter | 18 | 1.93 | 2.44E-01 | 0.86 | 1.27 | 99.37 |
| Annotation Cluster 26 | | Enrichment Score: 1.79 | | | | | |
| BP | GO: 0046907~intracellular transport | 61 | 6.54 | 2.43E-05 | 2.91E-03 | 1.75 | 0.04 |
| BP | GO: 0045184~establishment of protein localization | 57 | 6.11 | 9.44E-03 | 0.18 | 1.40 | 15.77 |
| BP | GO: 0015031~protein transport | 56 | 6.00 | 1.16E-02 | 0.20 | 1.38 | 19.05 |
| BP | GO: 0008104~protein localization | 63 | 6.75 | 1.32E-02 | 0.22 | 1.35 | 21.32 |
| BP | GO: 0006886~intracellular protein transport | 25 | 2.68 | 1.91E-01 | 0.80 | 1.26 | 97.82 |
| BP | GO: 0034613~cellular protein localization | 27 | 2.89 | 1.99E-01 | 0.81 | 1.24 | 98.19 |
| BP | GO: 0070727~cellular macromolecule localization | 27 | 2.89 | 2.10E-01 | 0.83 | 1.23 | 98.59 |
| Annotation Cluster 27 | | Enrichment Score: 1.75 | | | | | |
| BP | GO: 0010033~response to organic substance | 61 | 6.54 | 3.21E-04 | 0.02 | 1.59 | 0.58 |
| BP | GO: 0009725~response to hormone stimulus | 32 | 3.43 | 6.98E-03 | 0.14 | 1.64 | 11.90 |
| BP | GO: 0032870~cellular response to hormone stimulus | 14 | 1.50 | 2.41E-02 | 0.32 | 1.98 | 35.71 |
| BP | GO: 0009719~response to endogenous stimulus | 32 | 3.43 | 2.53E-02 | 0.32 | 1.49 | 37.09 |
| BP | GO: 0043434~response to peptide hormone stimulus | 15 | 1.61 | 3.42E-02 | 0.39 | 1.84 | 46.67 |
| BP | GO: 0032868~response to insulin stimulus | 10 | 1.07 | 8.30E-02 | 0.59 | 1.88 | 79.14 |
| BP | GO: 0032869~cellular response to insulin stimulus | 7 | 0.75 | 1.51E-01 | 0.75 | 1.94 | 94.78 |
| Annotation Cluster 28 | | Enrichment Score: 1.73 | | | | | |
| BP | GO: 0042108~positive regulation of cytokine biosynthetic process | 9 | 0.96 | 3.43E-03 | 0.09 | 3.53 | 6.03 |
| BP | GO: 0042035~regulation of cytokine biosynthetic process | 11 | 1.18 | 5.47E-03 | 0.13 | 2.80 | 9.44 |
| BP | GO: 0032677~regulation of interleukin-8 production | 5 | 0.54 | 6.68E-03 | 0.14 | 6.28 | 11.42 |
| BP | GO: 0045414~regulation of interleukin-8 biosynthetic process | 4 | 0.43 | 9.79E-03 | 0.18 | 8.37 | 16.30 |
| BP | GO: 0045416~positive regulation of interleukin-8 biosynthetic process | 3 | 0.32 | 4.93E-02 | 0.47 | 8.07 | 59.94 |
| BP | GO: 0007249~I-kappaB kinase/NF-kappaB cascade | 4 | 0.43 | 6.56E-01 | 0.99 | 1.20 | 100.00 |
| Annotation Cluster 29 | | Enrichment Score: 1.66 | | | | | |
| BP | GO: 0007044~cell-substrate junction assembly | 6 | 0.64 | 6.25E-03 | 0.14 | 4.92 | 10.72 |
| BP | GO: 0034329~cell junction assembly | 7 | 0.75 | 2.00E-02 | 0.28 | 3.22 | 30.63 |
| BP | GO: 0034330~cell junction organization | 7 | 0.75 | 8.01E-02 | 0.58 | 2.31 | 77.91 |
| Annotation Cluster 30 | | Enrichment Score: 1.64 | | | | | |
| BP | GO: 0045669~positive regulation of osteoblast differentiation | 6 | 0.64 | 9.04E-03 | 0.17 | 4.52 | 15.15 |
| BP | GO: 0045667~regulation of osteoblast differentiation | 7 | 0.75 | 2.48E-02 | 0.32 | 3.07 | 36.55 |
| BP | GO: 0030278~regulation of ossification | 9 | 0.96 | 5.39E-02 | 0.49 | 2.17 | 63.30 |
| Annotation Cluster 31 | | Enrichment Score: 1.61 | | | | | |
| BP | GO: 0048524~positive regulation of viral reproduction | 4 | 0.43 | 1.34E-02 | 0.22 | 7.54 | 21.72 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0050792~regulation of viral reproduction | 5 | 0.54 | 2.28E-02 | 0.30 | 4.49 | 34.08 |
| BP | GO: 0046782~regulation of viral transcription | 3 | 0.32 | 4.93E-02 | 0.47 | 8.07 | 59.94 |
| Annotation Cluster 32 | | Enrichment Score: 1.56 | | | | | |
| BP | GO: 0007044~cell-substrate junction assembly | 6 | 0.64 | 6.25E-03 | 0.14 | 4.92 | 10.72 |
| BP | GO: 0007160~cell-matrix adhesion | 10 | 1.07 | 4.58E-02 | 0.46 | 2.12 | 57.18 |
| BP | GO: 0031589~cell-substrate adhesion | 10 | 1.07 | 7.52E-02 | 0.57 | 1.92 | 75.68 |
| Annotation Cluster 33 | | Enrichment Score: 1.55 | | | | | |
| BP | GO: 0002819~regulation of adaptive immune response | 11 | 1.18 | 6.37E-04 | 0.03 | 3.70 | 1.15 |
| BP | GO: 0002822~regulation of adaptive immune response based on somatic recombination of immune receptors built from immunoglobulin superfamily domains | 10 | 1.07 | 2.23E-03 | 0.07 | 3.43 | 3.95 |
| BP | GO: 0002697~regulation of immune effector process | 14 | 1.50 | 2.56E-03 | 0.07 | 2.61 | 4.53 |
| BP | GO: 0050778~positive regulation of immune response | 17 | 1.82 | 4.29E-03 | 0.11 | 2.21 | 7.48 |
| BP | GO: 0002703~regulation of leukocyte mediated immunity | 10 | 1.07 | 4.58E-03 | 0.11 | 3.09 | 7.97 |
| BP | GO: 0002821~positive regulation of adaptive immune response | 7 | 0.75 | 5.12E-03 | 0.12 | 4.25 | 8.87 |
| BP | GO: 0002699~positive regulation of immune effector process | 8 | 0.86 | 7.88E-03 | 0.16 | 3.43 | 13.33 |
| BP | GO: 0001910~regulation of leukocyte mediated cytotoxicity | 6 | 0.64 | 9.04E-03 | 0.17 | 4.52 | 15.15 |
| BP | GO: 0031349~positive regulation of defense response | 10 | 1.07 | 1.46E-02 | 0.23 | 2.58 | 23.42 |
| BP | GO: 0031341~regulation of cell killing | 6 | 0.64 | 1.47E-02 | 0.23 | 4.04 | 23.47 |
| BP | GO: 0002824~positive regulation of adaptive immune response based on somatic recombination of immune receptors built from immunoglobulin superfamily domains | 6 | 0.64 | 1.95E-02 | 0.28 | 3.77 | 29.99 |
| BP | GO: 0001912~positive regulation of leukocyte mediated cytotoxicity | 5 | 0.54 | 2.28E-02 | 0.30 | 4.49 | 34.08 |
| BP | GO: 0002706~regulation of lymphocyte mediated immunity | 8 | 0.86 | 2.31E-02 | 0.31 | 2.79 | 34.52 |
| BP | GO: 0002705~positive regulation of leukocyte mediated immunity | 6 | 0.64 | 3.21E-02 | 0.38 | 3.32 | 44.54 |
| BP | GO: 0002708~positive regulation of lymphocyte mediated immunity | 6 | 0.64 | 3.21E-02 | 0.38 | 3.32 | 44.54 |
| BP | GO: 0045089~positive regulation of innate immune response | 7 | 0.75 | 3.34E-02 | 0.38 | 2.87 | 45.94 |
| BP | GO: 0031343~positive regulation of cell killing | 5 | 0.54 | 3.57E-02 | 0.39 | 3.93 | 48.18 |
| BP | GO: 0045088~regulation of innate immune response | 7 | 0.75 | 6.49E-02 | 0.53 | 2.44 | 70.31 |
| BP | GO: 0001914~regulation of T cell mediated cytotoxicity | 3 | 0.32 | 7.88E-02 | 0.58 | 6.28 | 77.36 |
| BP | GO: 0002891~positive regulation of immunoglobulin mediated immune response | 3 | 0.32 | 1.12E-01 | 0.67 | 5.14 | 88.43 |
| BP | GO: 0002714~positive regulation of B cell mediated immunity | 3 | 0.32 | 1.12E-01 | 0.67 | 5.14 | 88.43 |
| BP | GO: 0002889~regulation of immunoglobulin mediated immune response | 4 | 0.43 | 1.32E-01 | 0.71 | 3.14 | 92.23 |
| BP | GO: 0002712~regulation of B cell mediated immunity | 4 | 0.43 | 1.32E-01 | 0.71 | 3.14 | 92.23 |
| BP | GO: 0045954~positive regulation of natural killer cell mediated cytotoxicity | 3 | 0.32 | 2.07E-01 | 0.82 | 3.53 | 98.49 |
| BP | GO: 0002717~positive regulation of natural killer cell mediated immunity | 3 | 0.32 | 2.07E-01 | 0.82 | 3.53 | 98.49 |
| BP | GO: 0042269~regulation of natural killer cell mediated cytotoxicity | 3 | 0.32 | 2.27E-01 | 0.84 | 3.32 | 99.05 |
| BP | GO: 0002715~regulation of natural killer cell mediated immunity | 3 | 0.32 | 2.27E-01 | 0.84 | 3.32 | 99.05 |
| BP | GO: 0002709~regulation of T cell mediated immunity | 3 | 0.32 | 3.07E-01 | 0.90 | 2.69 | 99.87 |
| Annotation Cluster 34 | | Enrichment Score: 1.55 | | | | | |
| BP | GO: 0043405~regulation of MAP kinase activity | 18 | 1.93 | 1.27E-03 | 0.04 | 2.41 | 2.27 |
| BP | GO: 0043406~positive regulation of MAP kinase activity | 14 | 1.50 | 2.80E-03 | 0.08 | 2.59 | 4.94 |
| BP | GO: 0043506~regulation of JUN kinase activity | 7 | 0.75 | 1.24E-02 | 0.21 | 3.56 | 20.15 |
| BP | GO: 0043507~positive regulation of JUN kinase activity | 6 | 0.64 | 2.53E-02 | 0.33 | 3.53 | 37.09 |
| BP | GO: 0043408~regulation of MAPKKK cascade | 12 | 1.29 | 2.96E-02 | 0.36 | 2.07 | 41.87 |
| BP | GO: 0080135~regulation of cellular response to stress | 11 | 1.18 | 4.62E-02 | 0.46 | 2.01 | 57.51 |
| BP | GO: 0046328~regulation of JNK cascade | 8 | 0.86 | 5.56E-02 | 0.49 | 2.32 | 64.44 |
| BP | GO: 0070302~regulation of stress-activated protein kinase signaling pathway | 8 | 0.86 | 7.21E-02 | 0.56 | 2.18 | 74.16 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0007254~JNK cascade | 7 | 0.75 | 9.12E−02 | 0.61 | 2.24 | 82.27 |
| BP | GO: 0031098~stress-activated protein kinase signaling pathway | 7 | 0.75 | 1.16E−01 | 0.68 | 2.09 | 89.20 |
| BP | GO: 0007257~activation of JUN kinase activity | 4 | 0.43 | 1.57E−01 | 0.76 | 2.90 | 95.43 |
| Annotation Cluster 35 | Enrichment Score: 1.54 | | | | | | |
| BP | GO: 0051272~positive regulation of cell motion | 13 | 1.39 | 5.55E−03 | 0.13 | 2.50 | 9.57 |
| BP | GO: 0030335~positive regulation of cell migration | 11 | 1.18 | 1.91E−02 | 0.27 | 2.33 | 29.46 |
| BP | GO: 0051270~regulation of cell motion | 18 | 1.93 | 2.76E−02 | 0.35 | 1.76 | 39.75 |
| BP | GO: 0040017~positive regulation of locomotion | 11 | 1.18 | 3.46E−02 | 0.29 | 2.11 | 47.10 |
| BP | GO: 0030334~regulation of cell migration | 15 | 1.61 | 6.51E−02 | 0.53 | 1.67 | 70.40 |
| BP | GO: 0040012~regulation of locomotion | 16 | 1.71 | 8.57E−02 | 0.60 | 1.57 | 80.20 |
| Annotation Cluster 36 | Enrichment Score: 1.47 | | | | | | |
| BP | GO: 0030217~T cell differentiation | 12 | 1.29 | 5.58E−04 | 0.02 | 3.48 | 1.01 |
| BP | GO: 0046632~alpha-beta T cell differentiation | 4 | 0.43 | 3.48E−02 | 0.39 | 5.38 | 47.34 |
| BP | GO: 0046631~alpha-beta T cell activation | 4 | 0.43 | 6.68E−02 | 0.54 | 4.19 | 71.37 |
| BP | GO: 0000904~cell morphoProbe-setis involved in differentiation | 7 | 0.75 | 9.91E−01 | 1.00 | 0.54 | 100.00 |
| Annotation Cluster 37 | Enrichment Score: 1.42 | | | | | | |
| BP | GO: 0006952~defense response | 50 | 5.36 | 2.72E−03 | 0.08 | 1.53 | 4.82 |
| BP | GO: 0009611~response to wounding | 36 | 3.86 | 1.04E−01 | 0.65 | 1.28 | 86.34 |
| BP | GO: 0006954~inflammatory response | 22 | 2.36 | 2.00E−01 | 0.81 | 1.28 | 98.24 |
| Annotation Cluster 38 | Enrichment Score: 1.41 | | | | | | |
| BP | GO: 0007229~integrin-mediated signaling pathway | 9 | 0.96 | 3.12E−02 | 0.37 | 2.42 | 43.64 |
| MF | GO: 0005178~integrin binding | 8 | 0.86 | 3.73E−02 | 0.40 | 2.53 | 44.39 |
| BP | GO: 0033627~cell adhesion mediated by integrin | 3 | 0.32 | 4.93E−02 | 0.47 | 8.07 | 59.94 |
| Annotation Cluster 39 | Enrichment Score: 1.40 | | | | | | |
| BP | GO: 0050778~positive regulation of immune response | 17 | 1.82 | 4.29E−03 | 0.11 | 2.21 | 7.48 |
| BP | GO: 0002699~positive regulation of immune effector process | 8 | 0.86 | 7.88E−03 | 0.16 | 3.43 | 13.33 |
| BP | GO: 0031349~positive regulation of defense response | 10 | 1.07 | 1.46E−02 | 0.23 | 2.58 | 23.42 |
| BP | GO: 0002757~immune response-activating signal transduction | 8 | 0.86 | 1.91E−02 | 0.27 | 2.90 | 29.48 |
| BP | GO: 0002764~immune response-regulating signal transduction | 8 | 0.86 | 2.77E−02 | 0.35 | 2.69 | 39.82 |
| BP | GO: 0050852~T cell receptor signaling pathway | 5 | 0.54 | 3.10E−02 | 0.37 | 4.10 | 43.43 |
| BP | GO: 0045089~positive regulation of innate immune response | 7 | 0.75 | 3.34E−02 | 0.38 | 2.87 | 45.94 |
| BP | GO: 0002429~immune response-activating cell surface receptor signaling pathway | 6 | 0.64 | 5.36E−02 | 0.49 | 2.90 | 63.06 |
| BP | GO: 0045088~regulation of innate immune response | 7 | 0.75 | 6.49E−02 | 0.53 | 2.44 | 70.31 |
| BP | GO: 0002768~immune response-regulating cell surface receptor signaling pathway | 6 | 0.64 | 6.97E−02 | 0.55 | 2.69 | 72.92 |
| BP | GO: 0002758~innate immune response-activating signal transduction | 4 | 0.43 | 7.63E−02 | 0.57 | 3.97 | 76.22 |
| BP | GO: 0002218~activation of innate immune response | 4 | 0.43 | 7.63E−02 | 0.57 | 3.97 | 76.22 |
| BP | GO: 0050851~antigen receptor-mediated signaling pathway | 5 | 0.54 | 9.50E−02 | 0.63 | 2.85 | 83.58 |
| BP | GO: 0002253~activation of immune response | 9 | 0.96 | 1.25E−01 | 0.70 | 1.80 | 91.07 |
| BP | GO: 0002221~pattern recognition receptor signaling pathway | 3 | 0.32 | 2.27E−01 | 0.84 | 3.32 | 99.05 |
| Annotation Cluster 40 | Enrichment Score: 1.39 | | | | | | |
| BP | GO: 0000302~response to reactive oxygen species | 11 | 1.18 | 6.02E−03 | 0.13 | 2.76 | 10.34 |
| BP | GO: 0042542~response to hydrogen peroxide | 9 | 0.96 | 8.92E−03 | 0.17 | 3.03 | 14.97 |
| BP | GO: 0010035~response to inorganic substance | 18 | 1.93 | 4.51E−02 | 0.45 | 1.65 | 56.60 |
| BP | GO: 0006979~response to oxidative stress | 14 | 1.50 | 9.58E−02 | 0.63 | 1.61 | 83.82 |
| BP | GO: 0006800~oxygen and reactive oxygen species metabolic process | 5 | 0.54 | 4.78E−01 | 0.97 | 1.41 | 100.00 |
| Annotation Cluster 41 | Enrichment Score: 1.35 | | | | | | |
| BP | GO: 0009749~response to glucose stimulus | 7 | 0.75 | 3.04E−02 | 0.36 | 2.93 | 42.77 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0009746~response to hexose stimulus | 7 | 0.75 | 3.67E-02 | 0.40 | 2.81 | 49.13 |
| BP | GO: 0034284~response to monosaccharide stimulus | 7 | 0.75 | 3.67E-02 | 0.40 | 2.81 | 49.13 |
| BP | GO: 0009743~response to carbohydrate stimulus | 7 | 0.75 | 9.71E-02 | 0.63 | 2.20 | 84.22 |
| Annotation Cluster 42 | | Enrichment Score: 1.34 | | | | | |
| MF | GO: 0016702~oxidoreductase activity, acting on single donors with incorporation of molecular oxygen, incorporation of two atoms of oxygen | 9 | 0.96 | 2.40E-02 | 0.31 | 2.54 | 31.31 |
| MF | GO: 0016701~oxidoreductase activity, acting on single donors with incorporation of molecular oxygen | 9 | 0.96 | 2.60E-02 | 0.32 | 2.51 | 33.48 |
| MF | GO: 0005506~iron ion binding | 22 | 2.36 | 1.53E-01 | 0.73 | 1.33 | 92.29 |
| Annotation Cluster 43 | | Enrichment Score: 1.27 | | | | | |
| BP | GO: 0007049~cell cycle | 57 | 6.11 | 1.08E-02 | 0.19 | 1.38 | 17.84 |
| BP | GO: 0000278~mitotic cell cycle | 31 | 3.32 | 1.35E-02 | 0.22 | 1.58 | 21.81 |
| BP | GO: 0022402~cell cycle process | 42 | 4.50 | 2.52E-02 | 0.33 | 1.40 | 36.92 |
| BP | GO: 0000082~G1/S transition of mitotic cell cycle | 8 | 0.86 | 2.77E-02 | 0.35 | 2.69 | 39.82 |
| BP | GO: 0022403~cell cycle phase | 32 | 3.43 | 3.30E-02 | 0.38 | 1.46 | 45.46 |
| BP | GO: 0051329~interphase of mitotic cell cycle | 11 | 1.18 | 4.62E-02 | 0.46 | 2.01 | 57.51 |
| BP | GO: 0000087~M phase of mitotic cell cycle | 19 | 2.04 | 5.17E-02 | 0.48 | 1.60 | 61.72 |
| BP | GO: 0051325~interphase | 11 | 1.18 | 5.43E-02 | 0.49 | 1.96 | 63.58 |
| BP | GO: 0007067~mitosis | 18 | 1.93 | 7.65E-02 | 0.57 | 1.54 | 76.31 |
| BP | GO: 0000280~nuclear division | 18 | 1.93 | 7.65E-02 | 0.57 | 1.54 | 76.31 |
| BP | GO: 0048285~organelle fission | 18 | 1.93 | 1.01E-01 | 0.64 | 1.48 | 85.44 |
| BP | GO: 0000279~M phase | 21 | 2.25 | 2.92E-01 | 0.89 | 1.20 | 99.81 |
| BP | GO: 0051301~cell division | 18 | 1.93 | 3.93E-01 | 0.95 | 1.15 | 99.99 |
| Annotation Cluster 44 | | Enrichment Score: 1.27 | | | | | |
| BP | GO: 0002252~immune effector process | 19 | 2.04 | 2.48E-04 | 0.01 | 2.67 | 0.45 |
| BP | GO: 0002443~leukocyte mediated immunity | 11 | 1.18 | 1.53E-02 | 0.23 | 2.41 | 24.36 |
| BP | GO: 0002467~germinal center formation | 3 | 0.32 | 1.57E-02 | 0.24 | 14.13 | 24.85 |
| BP | GO: 0002449~lymphocyte mediated immunity | 8 | 0.86 | 7.66E-02 | 0.57 | 2.15 | 76.36 |
| BP | GO: 0002460~adaptive immune response based on somatic recombination of immune receptors built from immunoglobulin superfamily domains | 7 | 0.75 | 2.23E-01 | 0.84 | 1.71 | 98.96 |
| BP | GO: 0002250~adaptive immune response | 7 | 0.75 | 2.23E-01 | 0.84 | 1.71 | 98.96 |
| BP | GO: 0016064~immunoglobulin mediated immune response | 4 | 0.43 | 5.51E-01 | 0.98 | 1.40 | 100.00 |
| BP | GO: 0019724~B cell mediated immunity | 4 | 0.43 | 5.76E-01 | 0.99 | 1.35 | 100.00 |
| Annotation Cluster 45 | | Enrichment Score: 1.22 | | | | | |
| BP | GO: 0010627~regulation of protein kinase cascade | 24 | 2.57 | 6.78E-03 | 0.14 | 1.82 | 11.58 |
| BP | GO: 0009967~positive regulation of signal transduction | 23 | 2.47 | 6.65E-02 | 0.53 | 1.47 | 71.19 |
| BP | GO: 0010647~positive regulation of cell communication | 24 | 2.57 | 1.06E-01 | 0.65 | 1.37 | 86.74 |
| BP | GO: 0010740~positive regulation of protein kinase cascade | 12 | 1.29 | 2.72E-01 | 0.88 | 1.35 | 99.68 |
| Annotation Cluster 46 | | Enrichment Score: 1.21 | | | | | |
| BP | GO: 0051651~maintenance of location in cell | 7 | 0.75 | 4.01E-02 | 0.42 | 2.75 | 52.31 |
| BP | GO: 0051235~maintenance of location | 8 | 0.86 | 5.18E-02 | 0.48 | 2.36 | 61.81 |
| BP | GO: 0032507~maintenance of protein location in cell | 6 | 0.64 | 6.40E-02 | 0.53 | 2.76 | 69.79 |
| BP | GO: 0045185~maintenance of protein location | 6 | 0.64 | 1.09E-01 | 0.66 | 2.36 | 87.58 |
| Annotation Cluster 47 | | Enrichment Score: 1.21 | | | | | |
| BP | GO: 0033619~membrane protein proteolysis | 5 | 0.54 | 1.92E-02 | 0.27 | 4.71 | 29.61 |
| BP | GO: 0006509~membrane protein ectodomain proteolysis | 4 | 0.43 | 4.19E-02 | 0.43 | 5.02 | 53.86 |
| BP | GO: 0007219~Notch signaling pathway | 5 | 0.54 | 2.97E-01 | 0.90 | 1.81 | 99.83 |
| Annotation Cluster 48 | | Enrichment Score: 1.20 | | | | | |
| BP | GO: 0001906~cell killing | 5 | 0.54 | 3.57E-02 | 0.39 | 3.93 | 48.18 |

TABLE 14-continued

Term centric functional annotation clustering that shows annotation groups that are enriched for the 1142 probe sets.

| Category | Term | Count | % | P value | adjusted P value | Fold Enrichment | FDR |
|---|---|---|---|---|---|---|---|
| BP | GO: 0042267~natural killer cell mediated cytotoxicity | 3 | 0.32 | 6.35E-02 | 0.53 | 7.07 | 69.47 |
| BP | GO: 0002228~natural killer cell mediated immunity | 3 | 0.32 | 6.35E-02 | 0.53 | 7.07 | 69.47 |
| BP | GO: 0002449~lymphocyte mediated immunity | 8 | 0.86 | 7.66E-02 | 0.57 | 2.15 | 76.36 |
| BP | GO: 0001909~leukocyte mediated cytotoxicity | 3 | 0.32 | 9.52E-02 | 0.63 | 5.65 | 83.62 |
| Annotation Cluster 49 | Enrichment Score: 1.19 | | | | | | |
| BP | GO: 0010332~response to gamma radiation | 6 | 0.64 | 6.25E-03 | 0.14 | 4.92 | 10.72 |
| BP | GO: 0010212~response to ionizing radiation | 8 | 0.86 | 3.85E-02 | 0.41 | 2.51 | 50.87 |
| BP | GO: 0009314~response to radiation | 15 | 1.61 | 1.76E-01 | 0.79 | 1.41 | 96.98 |
| BP | GO: 0033077~T cell differentiation in the thymus | 3 | 0.32 | 4.23E-01 | 0.96 | 2.09 | 100.00 |
| Annotation Cluster 50 | Enrichment Score: 1.17 | | | | | | |
| BP | GO: 0001824~blastocyst development | 9 | 0.96 | 1.67E-03 | 0.06 | 3.94 | 2.97 |
| BP | GO: 0001829~trophectodermal cell differentiation | 3 | 0.32 | 2.07E-01 | 0.82 | 3.53 | 98.49 |
| BP | GO: 0001890~placenta development | 6 | 0.64 | 2.11E-01 | 0.83 | 1.88 | 98.64 |
| BP | GO: 0001825~blastocyst formation | 3 | 0.32 | 2.87E-01 | 0.89 | 2.83 | 99.78 |

Top 50 clusters were included. The rest of the 50 clusters are decreasing in statistical significance and not shown.
Abbreviations:
BP; biological process.
MF: molecular function.
Adjusted P value is based on Benjamini method.

TABLE 15

KEGG pathway enrichment analysis using DAVID. The results are consistent with IPA pathway enrichment analysis.

| # of Genes | KEGG Pathway | B-H adjusted P value |
|---|---|---|
| 21 | T cell receptor signaling pathway | 2.43E−04 |
| 18 | Fc gamma R-mediated phagocytosis | 1.20E−03 |
| 20 | Neurotrophin signaling pathway | 2.50E−03 |
| 15 | Fc epsilon R1 signaling pathway | 3.26E−03 |
| 20 | Natural killer cell mediated cytotoxicity | 3.30E−03 |
| 26 | Focal adhesion | 3.66E−03 |
| 14 | B cell receptor signaling pathway | 4.79E−03 |
| 26 | Regulation of actin cytoskeleton | 6.65E−03 |
| 14 | Small cell lung cancer | 0.01 |
| 13 | Chronic myeloid leukemia | 0.01 |
| 20 | Jak-STAT signaling pathway | 0.01 |
| 33 | Pathways in cancer | 0.01 |
| 18 | Insulin signaling pathway | 0.02 |
| 22 | Chemokine signaling pathway | 0.02 |
| 28 | MAPK signaling pathway | 0.02 |
| 16 | Leukocyte transendothelial migration | 0.02 |
| 13 | Hematopoietic cell lineage | 0.02 |
| 12 | VEGF signaling pathway | 0.02 |
| 10 | Non-small cell lung cancer | 0.02 |
| 10 | Pathogenic Escherichia coli infection | 0.03 |

Example 2

TABLE 6

Gene panel

| Gene Name | Gene Symbol |
|---|---|
| Thrombospodin 1 | THBS1 |
| Rho guanine nucleotide exchange factor (GEF 7) | ARHGEF7 |
| MyoD family inhibitor domain containing | MDFIC |
| Cyclin D2 | CCND2 |
| Oxysterol binding protein-like 8 | OSBPL8 |
| DDB1 and CUL4 associated factor 7 | DCAF7 |
| Transmembrane protein 50B | TMEM50B |
| Golgin A8 family, member B | GOLGA8A/GOLGA8B |
| SWI/SNF related, matrix associated, actin dependent regulator of chromatin subfamily a, member 4 | SMARCA4 |
| Wolf-Hirschhorn syndrome candidate 1-like 1 | WHSC1L1 |
| Unnamed gene associated with the 1556747_a_at probe | NA |
| Unnamed gene associated with the 1562957_at probe | NA |

1556747_a_at identifies a novel long non-coding RNA gene "LOC101928343", NCBI gene id is 101928343, and Ensembl ID is ENSG000002612227, human gene symbol is CTD-2006K23.1.

1562957_at identifies a long non-coding RNA gene "L1NC00869", NCBI gene ID is 57234, and Ensembl ID is ENSG00000226067, human gene symbol is LINC00869.

As described herein, a multivariate logistic regression model was developed for calculating the probability that a patient develops infections, e.g., multiple infections. This specific panel of genes, or the subsets thereof described herein, have never previously been described to have the ability to predict the outcome of multiple infections. Moreover, the prediction of multiple infections as an outcome using logistic regression models has never previously been described. The use of the specific panel(s) described herein, optionally combined with the use of logistic regression models, successfully predict the outcome of multiple infections. Given the expression value of each of the 12 genes (e.g. in an adult patient) or 5 gene panel (e.g., in a pediatric patient), in its entirety, or as a subset, the algorithm is able to predict the probability of multiple infections, e.g., using Glue Grant patients to build the predictive models. Information on the Total Body Surface Area (TBSA) burns, age and inhalation status (yes or no) can also be used in conjunction with the gene panel to improve prediction.

In this Example and some embodiments of the various aspect described herein, the expression values are numerical values of each of the genes, or a subset, derived from for example, microarray probe set expression level value, or by qPCR.

An example of the implementation of the algorithm is as such. Using the R software for this example and using microarray expression data of the entire 12 gene panel, with age, TBSA and inhalation status, the following code is run to obtain the coefficient of each of the covariate for the outcome of multiple infections in a given population, which in this case used the data from the GLUE grant.

mylogit←glm(Outcome~AGE+TBSA+Inhal_inj+ X1556747_a_at +X1562957_at +X200951_s_at +X201108_s_at +X201109_s_at +X201110_s_at +X208797_s_at +X217599_s_at +X217656_at +X221248_s_at +X222907_x_at +X224730 at +X228986 at +X235412 at, data=covariates, family="binomial")

Age, TBSA and inhalation injury status, and the measured gene expression values of the 12 genes of each patient to be analyzed/predicted ("new data") can then be entered into the following code implemented in the R software to predict the outcome of each patient:

predicted←predict.glm(mylogit, newdata=patient, type="response", se. fit=TRUE)

patient is an R data frame containing age, TBSA, inhalation injury status, and the expression values of each of the 12 genes, in its entirety or as a subset, but always consistent with which covariates were used in the first formula.

The probability for multiple infection is stored in predicted$fit, and the 95% concidence interval is then calculated from the standard error stored in predicted$se.fit, by the formula predicted probability minus 1.96*standard error for the lower bound and predicted probability plus 1.96*standard error for the upper bound.

TABLE 7

Example coefficients of combined model, from microarray-derived data

| Covariates | Coefficient Estimates |
|---|---|
| Intercept | −1.1912 |
| TBSA | 0.0423 |
| Age | 0.0652 |
| Inhalation Injury (Yes) | 3.5132 |
| 1556747_a_at (LOC101928343) | −0.6652 |
| 1562957_at (LINC00869) | 0.803 |
| 200951_s_at (CCND2) | 0.033 |
| 201108_s_at (THBS1) | 0.8321 |
| 201109_s_at (THBS1) | 0.8448 |
| 201110_s_at (THBS1) | 0.0714 |
| 208797_s_at (GOLGA8A/GOLGA8B) | −0.731 |
| 217599_s_at (MDFIC) | −0.146 |
| 217656_at (SMARCA4) | −1.0108 |
| 221248_s_at (WHSC1L1) | −1.2438 |
| 222907_x_at (TMEM50B) | −0.167 |

TABLE 7-continued

Example coefficients of combined model, from microarray-derived data

| Covariates | Coefficient Estimates |
|---|---|
| 224730_at (DCAF7) | −1.4905 |
| 228986_at (OSBPL8) | 0.1821 |
| 235412_at (ARHGEF7) | 0.8709 |

Minimal Sets.

The set of marker genes of Table 8 can be used to permit prosnosis for, and/or treatment plans to patients as described herein. In some embodiments, the set of genes of Table 8 can permit prosnosis for, and/or treatment plans to patients 16 years of age or older.

TABLE 8

| Minimal set, e.g. for adult blood samples | |
|---|---|
| CCND2 | cyclin D2 |
| THBS1 | thrombospondin 1 |
| MDFIC | MyoD family inhibitor domain containing |
| SMARCA4 | SWI/SNF related, matrix associated, actin dependent regulator of chromatin, subfamily a, member 4 |
| WHSC1L1 | Wolf-Hirschhorn syndrome candidate 1-like 1 |
| TMEM50B | transmembrane protein 50B |
| DCAF7 | DDB1 and CUL4 associated factor 7 |
| OSBPL8 | oxysterol binding protein-like 8 |

The set of marker genes of Table 9 can be permit prosnosis for, and/or treatment plans to patients as described herein. In some embodiments, the set of genes of Table 9 can permit prosnosis for, and/or treatment plans to patients of 15 years of age or younger.

TABLE 9

Minimal set, e.g. for pediatric blood samples. Fold change is in the hypersusceptible patients compared to those less vulnerable.

| | Minimal set for Pediatric Blood Samples | Fold Change |
|---|---|---|
| NFKB2 | nuclear factor of kappa light polypeptide gene enhancer in B-cells 2 (p49/p100) | 1.78 |

TABLE 9-continued

Minimal set, e.g. for pediatric blood samples. Fold change is in the hypersusceptible patients compared to those less vulnerable.

| | Minimal set for Pediatric Blood Samples | Fold Change |
|---|---|---|
| MAX | MYC associated factor X | 1.67 |
| PDLIM5 | PDZ and LIM domain 5 | −1.43 |
| GATAD2B | GATA zinc finger domain containing 2B | −1.50 |
| ZSCAN30 | zinc finger and SCAN domain containing 30 | −1.36 |

Additional Muscle Biomarkers:

Several ALDHs were also found to be associated with increase burn wound infections. In some embodiments, the level of one or more ALDHs of Table 10 can be used in the methods described herein to provide prognosis and/or treatment plans for a subject at risk of infection. In some embodiments, the level of ALDH is the level in the muscle of the subject.

TABLE 10

Muscle Expression of ALDHs

| Gene | Probe | Fold change in burn vs. healthy | Fold change in burn patients who had 2 or more burn wound infections than burn patients had no infection | Fold change in burn patients who had 3 or more burn wound infections than burn patients had no infection |
|---|---|---|---|---|
| ALDH1A1 | 212224_at | −2.55 | −1.65 | −1.64 |
| ALDH1A2 | 207016_s_at | — | −1.98 | −1.91 |
| ALDH3B1 | 211004_s_at | — | 1.85 | 1.91 |
| ALDH5A1 | 203608_at | −1.87 | −2.67 | −3.17 |
| ALDH6A1 | 221588_x_at | −1.42 | −1.76 | −1.82 |
| ALDH7A1 | 208950_s_at | −2.25 | — | −1.56 |

—: fold change <1.3 fold

What is claimed herein is:

1. A method of treatment of a burn patient 16 years of age or older suspected of being at risk of a *Pseudomonas* or *Staphylococci* infection or having a *Pseudomonas* or *Staphylococci* infection, the method comprising;
   a. determining the values of total body surface area (TBSA) burns, age, and inhalation status of the burn patient;
   b. obtaining a leukocyte sample, isolating RNA from the sample, and analyzing the isolated RNA using RT-PCR for gene expression levels of at least one gene selected from the group of: Thrombospondin 1 (THBS1), cyclin D2 (CCND2), MyoD family inhibitor domain containing (MDFIC), SWI/SNF related, matrix associated, actin dependent regulator of chromatin, subfamily a, member 4 (SMARCA4), nuclear receptor binding SET domain protein 3 (WHSC1L1), transmembrane protein 50B (TMEM50B), DDB1 and CUL4 associated factor 7 (DCAF7), and oxysterol binding protein like 8 (OSBPL8); and
   c. multiplying the TBSA value by 0.0423, multiplying the age value by 0.0652, multiplying the inhalation status value by 3.5132, and multiplying the expression level of each measured gene by a coefficient selected from the group of:
      0.8321 for the expression level of Thrombospondin 1 (THBS1) analyzed using sequence comprising probe 201108, 0.8448 for the expression level of Thrombospondin 1 (THBS1) analyzed using the sequence comprising probe 201109, 0.0714 for the expression level of Thrombospondin 1 (THBS1) analyzed using the sequence comprising probe 201110, 0.033 for the expression level of cyclin D2 (CCND2), −0.146 for the expression level of MyoD family inhibitor domain containing (MDFIC), −1.0108 for the expression level of SWI/SNF related, matrix associated, actin dependent regulator of chromatin, subfamily a, member 4 (SMARCA4), −1.2438 for the expression level of nuclear receptor binding SET domain protein 3 (WHSC1L1), −0.167 for the expression level of transmembrane protein 50B (TMEM50B), −1.4905 for the expression level of DDB1 and CUL4 associated factor 7 (DCAF7), 0.1821 for the expression level of oxysterol binding protein like 8 (OSBPL8), and adding the resulting products to yield a risk value; and d. administering a treatment selected from the group consisting of antibiotics; immunotherapy; and LPS removal when the risk value is greater than or about −1.1912.

2. The method of claim 1, wherein the sample comprises blood or plasma.

* * * * *